US008812329B2

(12) United States Patent
Showalter et al.

(10) Patent No.: US 8,812,329 B2
(45) Date of Patent: Aug. 19, 2014

(54) LABORATORY INSTRUMENTATION INFORMATION MANAGEMENT AND CONTROL NETWORK

(75) Inventors: Wayne Showalter, Tucson, AZ (US); Alain L. Larson, Marana, AZ (US)

(73) Assignee: Ventana Medical Systems, Inc., Tucson, AZ (US)

( * ) Notice: Subject to any disclaimer, the term of this patent is extended or adjusted under 35 U.S.C. 154(b) by 183 days.

(21) Appl. No.: 11/732,628

(22) Filed: Apr. 4, 2007

(65) Prior Publication Data

US 2007/0196909 A1    Aug. 23, 2007

Related U.S. Application Data

(63) Continuation-in-part of application No. 10/893,725, filed on Jul. 16, 2004.

(60) Provisional application No. 11/032,324, filed on Jan. 10, 2005, provisional application No. 60/487,998, filed on Jul. 17, 2003.

(51) Int. Cl.
*G06Q 50/22* (2012.01)
*G06Q 50/24* (2012.01)

(52) U.S. Cl.
USPC .................................................. 705/2; 705/3

(58) Field of Classification Search
CPC ............................... G06Q 50/22; G06Q 50/24
USPC ........................................................... 705/2
See application file for complete search history.

(56) References Cited

U.S. PATENT DOCUMENTS 4,360,671 A * 11/1982 Wojtowicz et al. ........... 544/192
4,855,909 A      8/1989 Vincent et al.
5,216,925 A      6/1993 Odernheimer
5,316,726 A      5/1994 Babson et al.
5,392,209 A      2/1995 Eason et al.
5,401,110 A      3/1995 Neeley (Continued)

FOREIGN PATENT DOCUMENTS

AU   2012209030 A1   8/2012
CA   2 326 039 A1   5/2002

(Continued)

OTHER PUBLICATIONS

Turner, E.; Paszko, C.; Kolva, D., *Implementing a Laboratory Information Management System (LIMS) in an Army Corps of Engineers' Water Quality Testing Laboratory*, Nov. 2001, vol. 6, No. 5, West End, NC, USA, pp. 60-63.

(Continued)

*Primary Examiner* — Valerie Lubin
*Assistant Examiner* — Reginald R Reyes
(74) *Attorney, Agent, or Firm* — Muirhead and Saturnelli, LLC

(57) ABSTRACT

An interface point network (IPN) and a method for communication with a laboratory information system using an IPN, wherein the IPN includes at least one host computer in communication with at least one laboratory instrument, the laboratory information system and an interface point server in communication with the host computer and the laboratory information system, the interface point server being configured to function as a communication interface between the host computer and the laboratory information system in a manner responsive to a predetermined communication protocol. Use of bar code and RFID labels for tracking samples and in maintaining sample data is described.

18 Claims, 32 Drawing Sheets

(56) References Cited

U.S. PATENT DOCUMENTS

| | | |
|---|---|---|
| 5,416,029 A | 5/1995 | Miller et al. |
| 5,439,649 A | 8/1995 | Tseung et al. |
| 5,529,166 A | 6/1996 | Markin et al. |
| 5,561,556 A | 10/1996 | Weissman |
| 5,598,295 A | 1/1997 | Olofson |
| 5,608,200 A | 3/1997 | Le Goff et al. |
| 5,614,415 A | 3/1997 | Markin |
| 5,625,706 A | 4/1997 | Lee et al. |
| 5,631,844 A | 5/1997 | Margrey et al. |
| 5,663,545 A | 9/1997 | Marquiss |
| 5,683,786 A * | 11/1997 | Kavanaugh ............... 428/195.1 |
| 5,690,892 A | 11/1997 | Babler et al. |
| 5,777,303 A | 7/1998 | Berney |
| 5,817,032 A | 10/1998 | Williamson, IV et al. |
| 5,842,179 A | 11/1998 | Beavers et al. |
| 5,875,286 A | 2/1999 | Bernstein et al. |
| 5,876,926 A | 3/1999 | Beecham |
| 5,892,900 A * | 4/1999 | Ginter et al. ............... 726/26 |
| 5,948,359 A | 9/1999 | Kalra et al. |
| 5,961,923 A | 10/1999 | Nova et al. |
| 5,963,368 A | 10/1999 | Domanik et al. |
| 5,985,670 A | 11/1999 | Markin |
| 6,018,713 A | 1/2000 | Coli et al. |
| 6,045,759 A | 4/2000 | Ford et al. |
| 6,055,487 A | 4/2000 | Margery et al. |
| 6,061,790 A * | 5/2000 | Bodnar ............... 713/171 |
| 6,064,754 A | 5/2000 | Parekh et al. |
| 6,066,300 A | 5/2000 | Carey et al. |
| 6,093,574 A | 7/2000 | Druyer-Sanchez et al. |
| 6,113,554 A | 9/2000 | Gilcher et al. |
| 6,330,348 B1 | 12/2001 | Kerschmann et al. |
| 6,387,653 B1 | 5/2002 | Voneiff et al. |
| 6,442,440 B1 | 8/2002 | Miller |
| 6,493,724 B1 | 12/2002 | Cusack et al. |
| 6,495,106 B1 | 12/2002 | Kalra et al. |
| 6,520,313 B1 | 2/2003 | Kaarakainen et al. |
| 6,535,129 B1 | 3/2003 | Petrick |
| 6,545,604 B1 * | 4/2003 | Dando et al. ............... 340/572.1 |
| 6,572,824 B1 | 6/2003 | Ostgaard et al. |
| 6,581,012 B1 | 6/2003 | Aryev et al. |
| 6,599,476 B1 | 7/2003 | Watson et al. |
| 6,615,763 B2 | 9/2003 | Edwards |
| 6,713,298 B2 * | 3/2004 | McDevitt et al. ........... 435/287.8 |
| 6,721,615 B2 | 4/2004 | Fava et al. |
| 6,770,487 B2 | 8/2004 | Crosby |
| 6,800,249 B2 | 10/2004 | de la Torre-Bueno |
| 6,814,257 B2 | 11/2004 | Kiene et al. |
| 6,889,165 B2 * | 5/2005 | Lind et al. ............... 702/183 |
| 6,890,759 B2 | 5/2005 | Bierre et al. |
| 6,910,053 B1 | 6/2005 | Pauly et al. |
| 6,917,696 B2 | 7/2005 | Soenksen |
| 6,919,044 B1 | 7/2005 | Shibata et al. |
| 6,927,779 B2 | 8/2005 | Mannion et al. |
| 6,941,762 B2 | 9/2005 | Felder et al. |
| 7,006,894 B2 | 2/2006 | De la Huerga |
| 7,035,877 B2 | 4/2006 | Markham et al. |
| 7,083,106 B2 * | 8/2006 | Albany ............... 235/492 |
| 7,141,213 B1 | 11/2006 | Pang et al. |
| 7,154,397 B2 * | 12/2006 | Zerhusen et al. .......... 340/573.1 |
| 7,163,728 B2 | 1/2007 | Finger |
| 7,226,788 B2 | 6/2007 | De La Torre-Bueno |
| 7,357,298 B2 | 4/2008 | Pokorny et al. |
| 7,382,258 B2 | 6/2008 | Oldham et al. |
| 7,400,983 B2 | 7/2008 | Feingold et al. |
| 7,468,161 B2 | 12/2008 | Reinhardt et al. |
| 7,562,025 B2 | 7/2009 | Mallett et al. |
| 7,584,019 B2 | 9/2009 | Feingold et al. |
| 7,587,432 B2 | 9/2009 | Pauly et al. |
| 7,588,728 B2 | 9/2009 | Clark et al. |
| 7,593,787 B2 | 9/2009 | Feingold et al. |
| 7,603,201 B2 | 10/2009 | Feingold et al. |
| 7,657,070 B2 | 2/2010 | Lefebvre |
| 7,660,724 B2 | 2/2010 | Mallett et al. |
| 7,664,656 B2 | 2/2010 | Mallett et al. |
| 7,666,355 B2 | 2/2010 | Alavie et al. |
| 7,678,331 B2 | 3/2010 | Shanafelter |
| 7,688,207 B2 | 3/2010 | Fritchie et al. |
| 7,745,204 B1 | 6/2010 | Aidun et al. |
| 7,754,149 B2 | 7/2010 | Sugiyama |
| 7,850,912 B2 | 12/2010 | Favuzzi et al. |
| 7,860,727 B2 | 12/2010 | Showalter et al. |
| 7,864,380 B2 | 1/2011 | Descour et al. |
| 7,968,051 B2 | 6/2011 | Oonuma |
| 7,996,172 B2 | 8/2011 | Bauer et al. |
| 8,035,485 B2 | 10/2011 | Fritchie |
| 8,062,591 B2 | 11/2011 | Yamamoto |
| 2001/0035962 A1 | 11/2001 | Yundt-Pacheco |
| 2002/0013787 A1 | 1/2002 | Pollard et al. |
| 2002/0026331 A1 | 2/2002 | Case |
| 2002/0029156 A1 | 3/2002 | O'Dowd |
| 2002/0030598 A1 | 3/2002 | Dombrowski et al. |
| 2002/0064881 A1 | 5/2002 | Devlin et al. |
| 2002/0098598 A1 | 7/2002 | Coffen et al. |
| 2002/0099571 A1 | 7/2002 | Waku et al. |
| 2002/0106314 A1 | 8/2002 | Pelrine et al. |
| 2002/0116132 A1 | 8/2002 | Rhett et al. |
| 2002/0150450 A1 | 10/2002 | Bevirt et al. |
| 2002/0176865 A1 * | 11/2002 | Lucas et al. ............... 424/185.1 |
| 2003/0027342 A1 | 2/2003 | Sheridan et al. |
| 2003/0028501 A1 | 2/2003 | Balaban et al. |
| 2003/0047616 A1 | 3/2003 | Mase et al. |
| 2003/0050794 A1 | 3/2003 | Keck |
| 2003/0059764 A1 | 3/2003 | Ravkin et al. |
| 2003/0074223 A1 | 4/2003 | Hickle et al. |
| 2003/0099580 A1 | 5/2003 | Pressman et al. |
| 2003/0104503 A1 * | 6/2003 | Sullivan et al. ............... 435/7.92 |
| 2003/0110178 A1 | 6/2003 | Woods et al. |
| 2003/0120633 A1 * | 6/2003 | Torre-Bueno ............... 707/1 |
| 2003/0154105 A1 | 8/2003 | Ferguson |
| 2003/0163031 A1 | 8/2003 | Madden et al. |
| 2003/0179445 A1 | 9/2003 | Maenle et al. |
| 2003/0183683 A1 | 10/2003 | Stewart |
| 2003/0203493 A1 | 10/2003 | Lemme et al. |
| 2003/0211630 A1 | 11/2003 | Richards et al. |
| 2003/0215936 A1 | 11/2003 | Kallioniemi et al. |
| 2003/0225477 A1 | 12/2003 | Gilman et al. |
| 2004/0023320 A1 | 2/2004 | Steiner et al. |
| 2004/0027462 A1 | 2/2004 | Hing |
| 2004/0033501 A1 | 2/2004 | Lappe et al. |
| 2004/0039607 A1 | 2/2004 | Savitz et al. |
| 2004/0098206 A1 | 5/2004 | Milliken et al. |
| 2004/0117571 A1 | 6/2004 | Chang et al. |
| 2004/0219069 A1 | 11/2004 | Kalra et al. |
| 2004/0228766 A1 | 11/2004 | Witty et al. |
| 2004/0243444 A1 | 12/2004 | Steusloff et al. |
| 2004/0253662 A1 | 12/2004 | Heid et al. |
| 2004/0259111 A1 | 12/2004 | Marlowe et al. |
| 2004/0266015 A1 | 12/2004 | Favuzzi et al. |
| 2004/0267562 A1 | 12/2004 | Fuhrer et al. |
| 2005/0026148 A1 | 2/2005 | Rexhausen et al. |
| 2005/0026181 A1 | 2/2005 | Davis et al. |
| 2005/0037406 A1 | 2/2005 | De La Torre-Bueno et al. |
| 2005/0038676 A1 | 2/2005 | Showalter et al. |
| 2005/0054083 A1 | 3/2005 | Vuong et al. |
| 2005/0059155 A1 | 3/2005 | Graupner et al. |
| 2005/0060188 A1 | 3/2005 | Valley |
| 2005/0064535 A1 | 3/2005 | Favuzzi et al. |
| 2005/0075544 A1 | 4/2005 | Shapiro et al. |
| 2005/0096869 A1 | 5/2005 | Drager et al. |
| 2005/0123181 A1 | 6/2005 | Freund et al. |
| 2005/0136509 A1 | 6/2005 | Gholap et al. |
| 2005/0158212 A1 | 7/2005 | Yavilevich |
| 2005/0159982 A1 | 7/2005 | Showalter et al. |
| 2005/0165625 A1 | 7/2005 | Ladic et al. |
| 2005/0191214 A1 | 9/2005 | Tseung et al. |
| 2005/0250211 A1 | 11/2005 | Reinhardt et al. |
| 2005/0273272 A1 | 12/2005 | Brando et al. |
| 2005/0280574 A1 | 12/2005 | Tafas et al. |
| 2006/0029519 A1 | 2/2006 | Nakaya et al. |
| 2006/0084088 A1 | 4/2006 | Schultz et al. |
| 2006/0085140 A1 | 4/2006 | Feingold et al. |
| 2006/0088940 A1 | 4/2006 | Feingold et al. |
| 2006/0099567 A1 | 5/2006 | Muller-Cohn et al. |
| 2006/0105359 A1 | 5/2006 | Favuzzi et al. |

(56) References Cited

U.S. PATENT DOCUMENTS

| | | |
|---|---|---|
| 2006/0148063 A1 | 7/2006 | Fauzzi et al. |
| 2006/0178776 A1 | 8/2006 | Feingold et al. |
| 2006/0178833 A1 | 8/2006 | Bauer et al. |
| 2006/0190185 A1 | 8/2006 | Ford et al. |
| 2006/0199169 A1 | 9/2006 | Lam et al. |
| 2006/0210432 A1 | 9/2006 | Victor |
| 2006/0239867 A1 | 10/2006 | Schaeffer |
| 2006/0257013 A1 | 11/2006 | Ramm et al. |
| 2006/0265133 A1 | 11/2006 | Cocks et al. |
| 2007/0005169 A1 | 1/2007 | Röhnert et al. |
| 2007/0010911 A1 | 1/2007 | Feingold et al. |
| 2007/0010912 A1 | 1/2007 | Feingold et al. |
| 2007/0029342 A1 | 2/2007 | Cross et al. |
| 2007/0053794 A1 | 3/2007 | Perez et al. |
| 2007/0112804 A1 | 5/2007 | DeSimas et al. |
| 2007/0122797 A1 | 5/2007 | De La Torre-Bueno |
| 2007/0124082 A1 | 5/2007 | De La Torre-Bueno |
| 2007/0124084 A1 | 5/2007 | De La Torre-Bueno |
| 2007/0159688 A1 | 7/2007 | Descour et al. |
| 2007/0172100 A1 | 7/2007 | Lefebvre |
| 2007/0196909 A1 | 8/2007 | Showalter et al. |
| 2007/0207490 A1 | 9/2007 | Benfield et al. |
| 2007/0208534 A1 | 9/2007 | Benfield et al. |
| 2007/0217949 A1 | 9/2007 | Mimura et al. |
| 2007/0224699 A1 | 9/2007 | Gates |
| 2007/0245184 A1 | 10/2007 | Benfield et al. |
| 2007/0254277 A1 | 11/2007 | Scrabeck et al. |
| 2008/0006653 A1 | 1/2008 | Dai et al. |
| 2008/0024301 A1 | 1/2008 | Fritchie et al. |
| 2008/0235055 A1* | 9/2008 | Mattingly et al. ............... 705/3 |
| 2008/0307117 A1 | 12/2008 | Muller-Cohn et al. |
| 2009/0155838 A1 | 6/2009 | Hale |
| 2009/0177427 A1 | 7/2009 | Bauer et al. |
| 2009/0254572 A1 | 10/2009 | Redlich et al. |
| 2009/0291427 A1 | 11/2009 | Muller-Cohn et al. |
| 2009/0298132 A1 | 12/2009 | Muller-Cohn et al. |
| 2010/0009460 A1 | 1/2010 | Clark et al. |
| 2010/0021352 A1 | 1/2010 | Trueeb et al. |
| 2010/0063847 A1 | 3/2010 | Eisenberg et al. |
| 2010/0070305 A1 | 3/2010 | Eisenberg et al. |
| 2010/0113288 A1 | 5/2010 | Adey et al. |
| 2010/0123551 A1 | 5/2010 | Fritchie |
| 2010/0126286 A1 | 5/2010 | Self et al. |
| 2010/0167334 A1 | 7/2010 | Williamson, IV |
| 2010/0217620 A1 | 8/2010 | Kippenhan et al. |
| 2011/0047092 A1 | 2/2011 | Taylor |
| 2011/0115610 A1 | 5/2011 | Hughes |

FOREIGN PATENT DOCUMENTS

| | | |
|---|---|---|
| CA | 2688530 | 12/2008 |
| CA | 2699386 | 3/2009 |
| CN | 2881785 Y | 3/2007 |
| DE | 197 41 385 A1 | 4/1998 |
| DE | 199 05 490 A1 | 8/2000 |
| EP | 0 417 006 A2 | 3/1991 |
| EP | 0 424 692 A1 | 5/1991 |
| EP | 1 004 359 A2 | 5/2000 |
| EP | 1 130 377 A1 | 9/2001 |
| EP | 1 190 771 A1 | 3/2002 |
| EP | 1 245 395 A2 | 10/2002 |
| GB | 2475835 A | 6/2011 |
| JP | 54136389 | 10/1979 |
| JP | 63236966 | 10/1988 |
| JP | 4110752 A | 4/1992 |
| JP | 4184170 A | 7/1992 |
| JP | 6094706 A | 4/1994 |
| JP | 6130069 | 5/1994 |
| JP | 07-085085 | 3/1995 |
| JP | 10-260116 | 9/1998 |
| JP | 11306271 | 11/1999 |
| JP | 200000975 | 1/2000 |
| JP | 2000065842 | 3/2000 |
| JP | 2002-117143 | 4/2002 |
| JP | 2002-119577 | 4/2002 |
| JP | 2002-123631 | 4/2002 |
| JP | 2002132961 | 5/2002 |
| JP | 2002-207824 | 7/2002 |
| JP | 2002-312361 A | 10/2002 |
| JP | 2003-279582 | 10/2003 |
| JP | 2003-315347 A | 11/2003 |
| JP | 2003-329690 | 11/2003 |
| JP | 2005-182507 A | 7/2005 |
| JP | 2006-099567 A | 4/2006 |
| JP | 2008-507029 A | 3/2008 |
| JP | 2010-217042 A | 9/2010 |
| SU | 1238173 A2 | 9/1984 |
| SU | 1153369 A | 4/1985 |
| WO | WO 94/11838 A1 | 5/1994 |
| WO | WO 94/15270 A1 | 7/1994 |
| WO | WO 94/22580 | 10/1994 |
| WO | WO 97/39888 | 10/1997 |
| WO | WO 99/28724 | 6/1999 |
| WO | WO 99/30167 A1 | 6/1999 |
| WO | WO 99/43855 A1 | 9/1999 |
| WO | WO 99/44743 | 9/1999 |
| WO | WO 00/13588 | 3/2000 |
| WO | WO 00/15021 | 3/2000 |
| WO | WO 00/19897 | 4/2000 |
| WO | WO 00/51058 | 8/2000 |
| WO | WO 00/62035 | 10/2000 |
| WO | WO 00/79408 A2 | 12/2000 |
| WO | WO 01/08040 A1 | 2/2001 |
| WO | WO 01/20532 A2 | 3/2001 |
| WO | WO 01/31333 A1 | 5/2001 |
| WO | WO01/94016 A1 | 12/2001 |
| WO | WO 02/056121 A2 | 7/2002 |
| WO | WO 03/042788 A2 | 5/2003 |
| WO | WO 2004/057307 A1 | 7/2004 |
| WO | WO 2004/057308 A1 | 7/2004 |
| WO | WO 2004/058404 A2 | 7/2004 |
| WO | WO 2004/058950 A1 | 7/2004 |
| WO | WO 2004/059284 A2 | 7/2004 |
| WO | WO 2004/059287 A2 | 7/2004 |
| WO | WO 2004/059288 A2 | 7/2004 |
| WO | WO 2004/059297 A1 | 7/2004 |
| WO | WO 2004/059441 A2 | 7/2004 |
| WO | WO 2005/084263 A2 | 9/2005 |
| WO | WO 2005/093641 A1 | 10/2005 |
| WO | WO 2005/098455 A1 | 10/2005 |
| WO | WO 2005/100948 A1 | 10/2005 |
| WO | 2006/019392 A1 | 2/2006 |
| WO | WO 2006/060125 A2 | 6/2006 |
| WO | WO 2006/118888 A1 | 11/2006 |
| WO | WO 2006/119585 A1 | 11/2006 |
| WO | WO 2006/130760 A2 | 12/2006 |
| WO | 2007/123879 A2 | 11/2007 |
| WO | 2008/156566 A1 | 12/2008 |
| WO | 2011/063139 A1 | 5/2011 |

OTHER PUBLICATIONS

Luciuk, Rodney; Winkleman, Gary E.; Sluser, Mark; Taylor, Patrick A.; Ens, Arnie M, *A laboratory information management system for small to medium sized soil, plant and water testing laboratories*, 2000, vol. 31, No. 11-14, Swift Current, Saskatchewan, Canada, pp. 1965-1972.

Petcher, D.; Lockhart, E.; Firman, R.; Chen, J.; Johnstone, R.; Chaplin, E., *Robotic System for Handling Infectious Clinical and Pre-Clinical Serum Samples*, Dec. 1999, vol. 4, No. 6, Kenilworth, NJ, USA, pp. 68-75.

Farnsworth, Ralph E., *Laboratory Automatic Storage and Retrieval*, 1997, vol. 9, No. 3, Cincinnati, OH, USA, pp. 129-134.

Ferguson, R.L.; Hwang, H.L.; Bishop, C.P.; Blair, R.L.; Cornett, R.L., *BIOPLUS: An eclectic laboratory information management system for the ORNL Radiobioassay Laboratory*, 1992, Washington, D.C., USA, pp. 1-22.

Bailey, Jeffrey, et al., *The Use of Reflexive Rules in a Laboratory Information System to Document Resident Training in Special Coagulation Testing*, Abstract from *Advancing Practice, Instruction, and Innovation Through Informalities (APIII 2007) Conference*, Cleveland, Ohio, Sep. 9-12, 2007, 1 Page.

(56) References Cited

OTHER PUBLICATIONS

Floyd, Alton PhD, et al., *Process Control for Standardization of Multiple-Step Staining Methods*, Abstract from *Advancing Practice, Instruction, and Innovation Through Informalities (APIII 2007) Conference*, Miami, Florida, Sep. 9-12, 2007, 1 Page.

Grimm, Erin MD, et al., *Efficiency and Quality in Pathology-Slide Tracking*, Abstract from *Advancing Practice, Instruction, and Innovation Through Informalities (APIII 2007) Conference*, Seattle, Washington, Sep. 9-12, 2007, 2 Pages.

Grimm, Erin MD, et al., *Quality and Efficiency in Pathology-Photography*, Abstract from *Advancing Practice, Instruction, and Innovation Through Informalities (APIII 2007) Conference*, Seattle, Washington, Sep. 9-12, 2007, 1 Page.

Brugal, Gerard, et al., *HOME: Highly Optimized Microscope Environment*, 1992 Wiley-Liss, Inc., Cytometry 13: pp. 109-116.

Krief, Bruno, et al., *IMPACT: Integrating Microscopy for Pathology Activities and Computer Technology*, 1993 IEEE, pp. 76-79.

Schmidt, Rodney A., et al., *Integration of Scanned Document Management with the Anatomic Pathology Laboratory Information System*, American Society for Clinical Pathology Am J Clin Pathol 2006: 126: pp. 678-683.

*MISYS Laboratory—SMART, Specimen Management, Routing, and Tracking*, Copyright 2002, 2 Pages.

Brugal, Gerard, et al., *HOME Highly Optimized Microscope Environment*, Advances in Medical Informatics, IOS Press, 1992, pp. 161-163.

Botsman, N.E., et al., *Accelerated Method of Histological Specimen Preparation Using Ultrasound*, 7/I 1967, 6 Pages, English Translation 4 Pages.

"CAE Specification: DCE 1.1 Remote Procedure Call: Document No. C706," section entitled "Universal Unique Identifier" by the Open Group of Berkshire, UK (1997), 13 pgs.

U.S. Appl. No. 09/571,989, filed May 16, 2000, Druyer-Sanchez et al.

Decision of Rejection issued by the State Intellectual Property Office of the People's Republic of China, dated Jan. 14, 2013.

Supplemental European Search Report dated Jun. 1, 2012.

Japanese Office Action dated Feb. 19, 2013.

Japanese Office Action dated Jan. 28, 2014.

\* cited by examiner

1220

LABORATORY INSTRUMENTATION INFORMATION MANAGEMENT AND CONTROL NETWORK

CROSS REFERENCE TO RELATED APPLICATIONS

This application is a continuation of U.S. patent application Ser. No. 11/032,324, filed Jan. 10, 2005, which is a continuation-in-part of U.S. patent application Ser. No. 10/893,725, filed Jul. 16, 2004, which claims benefit of U.S. Provisional Application No. 60/487,998, filed Jul. 17, 2003, all of which are incorporated by reference herein.

BACKGROUND OF THE INVENTION

1. Technical Field

This invention relates generally to data management and more particularly to communicating, managing, brokering and facilitating the replication of data over a system of instruments, computers and interfaces for managing laboratory information.

2. Description of Related Art

In order to correctly diagnose or confirm the presence of disease in a patient, a physician typically must excise a sample of diseased tissue and have that tissue examined on a microscopic level by a pathologist. Using a plurality of analysis techniques and laboratory instruments, the pathologist will be able to analyze the diseased tissue to identify any structural (or other) changes in cell tissues and organs. In most cases, the pathologist may be able to 1) identify the type of disease, 2) establish a prognosis on the likely progression of the disease, and 3) make a determination as to what therapy might be most effective in curing or treating the disease. As with most diseases, one important element to a successful treatment or cure is the ability of the physician to rapidly and effectively treat the patient before the disease progresses to an incurable state. This requires that the pathologist have the ability to rapidly analyze the tissue sample, diagnose the condition and disseminate this information to the patient's physician, all the while maintaining accuracy and reliability.

Laboratory Information Systems (LIS) are known for management of patient and laboratory information. Such systems typically consist of a server or host computer, a data base and data base management system, and application software for receiving and processing patient information. Known LIS may be "web-enabled" to facilitate access of the system and information over the Internet.

Unfortunately, however, current Laboratory Information Systems tend to lack the ability to manage workflow with certain laboratory instrumentation, such as, for example, an advanced staining instrument. This management includes basic connectivity, data exchange capability and business rules implemented to optimize workflow, costs and efficiencies. As such, there exist several deficiencies in how these instruments are utilized in the laboratory. A significant amount of time and energy is expended replicating tedious functions, such as data entry, labeling and manual entry for report generation. This replication increases the amount of time it takes to process samples by creating a significant bottleneck in laboratory work flow. The tedious nature of these tasks can substantially increase errors and can affect the accuracy of the diagnostic process. The resulting increase in test completion time may allow a localized disease to progress into systemic proportions, such as a localized tumor metastasizing, having a devastating effect on patient prognosis and/or treatment options and results.

One example of how a bottleneck in laboratory work flow may occur is illustrated in FIG. 1. Typically, a pathologist receives a sample for testing, and orders tests 10. Upon receipt of a tissue sample, accessioning and test order information is entered into the LIS by a laboratory technician 12. However, because the LIS is not connected to the laboratory instruments, the accessioning and test order information that was just entered into the LIS needs to be sent to the test laboratory 14 and re-entered into each laboratory instrument that will be used for testing in order to create slide labels 16. This could take a significant amount of time depending on the number of samples and the extent of testing being performed on the samples. Additionally, each time this data entry function is replicated, the possibility of error in the information transfer increases, reducing the accuracy and reliability of the testing procedure.

Another example of how a bottleneck in laboratory work flow may occur is described as illustrated in FIG. 2 and involves the generation of a status report. Again, the pathologist receives the test sample and orders tests 18. Accessioning and test ordering information is entered into the LIS 20, and then such information must be sent to the test lab 22. Then accessioning and test order information has to be entered into a laboratory instrument 24, such as an advanced staining instrument, and a slide label is generated and the laboratory instrument will begin performing the ordered test. In some cases, the pathologist, lab manager and technician may be keenly interested in the progress of the test and thus may desire to monitor the status of the test. Unfortunately however, the lack of data communications between the LIS and the laboratory instruments prevents test status monitoring by precluding the automatic generation of a test status report. As such, in order to check the status of the test the testing must be interrupted 26 and a test status report must be manually generated.

In addition to this lack of connectivity creating a bottleneck in laboratory work flow, the diagnostic capability of the laboratory is also adversely affected due to the reality that current laboratory set-ups do not have the ability to perform many new and advanced features which may substantially increase the timeliness, reliability and accuracy of new and existing tests.

One way to maximize the timeliness, reliability and accuracy of the sample analysis, condition diagnosis and dissemination of information would be to establish a communication connection between the LIS and the laboratory instrumentation. The extent to which the work flow bottleneck or the performance efficiency would be improved thus would be dependent upon the type of connectivity (unidirectional or bidirectional) established between the LIS and the laboratory instrumentation. For example, a unidirectional, or one-way, connection between the LIS and the laboratory instrumentation would allow for test result information to flow, in one direction, between the laboratory instrument and the LIS, thus eliminating duplicate data entry. Similarly, a bidirectional, or two-way, connection between the LIS and the medical laboratory instrumentation would enable new advanced features to be included, such as order entry and tracking, status updates, sample tracking, quality control, College of American Pathologists (CAP) compliance, inventory management and maintenance, all of which would increase performance time, reliability and accuracy.

Unfortunately however, a suitable system management structure does not exist that would allow for effective control between the LIS and automated laboratory instrumentation, such as staining instrumentation, such that the timeliness of the test performance, data analysis, disease diagnosis and information dissemination process is substantially optimized. Additionally, known systems for interconnecting laboratory instrumentation and information systems do not effectively and automatically identify, prioritize and stage specimens to optimize the throughput and utilization of the automatic staining systems. Nor do known systems have the capability to automate the identification, labeling and tracking of specimens and results through the clinical pathology process. Furthermore, known systems are not specifically capable of optimizing the storage, use, and management of the reagents between staining systems necessary for performing the multitude of staining procedures for disease diagnosis.

SUMMARY OF THE INVENTION

In accordance with one aspect of the invention is a method for configuring a host controlling at least one instrument in a laboratory comprising: configuring said host to have at least one local data element; and configuring said host to have at least one global data element, said at least one global data element having a common data definition and data value used by said host and at least one other host connected to said host, said at least one local data element having a data definition and data value used only by said host, at least one of said data elements being used by said host in connection with processing performed by said at least one instrument. The host and the at least one other host may communicate with an interface server to maintain an up-to-date local copy of said at least one global data element. The method may also include: configuring one local data element of said host as a new global data element; communicating said new global data element to said interface server; and configuring said at least one other host in accordance with said new global data element using said interface server. The host, said at least one other host and said interface server may be included in a laboratory network. The interface server may be connected to a laboratory information system. The laboratory instrument may be an anatomical pathology laboratory instrument. The host may perform offline processing with respect to said at least one other host and said interface server, and said host may use said at least one local data element in said offline processing with said at least one instrument. The host may synchronize said at least one global data element with said interface server when said host completes said offline processing, said host and said at least one other host being configured to use different global data elements. The data elements may include at least one of: a user password, a user privilege, reagent information, patient information, sample information, batch information, laboratory test information and a protocol. The at least one global data element may include a first global data element for a reagent, a first instrument of said at least one instruments using said reagent, said host being an owner of said reagent, and the method may further comprise: sending a request from a second host connected to said host requesting that said host transfer ownership of said reagent to said second host; sending a response by said host to said second host, said response denying said request by said host if said reagent is in use by said first instrument, and otherwise said response granting said request and transferring ownership of said reagent to said first host; and sending, by said first host, new ownership information to an interface server which maintains a database of global data elements, the database of global data elements including at least one data element for the new ownership information and including said at least one global data element. The reagent may be physically relocated from said first instrument controlled by said host to a second instrument controlled by said second host when said second host is identified as having ownership of said reagent. Information may be communicated between said laboratory information system and said interface server, said information comprising a first portion and a second portion, said first portion including at least one of test order information and case information sent from said laboratory information system to said interface server, said second portion including status information about a test order. The first portion may include case information that is manually entered at said laboratory information system and is communicated from said laboratory information system without further manual data entry. The first portion may include test order information and the method may further comprise: communicating test result information from said host to said interface server for a test performed by a first instrument of said at least one laboratory instruments; and sending said second portion from said interface server to said laboratory information system, said second portion including status information corresponding to said test result information. The interface server may manage a database including information about test orders that have not been completed, and, when a test order is complete, information about said test order may be removed from said database. The host may include a local database of information about tests performed by said first instrument, and the method may further comprise: receiving a request for test information about a completed test performed by said first instrument; requesting said test information from said local database of said host about said completed test; and sending a response to said request, said response including data in accordance with said test information. An update to said at least one global data element may be automatically replicated to said host and said at least one other host in accordance with ongoing processing performed by each host to obtain data updates from a server managing a database of global data elements. The at least one global data element may be a configuration data element having a corresponding configuration option. The configuration option may be for a configurable symbology identifier corresponding to a symbology used with optical encodings in the laboratory. One of said instruments controlled by said host may operate in accordance with said symbology. An optical scanner may be one of said instruments controlled by said host, said scanner supporting scanning operations in accordance with said symbology. A label printer may be one of said instruments controlled by said host, said label printer supporting printing operations in accordance with said symbology. The symbology may be used with bar code labels associated with elements used in connection with processing within the laboratory. The elements may include at least one of: a sample, a specimen, and a reagent. The symbology may be of a multiple dimension. A bar code label may encode an identifier used to obtain data from a database about an element associated with said bar code label, said data including at least one of said data elements. The host may be configured to identify an element in a laboratory, and the method may further comprise: receiving, by a label associated with said element, an interrogator signal; and transmitting, by said label in response to said interrogator signal, an electromagnetic response signal including at least a first portion of information used for uniquely identifying said element in said laboratory. The electromagnetic response signal may be produced using information encoded in said label associated with said element. The label may be one of a radio frequency identification label or an infrared identification label. The label may be a radio frequency identification label and said element may be one of a sample, a specimen, or a reagent. Information may be encoded in said radio frequency identification label and may include at least one of patient information, test information, and batch information used to identify at least one other element and said element from a same batch. Information may be read from said radio frequency identification label. Information may be written to said radio frequency identification label. The information may include test information about at least one test performed in an anatomical pathology laboratory. The element may be sample and the method may also comprise: reading said test information from said radio frequency identification label in connection with a test to be performed as a step in laboratory processing prior to performing said test for verification that said step is to be performed. The method may also include: encoding said radio frequency identification label with additional information about said test, said additional information including at least one of: time, date, test parameters, filename, and test results. The filename may identify an image file. The method may also include: reading at least a portion of said additional information; determining a diagnosis in accordance with said portion; and encoding said radio frequency identification label with data about said diagnosis. The information may include batch information, and the method may further comprise: determining a plurality of elements belonging to a same group in accordance with said batch information encoded on radio frequency identification labels of said plurality of elements. The method may also include: determining a location of said element in said laboratory in accordance with said electromagnetic response signal. The label may be affixed to a surface of said element. The label may be embedded in said element. The label may include other information imprinted on a surface of said label. The other information may include optically recognizable data which is readable by a machine. The other information may include human readable data. The method may also include: encoding said label with other information as said element is processed in accordance with at least one laboratory workflow processing step. The other information may include a bar code with an identifier uniquely identifying said element. The element may be a reagent and the method may also include: encoding said label with other information regarding amounts of said reagent used in connection with laboratory processing. The method may further comprise: determining when to reorder said reagent in accordance with said other information. Ownership of said reagent by an instrument in said laboratory may be determined in accordance with information encoded in said label. The method may also include: using said first portion to obtain additional information about said element from a database. The hosts, an interface server, and a laboratory information system may be included in a laboratory network, said laboratory information system may be in communication with said interface server, and said interface server may be in communication with said host, and wherein one of said instruments controlled by said host may be a printer, and the host may be configured to automatically print slide labels in response to said interface server receiving an order from a laboratory information system.

In accordance with another aspect of the invention is a method for automatically determining a processing order of a plurality of samples in a laboratory comprising: receiving scheduling inputs, said scheduling inputs including current supply information; and determining a processing order for said plurality of samples in accordance with scheduling inputs on at least one laboratory instrument. The current supply information may include reagent supply information and reagent ownership information. The scheduling inputs may include laboratory configuration information associated with said at least one laboratory instrument, said laboratory configuration information comprising at least one of: instrument processing capacity, instrument status information, and instrument processing rates. The scheduling inputs may include quality control information comprising at least one of a number of positive quality control samples, a number of negative quality control samples. The quality control information may be determined in accordance with at least one certification criteria for a new reagent. The processing order may schedule processing for a plurality of laboratory instruments. The processing order may schedule processing for a plurality of sequentially dependent runs. The scheduling inputs may include at least one of: preferred slide groupings, processing prioritization information, processing dependencies, case information for pending testing orders, and performance selection criteria. The performance selection criteria may include maximizing throughput. The scheduling inputs may include at least one of a sample run configuration and configuration override information, and the method may further comprise: determining an output state in accordance with at least one of said sample run configuration and said configuration override information. The configuration override information may include a variation of a current configuration.

In accordance with another aspect of the invention is a system for laboratory information management and control comprising: a laboratory information system managing patient and laboratory information; a first host configured with a local data element and configured to share a global data element, said local data element having a data definition and data value used only by said first host, said host using at least one of said data elements in connection with performing processing on at least one laboratory instrument connected to said first host; a second host configured to share said global data element; at least one laboratory instrument controlled by said host; and a server in communication with said laboratory information system and said at least one host, said server managing a database including said global data element, said server communicating with said first host and said second host to maintain a current copy of said global data element in said database, and in local copies of said global data element at each of said hosts.

In accordance with another aspect of the invention is a computer program product for configuring a host controlling at least one instrument in a laboratory comprising code that: configures said host to have at least one local data element; and configures said host to have at least one global data element, said at least one global data element having a common data definition and data value used by said host and at least one other host connected to said host, said at least one local data element having a data definition and data value used only by said host, at least one of said data elements being used by said host in connection with processing performed by said at least one instrument. The host and said at least one other host may communicate with an interface server to maintain an up-to-date local copy of said at least one global data element. The computer program product may also include code that: configures one local data element of said host as a new global data element; communicates said new global data element to said interface server; and configures said at least one other host in accordance with said new global data element using said interface server. The host, said at least one other host and said interface server may be included in a laboratory network. The interface server may be connected to a laboratory information system. The laboratory instrument may be an anatomical pathology laboratory instrument. The host may perform offline processing with respect to said at least one other host and said interface server, and said host may use said at least one local data element in said offline processing with said at least one instrument. The host may synchronize said at least one global data element with said interface server when said host completes said offline processing, said host and said at least one other host being configured to use different global data elements. The data elements may include at least one of: a user password, a user privilege, reagent information, patient information, sample information, batch information, laboratory test information and a protocol. The at least one global data element may include a first global data element for a reagent, a first instrument of said at least one instruments using said reagent, said host being an owner of said reagent, and the computer program product may further comprise code that: sends a request from a second host connected to said host requesting that said host transfer ownership of said reagent to said second host; sends a response by said host to said second host, said response denying said request by said host if said reagent is in use by said first instrument, and otherwise said response granting said request and transferring ownership of said reagent to said first host; and sends, by said first host, new ownership information to an interface server which maintains a database of global data elements, the database of global data elements including at least one data element for the new ownership information and including said at least one global data element. The reagent may be physically relocated from said first instrument controlled by said host to a second instrument controlled by said second host when said second host is identified as having ownership of said reagent. Information may be communicated between said laboratory information system and said interface server, said information comprising a first portion and a second portion, said first portion including at least one of test order information and case information sent from said laboratory information system to said interface server, said second portion including status information about a test order. The first portion may include case information that is manually entered at said laboratory information system and is communicated from said laboratory information system without further manual data entry. The first portion may include test order information and the computer program product may further comprise code that: communicates test result information from said host to said interface server for a test performed by a first instrument of said at least one laboratory instruments; and sends said second portion from said interface server to said laboratory information system, said second portion including status information corresponding to said test result information. The interface server may manage a database including information about test orders that have not been completed, and, when a test order is complete, information about said test order may be removed from said database. The host may include a local database of information about tests performed by said first instrument, and the computer program product may further comprise code that: receives a request for test information about a completed test performed by said first instrument; requests said test information from said local database of said host about said completed test; and sends a response to said request, said response including data in accordance with said test information. An update to said at least one global data element may be automatically replicated to said host and said at least one other host in accordance with ongoing processing performed by each host to obtain data updates from a server managing a database of global data elements. At least one global data element may be a configuration data element having a corresponding configuration option. The configuration option may be for a configurable symbology identifier corresponding to a symbology used with optical encodings in the laboratory. One of the instruments controlled by the host may operate in accordance with said symbology. An optical scanner may be one of said instruments controlled by said host, said scanner supporting scanning operations in accordance with said symbology. A label printer may be one of said instruments controlled by said host, said label printer supporting printing operations in accordance with said symbology. The symbology may be used with bar code labels associated with elements used in connection with processing within the laboratory. The elements may include at least one of: a sample, a specimen, and a reagent. The symbology may be of a multiple dimension. A bar code label may encode an identifier used to obtain data from a database about an element associated with said bar code label, said data including at least one of said data elements. The host may be configured to identify an element in a laboratory, and the computer program product may further comprise code that: receives, by a label associated with said element, an interrogator signal; and transmits, by said label in response to said interrogator signal, an electromagnetic response signal to said host and the electromagnetic response signal includes at least a first portion of information used for uniquely identifying said element in said laboratory. The electromagnetic response signal may be produced using information encoded in said label associated with said element. The label may be one of a radio frequency identification label or an infrared identification label. The label may be a radio frequency identification label and said element may be one of a sample, a specimen, or a reagent. Information may be encoded in said radio frequency identification label and includes at least one of patient information, test information, and batch information used to identify at least one other element and said element from a same batch. Information may be read from said radio frequency identification label. Information may be written to said radio frequency identification label. The information may include test information about at least one test performed in an anatomical pathology laboratory. The element may be a sample, and the computer program product may further comprise: code that reads said test information from said radio frequency identification label in connection with a test to be performed as a step in laboratory processing prior to performing said test for verification that said step is to be performed. The computer program product may also include code that: encodes said radio frequency identification label with additional information about said test, said additional information including at least one of: time, date, test parameters, filename, and test results. The filename may identify an image file. The computer program product may also include code that: reads at least a portion of said additional information; determines a diagnosis in accordance with said portion; and encodes said radio frequency identification label with data about said diagnosis. The information may include batch information, and the computer program product may further comprise code that: determines a plurality of elements belonging to a same group in accordance with said batch information encoded on radio frequency identification labels of said plurality of elements. The computer program product may further comprise code that: determines a location of said element in said laboratory in accordance with said electromagnetic response signal. The label may be affixed to a surface of said element. The label may be embedded in said element. The label may include other information imprinted on a surface of said label. The other information may include optically recognizable data which is readable by a machine. The other information may include human readable data. The computer program product may further comprise code that: encodes said label with other information as said element is processed in accordance with at least one laboratory workflow processing step. The other information may include a bar code with an identifier uniquely identifying said element. The element may be a reagent and the computer program product may further comprise code that: encodes said label with other information regarding amounts of said reagent used in connection with laboratory processing. The computer program product may further include code that: determines when to reorder said reagent in accordance with said other information. Ownership of said reagent by an instrument in said laboratory may be determined in accordance with information encoded in said label. The computer program product may also include code that: uses said first portion to obtain additional information about said element from a database. The hosts, an interface server, and a laboratory information system may be included in a laboratory network, said laboratory information system may be in communication with said interface server, and said interface server may be in communication with said host, and wherein one of said instruments controlled by said host may be a printer, and the host may be configured to automatically print slide labels in response to said interface server receiving an order from a laboratory information system.

In accordance with another aspect of the invention is a computer program product for automatically determining a processing order of a plurality of samples in a laboratory comprising code that: receives scheduling inputs, said scheduling inputs including current supply information; and determines a processing order for said plurality of samples in accordance with scheduling inputs on at least one laboratory instrument. The current supply information may include reagent supply information and reagent ownership information. The scheduling inputs may include laboratory configuration information associated with said at least one laboratory instrument, said laboratory configuration information comprising at least one of: instrument processing capacity, instrument status information, and instrument processing rates. The scheduling inputs may include quality control information comprising at least one of a number of positive quality control samples, a number of negative quality control samples. The quality control information may be determined in accordance with at least one certification criteria for a new reagent. The processing order may be a schedule of processing for a plurality of laboratory instruments. The processing order may be a schedule of processing for a plurality of sequentially dependent runs. The scheduling inputs may include at least one of: preferred slide groupings, processing prioritization information, processing dependencies, case information for pending testing orders, and performance selection criteria. The performance selection criteria may include maximizing throughput. The scheduling inputs may include at least one of a sample run configuration and configuration override information, and the computer program product may further comprising code that: determines an output state in accordance with at least one of said sample run configuration and said configuration override information. The configuration override information may include a variation of a current configuration.

BRIEF DESCRIPTION OF DRAWINGS

The foregoing and other features and advantages of the present invention will be better understood from the following detailed description of illustrative embodiments, taken in conjunction with the accompanying drawings in which.

DETAILED DESCRIPTION OF VARIOUS EMBODIMENTS

Figure 1:
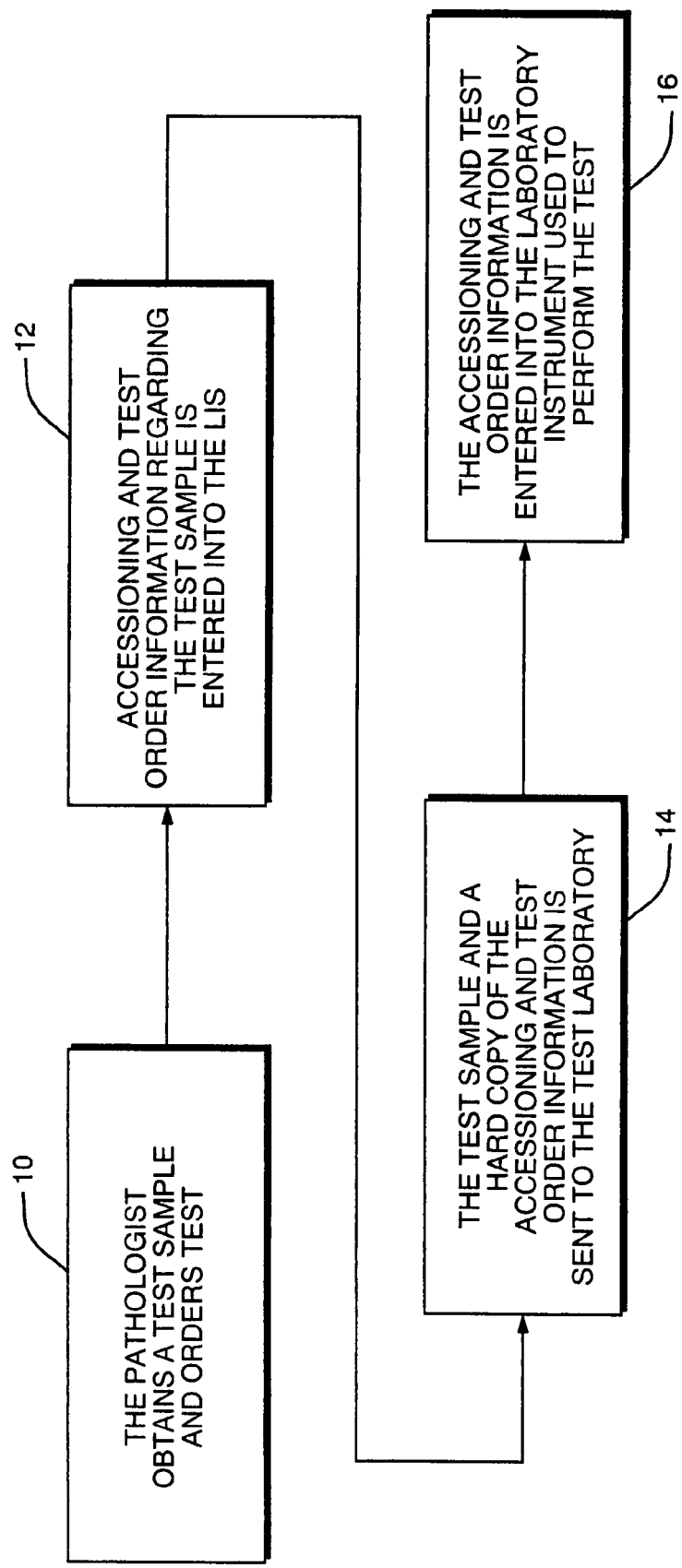
FIG. 1 is a block diagram illustrating a first type of bottleneck in laboratory work flow in accordance with the PRIOR ART.
Figure 2:
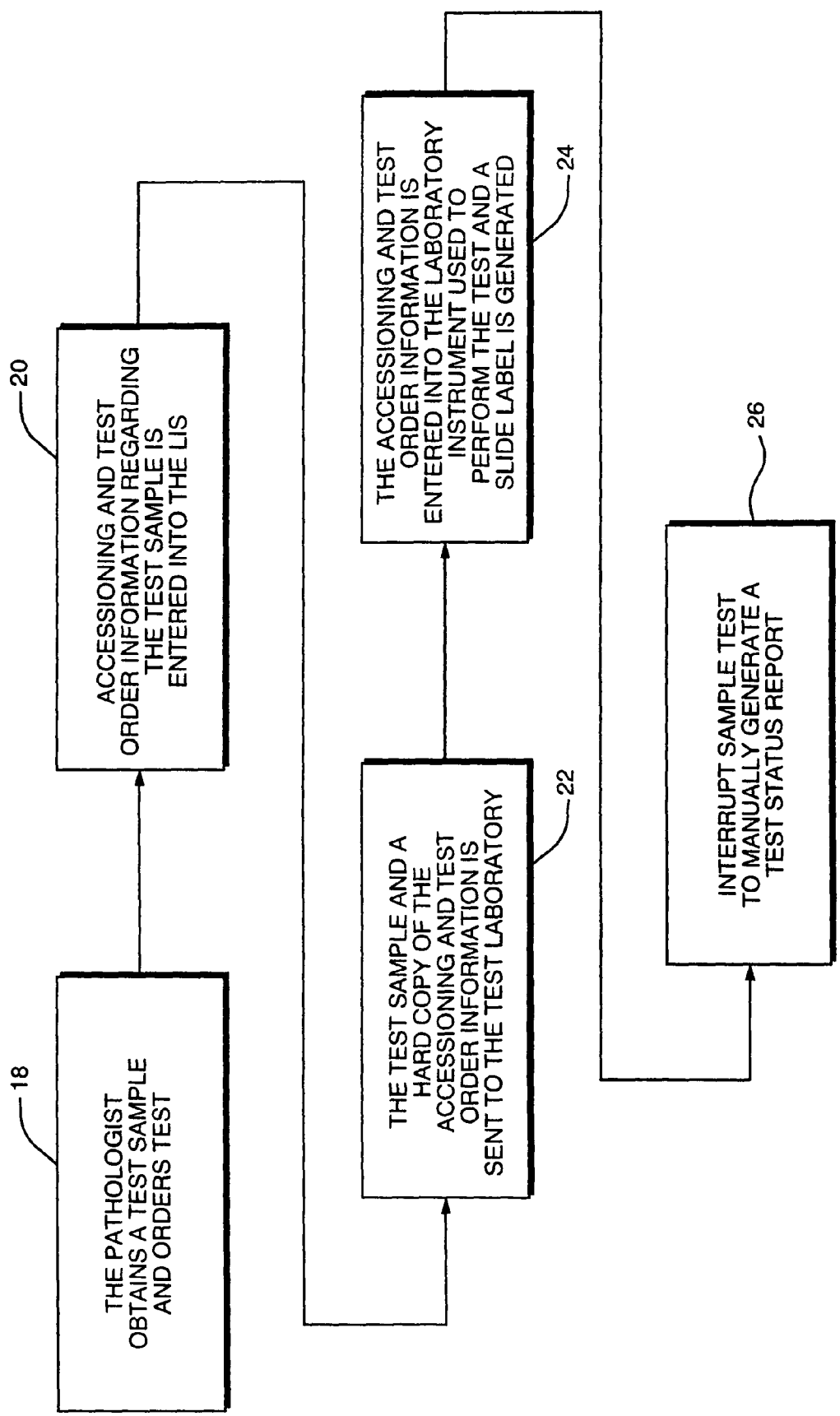
FIG. 2 is a block diagram illustrating a second type of bottleneck in laboratory work flow in accordance with the PRIOR ART.
Figure 3:
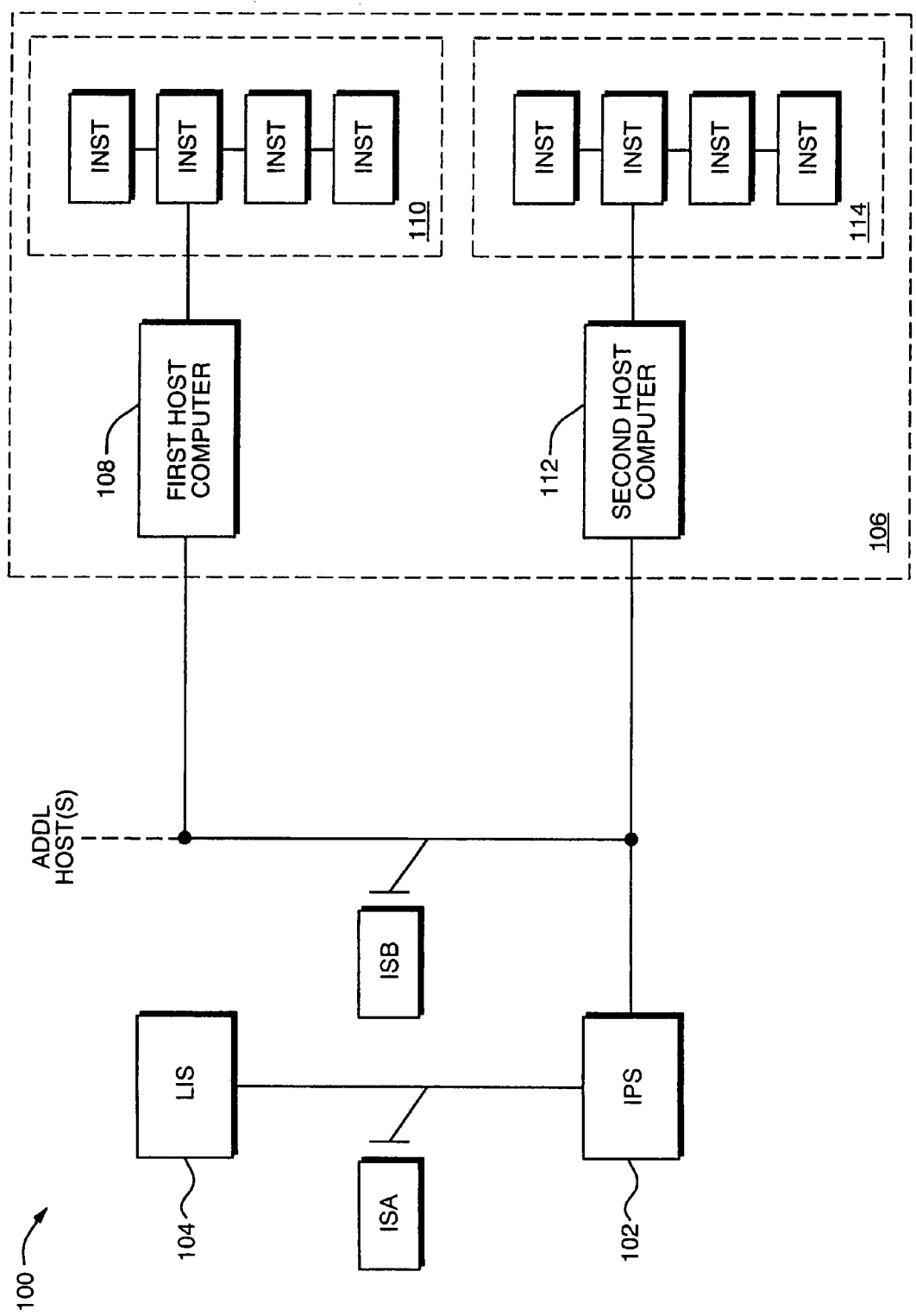
FIG. 3 is a block diagram of an illustrative embodiment of an interface point network (IPN)

Referring to FIG. 3, an Interface Point Network (according to an illustrative embodiment, IPN) 100 is provided and includes an Interface Point Server (IPS) 102 in communication with at least one hospital Laboratory Information System (LIS) 104 and a network of host computers 106. The network of host computers 106 includes a first host computer 108 communicated with a first plurality of laboratory instruments 110 and a second host computer 112 in communication with a second plurality of laboratory instruments 114. The host computer(s) may be interconnected with the laboratory instrumentation via known Ethernet connection or by other interconnectivity mechanisms known in the art, such as known serial or parallel connections or wireless connection. IPS 102 includes Interface Software B (referred to herein synonymously as "ISB" or "Ventana Lab Manager" or "VLM" software), that allows for the performance of automatic functions related to the management of data between network of host computers 106, such as the sharing of data elements between the first host computer 108 and second host computer 112 without difficulty or undesired data transmittal even if the first host computer 108 is one type of host computer and second host computer 112 is a different type of host computer. It should be noted that an embodiment may include an IPS configured without a connection to the LIS to aid in non-patient information between host computers.

The VLM software in the illustrative embodiment runs on the IPS 102. The main purpose of the VLM software is to facilitate the replication of data over a network between host systems. In an illustrative embodiment described herein the host systems are PCs interfaced to known automated slide staining apparatus such as available from Ventana Medical Systems of Tucson, Ariz. The data handled by the VLM can be of many types, such as staining protocols, bar code assignments, reagent dispenser information, reagent ID, reagent consumption, reagent ownership or registration with a particular instrument, user passwords, case data, Patient ID or name, institution, order requestor, accession ID, slide ID, operator ID, operator in-service status, operator quality control (QC) status, instrument QC status, inspection results, diagnosis results and/or staining results. VLM is a piece of software that resides on a PC connected to a network that can provide services to instrument 110, 114 host systems 108, 112. In this embodiment the VLM resides on the IPS 102, however it should be appreciated that the VLM software could reside on one or more of the hosts 108, 112 or be otherwise distributed in the network. Standard TCP/IP protocols are used to connect each instrument host computer with the VLM on the IPS 102. When the VLM software first comes online, it broadcasts a message to all devices on the network proclaiming its presence. If a host is configured to use VLM services, it can then connect with the VLM and request the latest data elements known to the VLM or it can share new data elements with the VLM, making them available to other host computers 108, 112. Typically, in a lab situation, such as in the illustrative embodiment, data sharing among automated slide staining instruments would include: staining protocols; user passwords and privileges; reagents (dispensers/vials); cases; keycodes; templates; panels; and $3^{rd}$ party reagents.

Each host 108, 112 can be independently set up to either share these data elements or not, depending on the individual lab and host requirements. If hosts are sharing data elements, there are algorithms in the software that evaluate which data is the most current, ensuring accurate data replication and avoiding data loss. The VLM initially builds and then holds a copy of the latest data elements being shared by all sharing hosts. It does this with close cooperation of the software in the host systems, which form a partnership with the VLM to make the complete system. Some data elements, most notably reagents, require ownership rights by the host system they are being used on. There is a software messaging system that permits one host to request a transfer of ownership from another host, thereby ensuring that reagent data elements get properly and safely changed (i.e. dispensed amount does not exceed container limits). The architecture of the VLM communication protocol allows a host to continue processing tissue with an owned reagent while the network connection is unavailable. The host may then synchronize with the VLM once a network connection is re-established.

The VLM software can manage data from a disparate group of host computers automatically. For instance, Ventana Medical Systems' NexES, HVS and NeuVision hosts can all share data elements between like systems without difficulty or undesired data transmittal from one host type to another. Data element storage and sharing, as described hereinafter, is implemented in the VLM software that allows for new types of hosts, previously unknown to the VLM, to share new types of data elements using the VLM without requiring software upgrades to the VLM system software. This permits host software to be upgraded independently and share new data elements using existing VLM systems. Another function of the VLM is to provide a web interface to a remote operator that can be used for reporting and status updates for the host systems and the instruments to which the hosts are connected.

The IPS 102 implements data element storage and sharing of data that as delivered from a LIS, in the illustrative embodiment described herein, conforms to an adaptation of the Health Level Seven (HL7) standard for information exchange between medical applications, adapted as described hereinafter. However, it should be appreciated that other predetermined protocols, such as the IEEE 1073 Standard for Medical Device Communication or proprietary protocols designed for medical device communications, can be implemented. As illustrated in FIG. 3, Interface Software A (referred to herein synonymously as "ISA" or "Ventana Interface Point" software or "VIP") also resides on the IPS 102 and acts as a gateway between VLM and a LIS, which in this illustrative embodiment is implementing HL7. The data handled by the VIP includes case management, stain requests from the LIS, staining status and results back to the LIS. Standard TCP/IP protocols are used to connect with the LIS and VLM. Data mapping is available to permit site to site variations in data formats without custom code changes.

The IPS 102 forms the functional connection between the LIS 104 and the IPN, where the IPN is comprised of the IPS 102, host computers and instruments, all connected into a system. The function of the IPS is logically and structurally partitioned into two pieces, the VLM and VIP, as described hereinbefore. While each of these are comprised of contained software objects, it is the encapsulation of their functionality that enable the system to be scalable—for both increased numbers and types of instruments and for function. For the specific application of laboratory automation, it is especially important as the current state of installed instrumentation, types and purposes of data transmission and sharing and levels of automation will be dynamic.

Figure 3A:
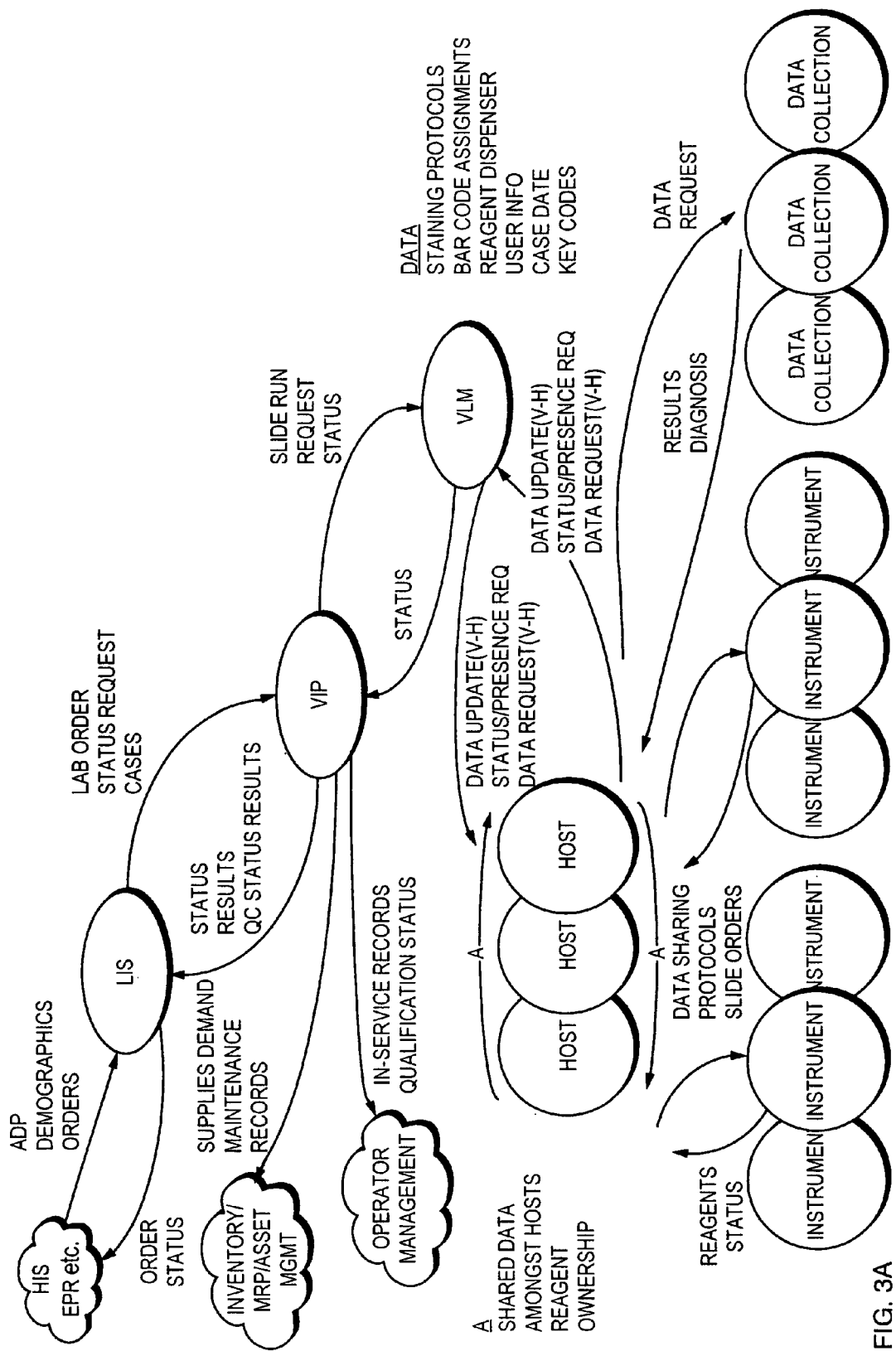
FIG. 3A is a data flow diagram of a system implementing an IPN according to an illustrative embodiment.

The illustrative embodiment of a system described herein, therefore, is comprised of hardware entities and software programs that are interfaced through communications protocols and data sharing (generally through the use of databases and extensible binary structures). In addition to the physical representation of FIG. 3, the system can be represented as a data flow, such as illustrated in FIG. 3*a*

From this perspective, the LIS and other institutional data systems (e.g., HIS, EPR, Inventory management, maintenance management, operator management) represent data resources and management systems that functionally require interaction with the IPN. It is the role of the VIP to provide the gateway interface for this communication with any multiplicity of institutional systems. The advantage of having this encapsulation of function is that it becomes possible to identify and tailor this interface to the needs of a specific site or institution while retaining the key management functions for the IPN in the VLM. In this way, the VIP is the manager for communications to the institution.

Alternately, the VLM provides the functionality to manage the IPN. This set of tasks and their highly unique set of data management and decision processes is encapsulated in the VLM for the purposes of integrating, at an appropriate level, the management functions associated with an entire IPN. Just as a Host is responsible for the management of a single or group of instruments, the VLM must synchronize data, arbitrate staining requests and manage the work flow throughout the IPN. Additionally, the VLM would manage the request and results for the inspection process and ultimately consolidate the laboratory information reporting for a complete order—from initiation through result reporting. Thus the illustrative embodiment provides a multiple tiered architecture, both physical and logical, for the management of workflow, data and status through the laboratory, for example for histology and clinical pathology. It is this tight integration, embodied in the functionally encapsulated modules, that facilitates the adaptation of this system into the highly varied (from site to site) institutional laboratory environment. In illustrative implementations relating to anatomical pathology, the data management method and apparatus described herein may be used to manage work flow, including but not limited to, pathology order placement; slide processing optimization on multiple instruments; slide identification through the process; bar code use; reagent use and supply; reagent sharing between laboratory instruments; operator in-service qualification; operator lock out on failure to meet training of QC requirements; laboratory instrument QC testing; and/or laboratory instrument QC lockout on failure to meet QC requirements.

In the illustrative embodiment involving the automation of a clinical pathology process, just as automation of the staining process provides cost, reliability and efficacy advantages over traditional, manual techniques, the automation of the larger clinical pathology process affords similar advantages. In particular, the ability to fully automate the process from sample preparation through result reporting eliminates labor cost, transcription errors, unnecessary data replication and time required to manually report results, as described hereinbefore.

The IPN forms the backbone for providing this level of automation as it has visibility to the order process into the laboratory, the status of an order as it proceeds through the process and can report back results. The ability to consolidate the preparation, processing, inspection and reporting is highly advantageous in obtaining efficiency and accuracy.

Since the VLM manages orders throughout the process, it forms the centerpiece for this integration. The addition of an automated data collection station for inspection (either fully automatic inspection or pathologist driven inspection with automated data collection) provides the next step in fulfilling the full initiation through reporting function. For automated data collection driven by a pathologist inspection, there can be a multiplicity of methods, such as a computer entry station, touch pad data entry, voice data entry, and interactive video with voice. Such data would become part of the clinical record for the specific order.

Referring still to FIG. 3A, the data flow diagram provides visibility at another level to the functional capabilities of the IPN. The data interactions depicted between the LIS and VIP show the high level nature of the interaction. Specifically, the LIS-VLM data flow is focused on IPN system status, staining orders and reporting results. Additionally, those interactions depicted with other non-LIS institutional entities (e.g., inventory and operator management) are related to material and work flow areas impacting the overall institution.

At a lower level (within the system architecture and specifically as between the VLM and hosts and hosts and instruments), the data objects are of a nature allowing for the management of specific aspects of the IPN operation. For example, some specific interactions deal with data sharing between hosts where staining protocols, bar code assignments and user information is exchanged as required to manage the operation and share common data between hosts and instruments.

At a yet lower level, data is shared between hosts to manage specific operating criteria that affect individual instruments. An example of this is reagent ownership, where a particular instrument claims ownership for a specific dispenser. Additionally, the addition of data collection stations to the IPN leverage the data hierarchy design by enabling the allocation and management of orders and reporting of results (which are the critical objects for data collection).

It is this hierarchy, the control exerted by individual entities in the IPN and the appropriate level of data sharing, exchange and storage that provides the efficient partitioning of functionality and data management within the IPN. The model of encapsulating function and associated data at an appropriate level is efficiently applied to this large scale system via the IPN and architecture as described.

Data sharing and storage in (general) is provided one of two ways, relating to the nature of which system entity drives the sharing functions. The ways in which this can occur (for the Host-VLM relationship) is for either the VLM or the host systems to control the active sharing of data over the IPN. In considering an optimal design for sharing and storage, it is critical to consider the nature of the designed functional encapsulation (as discussed hereinbefore with respect to the VIP and VLM as part of the IPS). As a general rule, the entity that has the most 'knowledge' of data requirements is best suited to drive the sharing and storage rules. In the case of the VLM and host computers, the overall detail of function relating to management of reagents and staining recipes is encapsulated in the host computers and consequently, they drive the sharing paradigm from a 'push' perspective—deciding what data is shared and when. In this way, the prioritization and actual actions taken to synchronize data is driven from the use case and represents the more efficient of the means of managing data sharing.

In the case of identifying data that the VLM and VIP may manage, a transition occurs where rather than maintaining a synchronized state, it may be more optimal to simply enable ad hoc transactions or status requests as necessary to support the functionality. In this way, the way in which data is managed changes from a maintained synchronized state to one of identifying and requesting data as required for a specific instance. The use of communications protocols tailored to support such transactions (e.g., HL-7) is highly appropriate for these types of data requirements.

As is known in the art, HL7 is an American National Standards Institute (ANSI) accredited standard that governs the exchange, management and integration of data in order to support clinical patient care and the management, delivery and evaluation of healthcare services. Adaptation and implementation of the HL7 standard allows new types of data elements to be shared without requiring software upgrades to IPS 102, thus allowing the software on first host computer 108 and second host computer 112 to be upgraded independently while sharing new data elements using existing IPS 102. For example, if first host computer 108 and second host computer 112 are disposed within the network of host computers 106 and are sharing data elements, then in order to avoid data loss the ISB in IPS 102 may include algorithm(s) to ensure that accurate data replication occurs. These algorithm(s) may accomplish this by allowing IPS 102 and network of host computers 106 to work in close cooperation with each other to evaluate which data elements being shared by first host computer 108 and second host computer 112 are the most current and by building and retaining a copy of these data elements. In essence, a "partnership" is formed between network of host computers 106 and IPS 102 and is explained in more detail hereinafter.

It should be appreciated that some data elements, such as those elements regarding reagents in an IPN with automated staining instrumentations, require that the host system have ownership rights to those elements and as such a software messaging system is provided to allow one host computer to marshal these elements, or request a transfer of ownership of these elements, from another host computer. The marshalling of data elements is explained in greater detail hereinafter. This ability to marshal data elements ensures that those data elements that require ownership rights get properly and safely changed to remain within predetermined limits (e.g. dispensed amount does not exceed container limits).

As described briefly above, HL7 is a standard that governs the exchange, management and integration of data between independent applications. As such, HL7 is an open messaging standard governing a method for moving clinical data between independent medical applications. HL7 is designed to enable data communications across a network in real-time, and is described in detail in the HL7 specifications, available from the Health Level Seven organization, Ann Arbor, Mich., which specifications are incorporated herein in the entirety. An implementation of HL7 is used, as described hereinafter, to communicate between the LIS and the single point server IPS 102, and ultimately with the host computer(s) 108, 112 and instruments 110, 114.

Figure 4:
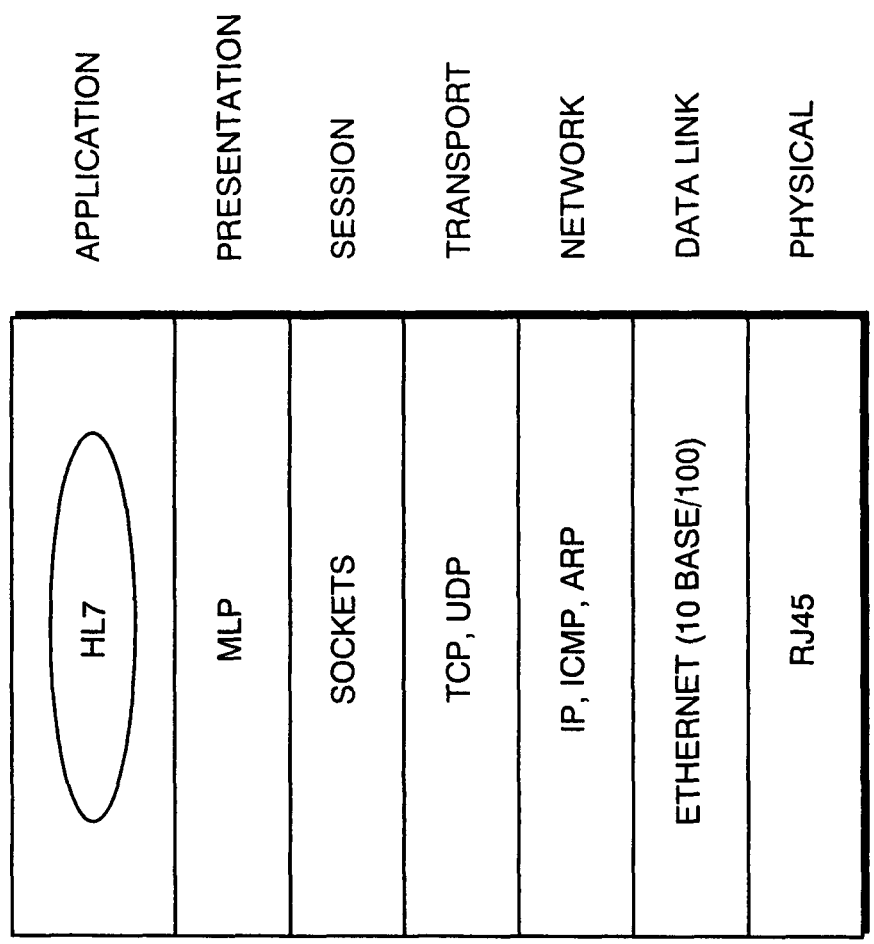
FIG. 4 is a block diagram illustrating a multi-layer software architecture.

Referring to FIG. 4, a high level block diagram illustrating a multi-layer (i.e. seven layer) software architecture is shown and includes a first level or "physical level," a second level or "data link level," a third level or "network level," a fourth level or "transport level," a fifth level or "session level," a sixth level or "presentation level" and a seventh level or "HL7 application level."

Figure 5:
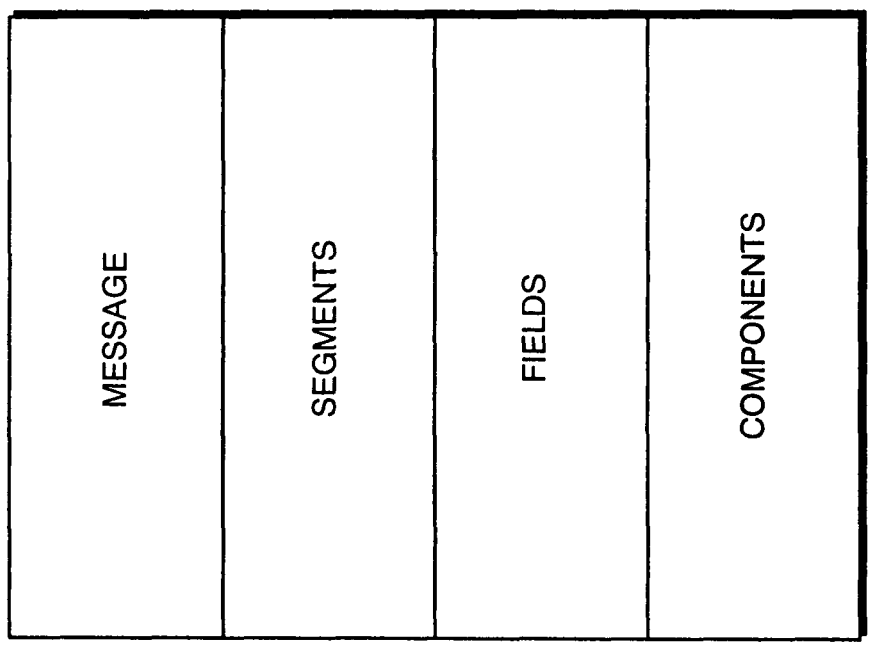
FIG. 5 is a block diagram illustrating an established hierarchy of an HL7 message.

The term "Level Seven" refers to a multi-level (i.e. seven level) software architecture scheme developed by the International Standardization Organization (ISO) and is an application-to-application interface. This means that HL7 defines specification protocols for level 7 functions only (hence, application-to-application interface) and does not define specifications for the remaining six (6) supporting levels. HL7 specifies the type of data to be exchanged, the timing of these communications and the treatment given certain predefined application-specific errors, such as patient demographic information, orders from physicians to the laboratory, test results from the lab to the physician, billing information and enterprise-wide scheduling. FIG. 5 illustrates an additional high level block diagram showing the established hierarchy that governs the construction of an HL7 message and includes a plurality of elements, such as a "components element," a "fields element," a segments element" and a "message element."

The overall HL7 standard is quite broad and supports a central patient care system as well as a distributed environment with departmental data. For example, specific interfaces or messages covered by the standard include patient admissions/registration, discharge or transfer (ADT) information; queries; resource and patient scheduling; orders, status results and clinical observations; billing; master file update information; medical records and patient referral and patient care. Although each of these interfaces or messages may be handled by this standard, for purposes of explanation only the Automatic Test Ordering (OML), Automatic Status Updates (OUL) and Master File Transfer (MFN and MFQ) messages, as implemented in the context of the interface point network, will be addressed in this detailed description. Each of these messages are described separately below.

It should be appreciated that the term "message," as used herein, refers to a group of segments in a defined sequence, the message is the atomic unit of data transferred between systems and each message has a message type that defines its purpose. Similarly, the term "trigger events" refer to real-world events that initiate a message. The trigger event is a code that represents a value, such as an order event and involves a one-to-many relationship between message types and trigger event codes. Thus, although a trigger event code may be associated with only one message type, a message type may be associated with multiple trigger event codes. Moreover, the term "extraneous message segments" refer to those segments that are "Ignored" or "Not Used." Although it is preferred that Ignored or Not Used message segments are not included in an HL7 message, it is not a requirement. As such, when present no data validation is performed on Ignored message segments.

Automatic Test Ordering Message

The ordering message, or Automatic Test Ordering (OML) message, is a unidirectional message used to send accessioning information and test orders from the LIS to the laboratory instrument. HL7 includes bi-directional message/acknowledgement communication message pairs. It should be noted that unidirectional messaging may be used to characterize the flow of information, for example, as may be originated by the LIS and sent to the IPS. The OML message applies to new orders and may not be used to cancel or modify existing orders. The OML message typically includes a plurality of key message segments that include a Message Header (MSH) segment, a Patient Identification (PID) segment, a Patient Visit (PV1) segment, a Specimen and Container (SAC) segment for information relating to the tissue sample, a Common Order (ORC) segment for adding new test orders, an Observation Request (OBR) segment to allow the LIS to request an order and a Message Acknowledgement (MSA) segment to allow for the receipt of any sent messages. The MSH segment, SAC segment, ORC segment and OBR segment are required fields and must contain valid information. The PV1 segment is optional and may or may not include information and the PID segment is a conditional field which is required only if the PV1 segment is completed.

Example of an OML Test Order Message

MSH|^~\&|MFN|LIS_APP|APLAB|VIP|APLAB|2002120211
26|| OML^O21|MSG03219|P|2.4|<cr>
PID|||112234^^^METRO HOSPITAL~98223^^^SOUTH
LAB||Everyman^Adam|||19600614|M||C|2101
Webster # 106^^Oakland^CA^94612|

```
PV1||O|||||0148^ADDISON,JAMES|0148^ADDISON,JAME
    S|0148^ADDISON,JAMES|AMB|||||||0148^ADDISON
    ,JAMES|S|1400|A|||||||||||||||||||GENHOS|||
    |||<cr>
SAC|||S03-13241A<cr>
ORC|NW|5212498721A|||ID|B~E<CR>
OBR|1|5212498721A|295^DAB
    Paraffin^STAIN|||199807240826|||||||||||||Ser
    gical Specimen<CR>
ORC|NW|S03-00234B^LAB|||||^^^^^R<CR>
OBR|1|S03-
    00234B^LAB||111^iVIEW^STAIN|||199808101444|
    |||A||||XXX<CR>
SAC||S03-
    00241A^LAB||||SER||99980620081107|U^UNKNOWN<
    cr>
ORC|NW|S03-00241A^LAB|||||^^^^^R<CR>
OBR|1|S03-
    00241A^LAB||640^AFB^STAIN|||199808101444|||
    |A||||SER<CR>
ORC|NW|S03-00241A^LAB|||||^^^^^R<CR>
OBR|1|S03-
    00241A^LAB||642^IRON^STAIN|||199808101444||
    ||A||||SER<CR>
```

The SAC segment includes the data necessary to maintain the containers that are being used throughout the Laboratory Automation System and includes three (3) segment attribute fields: an external accession identifier field, an accession identifier field and a container identifier field. The external accession identifier field includes data that is used to identify the laboratory specimen based upon an identifier provided by an outside facility. The accession identifier field includes data that is used to identify the laboratory specimen based upon an identifier provided by the laboratory performing the tests. It should be noted that the accession identifier field may or may not contain data referring to more than one container. The container identifier field includes data that assigns a unique identifier to the container. A container may hold a primary (original) or an aliquot (secondary) sample of that specimen. For a primary sample, this field includes a Primary Container ID and for bar-coded aliquot samples, this field includes an Aliquot Container ID. In the event an aliquot sample is non-bar-coded, this field remains empty or filled with default data.

The ORC segment is used to transmit fields that are common to all requested services and includes six (6) segment attribute fields: an Order Control (ORC-1) attribute field, a Placed Order (ORC-2) attribute field, a Filled Order (ORC-3) attribute field, a Placer Group (ORC-4) attribute field, an Order Status (ORC-5) attribute field and a Response Flag (ORC-6) attribute field.

The ORC-1 attribute field is a required field that determines the function of the order segment and is critical to the operation of both OML and OUL messages. The ORC-1 attribute field includes ORC field values for a New order/service (NW) function, an Order/service accepted & OK (OK) function and an Unable to accept order/service (UA) function. It should be noted that the only valid value in this field for an OML message is NW. The OUL message, however, can have one of two (2) possible values depending on predetermined conditions. If the observation was completed successfully, then the OUL message value should be OK. If the observation was not completed, then the OUL message value should be UA. In this case, the observation segments (OBX) as described below may be examined to determine the cause of the incomplete message. Each order message that defines any type of new order (i.e. ORC-1=NW, OK or UA) requires an ORC/OBR message pair to define each order to the receiving application. This also applies to any other types of orders, with the OBR being replaced by the appropriate order detail segment.

The ORC-2, ORC-3 and ORC-4 attribute fields are optional fields that are typically used to send the sample accession number to the laboratory instrument and are used to identify an individual order. The ORC-2, ORC-3 and ORC-4 attribute fields contain a unique order identifier which is of the Entity Identifier (EI) type, as explained below. It should be noted that although the first component (a string that identifies an individual order) has a suggested, but not required, fifteen (15) character limit, the first component may include any number of characters as defined by the HL7 standard.

The ORC-5 attribute field is an optional field that is used to specify the status of an order, but that does not initiate any action. The ORC-5 attribute field includes five (5) possible values: an "Identifier" (ID) value, an "In Process" (IP) value, an "Order is completed" (CM) value, an "Error, order unable to complete" (ER) value and an "Order is on hold" (HD) value. It should be noted that in some cases it is assumed that the order status always reflects the status as it is known to the sending application at the time the message is sent. It should also be noted that only the filler can originate the value in this field. As such, this field is only valid in the ORL and OUL messages.

The ORC-6 attribute field is an optional field that enables the status update (OUL) and allows the sending application to determine the amount of information to be returned from the filler via one or more OUL messages. The ORC-6 attribute field includes five (5) possible values: a "Report begin of staining run status" (B) value, a "Report end of staining run status" (E) value, a "Report end of imaging run status" (I) value, a null or "Default" (N) value and a "Pointer" (L) value. It should be noted that this field may be repeated with several ID values if multiple OUL messages are desired.

It should be noted that the ORC segment is a required field in an OML message and if an order detail segment is present, the ORC segment is also mandatory in Unsolicited Laboratory Observation (OUL) messages.

The OBR segment is used by the LIS to request an order and includes seven (7) attribute fields: a "Placer Order Number" (OBR-2) attribute field, a "Filler Order Number" (OBR-3) attribute field, a "Universal Service Identifier" (OBR-4) attribute field, an "Observation Data/Time Number" (OBR-7) attribute field, a "Label Template" (OBR-18) attribute field, a "Text" (OBR-19) attribute field and a "Placer Supplemental Service Information" (OBR-46) attribute field.

The OBR-2 attribute field is a conditional field that is identical to the ORC-2 attribute field and is used to identify an individual order. This field is a special case of the EI field as explained below and is conditional in a manner responsive to whether a placer order number is provided in attribute field ORC-2. For example, if a placer order number is not provided in attribute field ORC-2, then OBR-2 is a required field.

The OBR-3 attribute field is a conditional field that is identical to the ORC-3 attribute field and is used to identify an individual order. This field is a special case of the EI field as explained below and is conditional because it is required only in the OUL message and will be the same value as the ORC-3 attribute field. OBR-3 is assigned by the order filling (receiving) application and identifies an order uniquely among all orders from a particular filling application.

The OBR-4 attribute field is a required field that contains the CE data type of the staining protocol that will be performed on the slide. This is based on local protocols defined on the laboratory instrument and may be used by the laboratory instrument to determine which staining protocol to use on the slide.

The OBR-7 attribute field is a conditional field that contains any clinically relevant date/time of observation and is the data that the laboratory system uses to identify what staining protocol to perform on a slide. This field represents the date and time the specimen was first obtained. This field is conditional because when the OBR is transmitted as part of a report message, this field must be completed and it is transmitted as part of a request, then this field may be ignored.

The OBR-18 attribute field is an optional field that is a user-defined string of text that allows the LIS to specify the name of the template to be use when printing the slide label. If the value in this field is "NO LABEL" or is NULL (e.g., " "), then a label is not generated. Moreover, this may be used to print the instrument bar code label using alternative label printing resources. If this attribute is null, then the laboratory instrument may use the default label template to print.

The OBR-19 attribute field is an optional field that is reserved for future use. This field may be used for site defined bar code symbology and bar code text to uniquely identify various items, such as slides in a laboratory. This field may also be used to allow the LIS to inform the laboratory instrument of unique text that is encoded in the bar code that will be encountered when reading the bar code.

The OBR-46 attribute field is an optional field that is used to describe details such as what types of imaging protocols should be done on the slide that received the OBR-4 staining protocol. The OBR-46 field contains supplemental service information sent from a placer system to a filler system for the universal procedure code reported in OBR-4 Universal Service ID. This field may be used to provide ordering information detail not available in other fields in the OBR segment. Multiple supplemental service information elements may also be reported. This field may also be used to request Image Protocols (s) for the slide after it has been stained with the protocol requested in OBR-4.

It should be noted that when observations are successfully completed, the message returned to the placer field(s) may include the order segment (OBR) followed by observation (OBX) segments for each distinct observation generated by the order. The number of such observation segments may be dependent upon the number of individual measurements performed in the process. In the OUL message if the observations cannot be performed, e.g. because the Universal Service Identifier doesn't match a known protocol, the placer will receive an OBR-25-result status equal to X (to indicate that the study was not performed). In this case, no observation segments will be transmitted.

The MSA segment includes information sent while acknowledging another message and includes six (6) attribute fields: an "Acknowledgement Code" attribute field, a "Message Control ID" attribute field, a "Text Message" attribute field, an "Expected Sequence Number" attribute field, a "Delayed Acknowledgment Type" attribute field and an "Error Condition" attribute field.

The Acknowledgment Code field is a required field and includes an acknowledgment code that may include at least one (1) of following three (3) values: AA (Original mode: Application Accept—Enhanced mode: Application acknowledgement: Accept), AE (Original mode: Application Error—Enhanced mode: Application acknowledgement: Error) or AR (Original mode: Application Reject—Enhanced mode: Application acknowledgement: Reject).

The Message Control ID field is a required field and includes the message control ID of the message that was sent by the sending system. Also, this may allow the sending system to associate this response with the message for which it is intended. The Text Message field is an optional field that further describes an error condition. This text may be printed in error logs or presented to an end user. The Expected Sequence Number is an optional numeric field used in the sequence protocol. The Delayed Acknowledgment type is optional and may be ignored.

The Error Condition field is an optional field that may allow the acknowledging system to use a user-defined error code to further specify AR or AE type acknowledgments. The Error Condition field may include at least one of the following thirteen (13) values: 0, 100, 101, 102, 103, 200, 201, 202, 203, 204, 205, 206 and 207. An Error Condition value of "0" gives an error text message of "message accepted" and indicates success. This is typically used for systems that must always return a status code and is optional, as the AA conveys success. An Error Condition value of "100" gives an error text message of "Segment Sequence Error" and indicates that the message segments were not in the proper order, or that the required segments are missing. An Error Condition value of "101" gives an error text message of "Required Field Missing" and indicates that a required field is missing from a segment. An Error Condition value of "102" gives an error text of "Data Type Error" and indicates that the field contained data of the wrong data type, e.g. an NM field contained "FOO". An Error Condition value of "103" gives an error text of "Table value not found" and indicates that a field of data type ID or IS was compared against the corresponding table, and not match was found.

An Error Condition value of "200" returns an error text message of "Unsupported Message Type" and indicates that the message type is not supported. An Error Condition value of "201" returns an error text message of "Unsupported Event Code" and indicates that the event code is not supported. An Error Condition value of "202" returns an error text message of "Unsupported Processing ID" and indicates that the processing ID is not supported. An Error Condition value of "203" returns an error text message of "Unsupported Version ID" and indicates that the version ID is not supported. An Error Condition value of "204" returns an error text message of "Unknown Key Identifier" and indicates that the ID of the patient, order, etc., was not found. This field may be used for transactions other than additions, e.g. transfer of a non-existent patient. An Error Condition value of "205" returns an error text message of "Duplicate Key Identifier" and indicates that the ID of the patient, order, etc., already exists. This field may be used in response to addition transactions (Admit, New Order, etc.). An Error Condition value of "206" returns an error text message of "Application Record Locked" and indicates that the transaction could not be performed at the application storage level, e.g. database locked. An Error Condition value of "207" returns an error text message of "Application Internal Error" and is a catchall for internal errors not explicitly covered by other codes.

Automatic Status Updates

The status results message, or Automatic Status Updates (Unsolicited Laboratory Observation or OUL) message is also a unidirectional message. However, the OUL is generated by the laboratory instrument and received by the LIS to notify the LIS of the specimen status. The OUL message is a response status message that combines the original order request from the LIS with a status update relating to that order request and includes at least two (2) key segments: an OBX segment which is the status of each component of the diagnostic report and a ZSI segment which includes detailed information about the reagents used in the test.

It should be noted that with the segment types OBX and OBR, almost any clinical report may be constructed as a three level hierarchy, with the PD at the upper level, an order record (OBR) at the next level and one or more observation records (OBX) at the bottom. It should further be noted that one result segment (OBX) is transmitted for each component of a diagnostic report and it permits the communication of substance data (lot, manufacturer, etc.) of the reagents and other substances involved in the generation of analysis results in addition to the results themselves via the ZSI segments.

The Observation (OBX) segments allow for the transfer of information regarding run number, start time, end time and error messages and includes at least five (5) OBX attribute fields: a Set ID (OBX-1) attribute field, a Value Type (OBX-2) attribute field, an Observation Identifier (OBX-3) attribute field, an Observation Sub-ID (OBX-4) attribute field and an Observation Value (OBX-5) attribute field.

The OBX-1 field is a required field that contains the sequence number. The OBX-2 field is a required field that contains the format of the observation value contained in OBX-5 field and may include at least one of the following values: OBX-2=NM indicates a numeric format, OBX-2=ST indicates a string format and OBX-2=TS indicates a time stamp format. The OBX-3 field is a required field that includes at least one unique identifier for the observation. This may reflect the staining protocol value in the ORC-4 field, with the exception that when this observation refers to an imaging result, OBX-3 field may reflect the value of one of the image protocols in the OBR-46 field. The OBX-4 field is a required field that may be used to distinguish between multiple OBX segments with the same observation ID organized under on OBR and may be used to categorize the observation segment. The OBX-4 field may include at least one of the values shown in Table 1:

TABLE 1

| OBX-4 Value | Description |
| --- | --- |
| HostID | Host ID of the laboratory instrument providing the service. |
| HostVersion | Software Version of the Providing Host. |
| StainerSerialNumber | Serial number of the laboratory instrument providing the service. |
| StainerEffectiveType | Effective type of the providing laboratory instrument. |
| RunNumber | Host's run number assigned to provided service. |
| RunStartTime | Start time of service run. |
| RunEstimatedTime | Estimated number of minutes run is expected to take. |
| SlidePosition | The position this slide is located on the laboratory instrument. |
| RunCompletedTime | Actual time service run finished. |
| RunTime | Actual number of minutes run took to run. |
| RunError(n) | Run Error Message (n starts at 1 and increment for each successive error message. |

Observation Sub

The OBX-5 field is a required field that contains a value observed by the observation producer. OBX-2 (Value Type) contains the data type for this field according to which observation value is formatted.

The Substance Identifier (ZSI) segment contains data necessary to identify the substance (e.g., reagents) used in the production of analytical test results and includes at least ten (10) attribute fields. The combination of these fields uniquely identify the substance and depending upon the manufacturer, all or some of these fields are required. If the analysis requires multiple substances, this segment is repeated for each substance. The ZSI segment allows for the transfer to information regarding the manufacturer of the reagent, the chemical name, the catalogue number, the lot number and expiration and the serial number.

The ZSI segment includes the attribute fields shown in Table 2:

TABLE 2

| ZSI Attribute Field | Description |
| --- | --- |
| Substance Type | This is a required field that identifies the substance type used for analysis. It is the group that this substance is in, ANTIBODY, REAGENT, PROBE or BULK. |

ZSI Attribute Fields

TABLE 2-continued

ZSI Attribute Fields

| ZSI Attribute Field | Description |
| --- | --- |
| Substance Name | This is a required field that identifies the substance name used for analysis. |
| Substance Lot Number | This is a require field that specifies the lot number assigned by the manufacturer during production of the substance. |
| Substance Lot Serial Number/Container Identifier | This is a required field that specifies the container assigned by the manufacturer during production of the substance. This identifier should be unique within specific lots of the substance. |
| Catalog Number | This is an optional field that specifies the Manufacturer's catalog ordering number. |
| Substance Other Name | This is an optional field that is used to described additional information about the substance. In the case of Antibodies, it will specify the Clone Name. In the case of Probes, it will hold the Probe Label type. In the case of Reagents and Bulk, this field is not used. |
| Substance Manufacturer Name | This is a required field and identifies the manufacturer of the substance. |
| Expiration Date | This is a required field and identifies the expiration date of the substance. |
| Received Date/Time | This is a required field and identifies the date the substance was received. |
| Intended Use Flag | This is an optional field and identifies the manufacturer's intended use of the substance. This field includes at least four valid values including: ASR (Analyte Specific Reagent), IVD (In Vitro Diagnostic (Class 1 Exempt)), 510(K) (Pre-Market 510(K) Cleared) and PMA (Pre-Market Approved). |

Master File Exchange Message

The master file exchange or master file transfer message is also a unidirectional message and includes two (2) types of messages 1) a Master File Change Notification (MFN) message and a Master File Query (MFQ) message. The master file transfer message is generated by the laboratory instrument and received by the LIS to keep master file information synchronized between the two systems.

The MFQ message allows the LIS to query for a group of records in a particular master file. The MFQ message includes two (2) required segments: a Message Header (MSH) segment and a Query Definition (QRD) segment. The QRD segment is used to define a query and includes ten (10) attribute fields as shown in Table 3.

The MFQ transaction also includes a Master File Response (MFR) message that includes seven (7) segments: a Message Header (MSH), a Message Acknowledgement (MSA), a Query Definition (QRD), a Master File Identification (MFI), a Protocol Entry (ZVP), a Template Entry (ZVT) and a 3$^{rd}$ Party Chemistry Entry (ZSI), wherein all but ZVP and ZVT are required segments.

The MFI segment is typically used to identify the master file and includes five (5) segment attribute fields as shown in Table 4.

TABLE 3

QRD Attribute Fields

| QRD Attribute Field | Description |
| --- | --- |
| QRD-1 | This is an optional field that identifies the Query Date/Time. |
| QRD-2 | This field identifies the Query Format Code. |
| QRD-3 | This field identifies the Query Priority. |
| QRD-4 | This is an optional field that identifies the Query ID. |
| QRD-5 | This field identifies the Deferred Response Type. |
| QRD-6 | This field identifies the Deferred Response Data/Time. |
| QRD-7 | This field identifies the Quantity Limited Request. |
| QRD-8 | This field identifies the Who Subject Filter. |
| QRD-9 | This is a required field that identifies the What Subject Filter and describes the kind of information that is required to satisfy the query request. Valid values include: PROTOCOL (Staining Protocols), TEMPLATE (Slide Templates), ANTIBODY (Logged Antibodies), REAGENT (Logged Reagent), PROBE (Logged Probes) and BULK (Logged Bulks) |
| QRD-10 | This field identifies the What Department Data Code. |

TABLE 4

MFI Attribute Fields

| MFI Attribute Field | Description |
| --- | --- |
| MFI-1 | Master File Identifier-- This is a required field of CE type data that identifies the database table being affected. A plurality of values are supported by this field and include: PROTOCOL (Staining Protocols); TEMPLATE (Slide Template), ANTIBODY (Logged Antibodies), REAGENT (Logged Reagents), PROBE (Logged Probes) and BULK (Logged Bulks). |
| MFI-2 | Master File Application Identifier - This is an optional field that defines the optional code for which the application is responsible for maintaining and may include a valid value, such as VIP. |
| MFI-3 | File-Level Event Code -- This is an optional field that identifies the file level event code and may include a valid value, such as UPD, where UPD is a file level event code described as Change file records as defined in the record-level event codes for each record that follows. |
| MFI-4 | Entered Date/Time -- This is an optional field that identifies the time stamp for file level events. |
| MFI-5 | Effective Date/Time -- This field may be ignored because all Master File transactions are posted as effective when they are received. |

The ZVP segment is used to enter master file protocol information and includes three (3) segment attribute fields as shown in Table 5.

TABLE 5

ZVP Attribute Fields

| ZVP Attribute Field | Description |
| --- | --- |
| ZVP-1 | Staining Protocol Identifier -- This is a required field of CE type data that identifies the Name, Number and Platform Type of the Protocol. A plurality of values are supported by this field and include: My Protocol (ID = 255, STAIN); Image Protocol (IMAGE), Protocol 2 (ID = 222, STAIN) and AFB (ID = 640, STAIN). It should be noted that the numeric ID value range should fall between 0 and 999. |
| ZVP-2 | Modified Date/Time - This is a required field that identifies the date this protocol was last modified |
| ZVP-3 | Procedure Name-- This is an optional field of ST type data that identifies the Procedure that the specified Protocol is derived from. |

The ZVT segment is used to enter master file template information and includes two (2) segment attribute fields as shown in Table 6. It should be noted that the ZVT segments are only used when the field type in the MFI-1 segment field is set to template.

TABLE 6

ZVT Attribute Fields

| ZVT Attribute Field | Description |
| --- | --- |
| ZVT-1 | Template Name -- This is a required field of ST type data that identifies the Name of the Label Template. |
| ZVT-2 | Entered Date/Time - This is a required field of TS type data that identifies the date this template was last modified |

The ZSI 3rd party Chemistry/Substance segments are user-defined segments that are only used when the field type in the MFI-1 segment field are set to ANTIBODY, REAGENT, PROBE or BULK.

The MFN messages are generated to synchronize laboratory instrument protocols, slide label templates and 3rd Party Chemistry with other systems and include a Master File message and a Master File Acknowledgment message. The Master File message may be used to accept third party chemistry information that may be used with user-fillable dispensers and includes six (6) segments: a Message Header (MSH) segment, a Master File Identification (MFI) segment, a Master File Entry (MFE) segment, a Protocol Entry (ZVP) segment, a Template Entry (ZVT) segment and a 3rd Party Chemistry Entry (ZSI) segment. All of these segments are required with the exception of the ZVP segment and the ZVT segment which are not used during the import procedure.

The Master File Acknowledgment message is used to acknowledge receipt of a Master File message and includes two (2) required segments: a Message Header (MSH) segment, an Acknowledgment (MSA) segment, and one (1) optional segment: an Error (ERR) segment.

The MFE segment is a required segment that repeats several data elements from the ZVP, ZVT and ZC3 segments. The MFE segment is used to indicate the Record-Level Event Code during import and export operations which will indicate whether a record has been added, deleted or updated and includes five (5) segment attribute fields as shown in Table 7.

TABLE 7

MFE Attribute Fields

| MFE Attribute Field | Description |
| --- | --- |
| MFE-1 | Record Level Event Code -- This is a required field of ID type data that defines the record-level event for the master file record identified by the MFI segment and the primary key field in this segment. Valid values for this field include: MAD (Add record to master file), MDL (Delete record from master file) and MUP (Update record for master file). It should be noted that if the file-level event code is "REP" (MFI-3 replace file), then each MFE segment must have a record-level event code of "MAD" (add record to master file) in this field. |
| MFE-2 | MFN Control ID - This field may contain data of TS type. |
| MFE-3 | Effective Date/Time -- This is an optional field of TS type data that identifies the date and time the change took place. |
| MFE-4 | Primary Key Value - This is a conditional field that uniquely identifies the record of the master file (identified in the MFI segment) to be changed (as defined by the record-level event code). This field is required when the value of MFE-1 is equal to MDL or MUP. |
| MFE-5 | Primary Key Value Type - This is a conditional field that contains the HL7 data type of MFE-4. Valid values for this field include: PROTOCOL (Staining Protocols), TEMPLATE (Slide Templates), ANTIBODY (Logged Antibodies), REAGENT (Logged Reagents), PROBE (Logged Probes) and BULK (Logged Bulks). This field is required when the value of MFE-1 is equal to MDL or MUP. |

In an illustrative implementation wherein the lab instruments 110, 114 (FIG. 3) include automated slide staining, in order to provide an editable mechanism to allow received HL7 messages to be transformed and mapped to slide data elements, an editor with a GUI interface is implemented to allow a user to build and test a transform script that consists of rules for processing HL7 messages.

This mechanism provides an object that can both perform routine HL7 message transformations for using a live transform script and also maintain a transform script that is being actively edited and is not live.

The field mapper function resident in the IPS 102 (FIG. 3), revolves around a single object that will: load and hold the live script; permit placing the script in edit mode without losing the live script; permit taking an edited script live; save an edited script; and perform routine HL7 transformations using the live script, modifying the case data as required.

The application running on the illustrative IPS 102 will create a field mapper object when required and will use it primarily to process a received HL7 message, resulting in case data being extracted from the HL7 message as required. The field mapper needs to be very flexible so that it can work with a large variety of HL7 message data structures present at customer sites. To accommodate this, processing of message data is codified in script 'rules' that consist of an interpreted list of instructions to follow to transform the message data into case data. The IPS 102 handles these processing rules. The following are the 9 slide data fields defined in an illustrative case:

1) Template;
2) PatientID;
3) PatientNAME;
4) Institution;
5) Requester;
6) AccessionID;
7) CaseID;
8) BlockID; and
9) SlideID.

In this illustrative embodiment these are the only possible output fields that can be altered during field mapping transformations. However, it should be appreciated that in other implementations other fields may be defined and processed. The purpose of the field mapper is to fill these data fields with the proper data extracted from the HL7 message.

Those skilled in the art will appreciate that there are numerous but finite HL7 fields present in the HL7 message that can contain data to be harvested by the script.

Script Language Components:

The script field mapping language will consist of rules coded into lines in the general form:

<target element>=<source element>

Taken together, slide data fields, HL7 message elements, internal variables and literal strings will be referred to as 'data types'. Data types can be present in script lines as follows:

| Data Type | Target (Target Data Objects) | Source (Source Data Objects) |
| --- | --- | --- |
| Slide Data Field | x | |
| HL7 Message Element | | X |
| Internal Variable | x | X |
| Literal String | | X |

Internal variables are user definable at the time the script is edited and are used to hold results temporarily during script command processing. Internal variables are created automatically when seen and initially have an empty value.

The language editor is the only way that a user can create script commands. This eliminates development of an elaborate parsing engine to handle user-typed script command lines. Even though script commands will be stored in binary format, they will be presented in a format that makes it easy for a user to view. (This displayed format is used below when discussing syntax of the special functions, even though parsing is not required of the command lines presented.)

COPY Special Function

This function is used to copy the entire contents of one data object and save it to another. The syntax is as follows:

[target data object]=COPY([source data object])

Examples:

If x='1234'

[s]=COPY([x])

results in '1234'

EXTRACT Special Function

This function is a very flexible string extraction function that can be used to mine delimited data from a source data object. Extraction is done using a defined delimiter string and a starting and ending delimiter count. This function allows data to be extracted in various ways such as the left-most, right-most or mid-string. Extraction starts from characters beginning with the starting instance count of the delimiter string, excluding the actual starting delimiter string. Extraction ends with the ending instance count of the delimiter, not including the actual ending delimiter string.

The syntax is as follows:

[target data object]=EXTRACT([source data object], delimiter string, starting index count, ending instance count)

Delimiter strings can be any non-blank string the user types in.

Starting and ending index counts can be any positive integer value. Delimiter counts of 0 have special meaning and depend on where they are found. When a 0 is found in the starting instance count this means to start the extraction from the start of the data object. When a 0 is found in the ending instance count this means to end the extraction at the end of the data object. In other words, using 0 for a starting instance count means take the left part of the data object, which using 0 for a ending instance means to take the right side of the data object.

Examples:

[x]=EXTRACT(['1234-567-1111-9999]', '-', 1, 2)

results in '567'

[x]=EXTRACT(['1234-567-1111-9999'], '-', 1, 3)

results in '567-1111'

[x]=EXTRACT(['1234-567-1111-9999'], '-', 0, 2)

results in '1234-567'

[x]=EXTRACT(['1234-567-1111-9999'], '-', 1, 0)

results in '567-1111-9999'

[x]=EXTRACT(['1234-567-1111-9999'], '-', 0, 0)

results in '1234-567-1111-9999'

(which is the whole field, actually)

CONCAT Special Function

This function is used to concatenate multiple source data objects together to make a long string to assign to the target data object. The syntax is as follows:

[target data object]=CONCAT([source data object 1], [source data object 2], [source data object 3], [source data object 4])

There can be 1-4 source data objects; 3-4 are optional. The contents of the source data objects are simply concatenated together to form the result. If more than 4 source data objects need to be concatenated together, an interim result could be stored in an internal variable and more CONCAT commands could follow to continue the concatenation.

Examples:

If x='1234', y='567', z='111'

[s]=CONCAT([x], ['-'], [y])

results in '1234-567'

[s]=CONCAT([s], ['-'], [z])

results in '1234-567-1111'

LEFT Special Function

This function is used to extract a certain amount of characters from the left side of the data object. The syntax is as follows:

[target data object]=LEFT([source data object], # characters)

Examples:

If x='1234'

[s]=LEFT([x], 3)

results in '123'

RIGHT Special Function

This function is used to extract a certain amount of characters from the right side of the data object. The syntax is as follows:

[target data object]=RIGHT([source data object], # characters)

Examples:

If x='1234'

[s]=RIGHT([x], 3)

results in '234'

MID Special Function

This function is used to extract a certain amount of characters from the middle of the data object. The syntax is as follows:

[target data object]=MID([source data object], starting position, # characters)

Starting position is the character position to start extracting characters. The number of characters is how many characters to extract.

Examples:

If x='1234'

[s]=MID([x], 2, 2)

results in '23'

Data Storage

Field mapping scripts will be stored in binary format on disk, and will be retrieved as required and stored as changed. The file format will not be human readable, by design. There will be data integrity features built into the file format such that data corruption will be apparent upon retrieval from disk so that invalid scripts will be readily identifiable and will not be executed. More specifically, data will be stored in encrypted, autowrapped CodeSafe streams.

Figure 6:
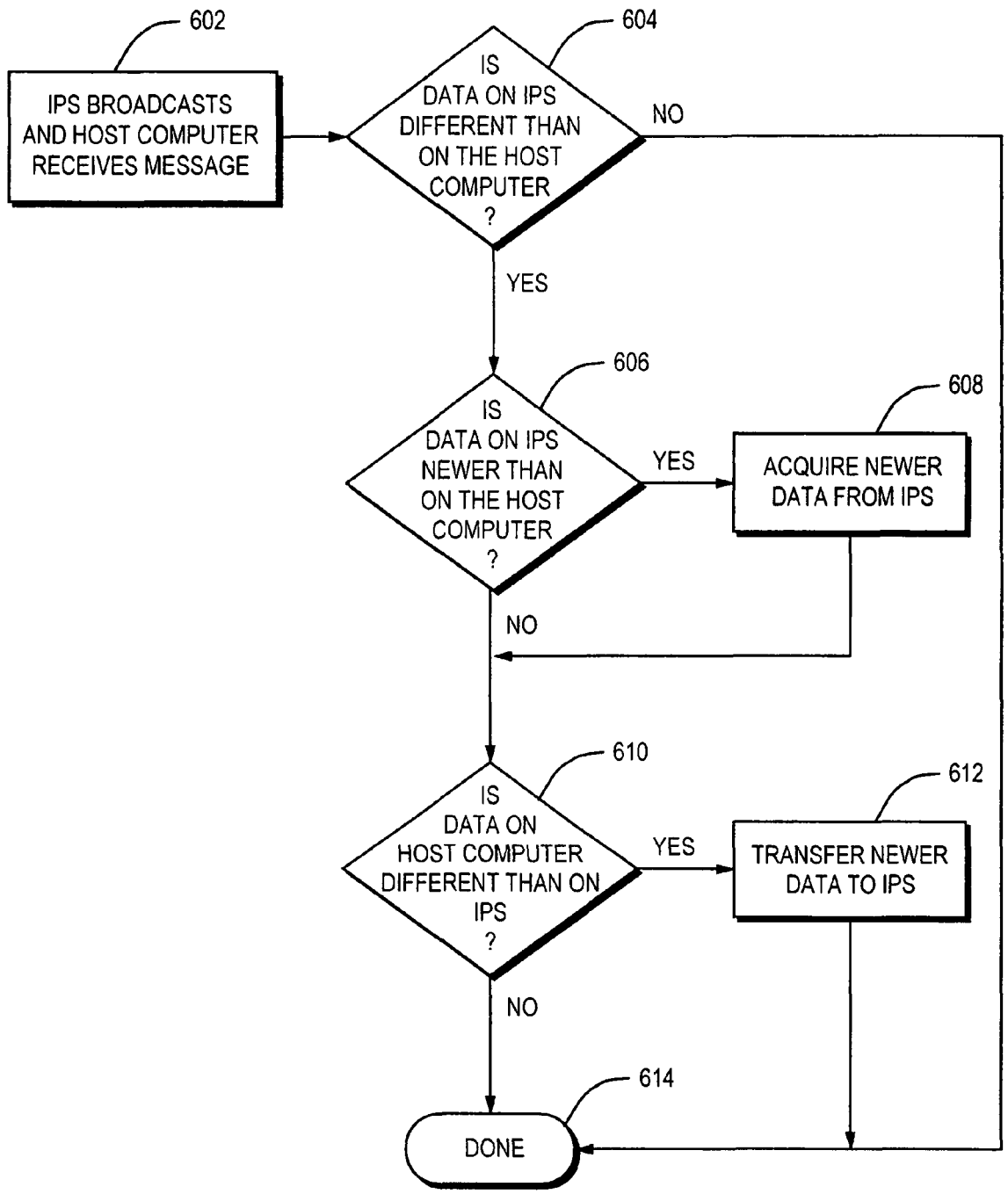
FIG. 6 is a block diagram illustrating a general method of Host/IP Data Synchronization according to an illustrative embodiment.

Referring now to FIG. 6, a high-level block diagram generally illustrating a host/IP data synchronization method 600 is shown and described as follows, with respect to the IPN illustrated and described hereinbefore with respect to FIG. 3. As described in more detail below, when IPS 102 first connects to IPN 100, IPS 102 begins to periodically broadcast a message to all of the devices on IPN 100, such as first host computer 108 and second host computer 112, to inform each of these devices that IPS 102 has connected to IPN 100, as shown in block 602. This message is of a User Datagram Protocol (UDP) type that is broadcast globally over the entire IPN 100 and includes information on what data is present on IPS 102. It should be appreciated that once IPS 102 connects to IPN 100 any host computer on IPN 100 that is configured to use IPS 102 services may then perform various functions, such as connecting with IPS 102 to request the latest data elements known to IPS 102, or sharing new data elements with IPS 102, thus making them available to network of host computers 106. The type of data that may be shared among instruments in a laboratory situation includes: staining protocols, user passwords and privileges, reagents (dispensers/vials), bulk fluids, cases/keycodes, templates, panels and 3$^{rd}$ party reagents. Each host computer in network of host computers 106 may be independently set up to either share or not share data elements, responsive to predetermined conditions, such as individual laboratory and/or computer host requirements.

Upon receiving this broadcast message, network of host computers 106 determines if the data on IPS 102 is different than the data on network of host computers 106, as shown in block 604. This may be accomplished by first host computer 108 comparing the data present on IPS 102 with the data present on first host computer 108 and second host computer comparing the data present on IPS 102 with the data present on second host computer 112. If the data present on both first host computer 108 and second host computer 112 is the same as the data present on IPS 102, then the synchronization process is complete, as show in block 614. However, if the dataset on network of host computers 106 is different from the dataset present on IPS 102, then network of host computers 106 initiates a synchronization protocol to transfer a copy of IPS 102's version of the data element to data sets on the hosts. However, if the dataset on network of host computers 106 is newer than the dataset on IPS 102, then the dataset on IPS 102 is updated with a copy of the version of the data elements from the host computers 106.

For example, if the dataset on IPS 102 is different, in whole or in part, from the dataset on first host computer 108, then first host computer 108 determines if its dataset is older than the dataset on IPS 102, as shown in block 606. This may be accomplished by first host computer 108 comparing its dataset with the dataset on IPS 102. If the dataset on first host computer 108 is older than the dataset on IPS 102, then the portion of the dataset on IPS 102 that is newer is acquired by first host computer 108, as shown in block 608. Once this has been accomplished, or if the dataset on first host computer 108 is not older than the dataset on IPS 102, then first host computer 108 determines if its dataset is newer than the dataset on IPS 102, as shown in block 610. As above, this may be accomplished by first host computer 108 comparing its dataset with the dataset on IPS 102. If the dataset on first host computer 108 is newer than the dataset on IPS 102, then the portion of the dataset on host computer 108 that is newer is transferred by first host computer 108 to IPS 102, as shown in block 612. Once this has been accomplished for each host computer on the entire IPN 100, then the synchronization process is complete, as shown in block 614.

Figure 7:
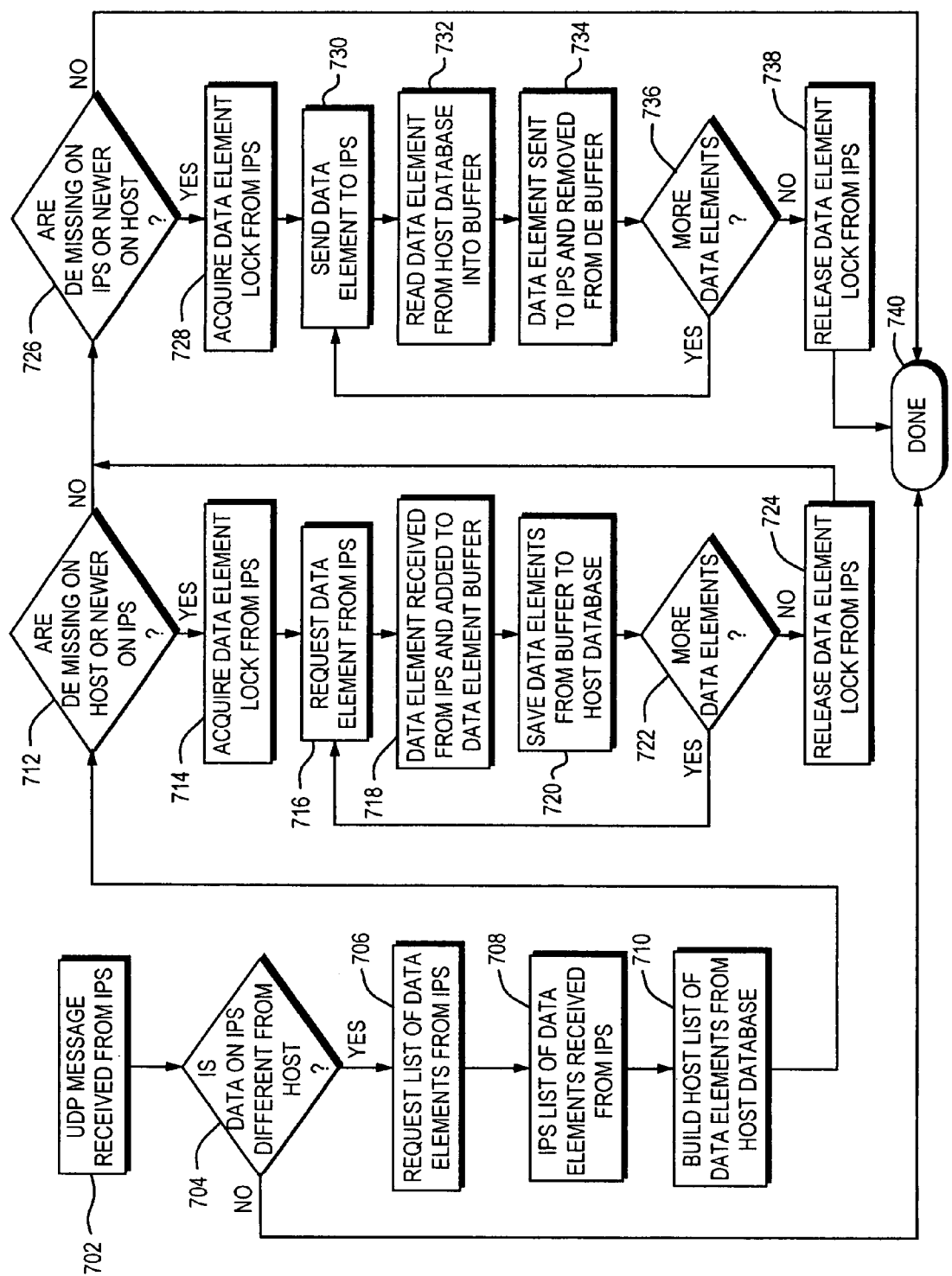
FIG. 7 is a block diagram illustrating a method for Host-Side Data Element Synchronization according to an illustrative embodiment.

Referring to FIG. 7, a low-level block diagram illustrating a host-side data element synchronization method 700 is shown and described as follows. Although the method of FIG. 7 is described in relation to first host computer 108, it should be appreciated that the method of FIG. 7 applies to each host computer in the plurality of host computers 106. As briefly described above, when IPS 102 first connects to IPN 100, IPS 102 begins to periodically broadcast a UDP message to all of the devices connected to IPN 100 to synchronize the information on all of the devices connected to IPN 100, in this case first host computer 108, as shown in block 702. This UDP message includes an IPS protocol version number as well as information regarding the data present on IPS 102, such as the timestamp or date of that information. When first host computer 108 receives this message, first host computer 108 determines whether its dataset is different from the dataset contained on IPS 102, as shown in block 704. This may be accomplished by comparing the IPS protocol version number contained in the UDP message with the protocol version number on first host computer 108. If the protocol version numbers match then the dataset on IPS 102 is the same as the dataset on first host computer 108 and Host-Side Data Element Synchronization method 700 is completed, as shown in block 740.

However, if the protocol version numbers do not match then the dataset on IPS 102 is different from the dataset on first host computer 108 and first host computer 108 requests the IPS list of data elements (i.e. table of contents) from IPS 102, as shown in block 706. Upon receipt of this request, IPS 102 sends and first host computer 108 receives the IPS list of data elements, as shown in block 708.

First host computer 108 builds a list of host data elements contained on first host computer 108, as shown in block 710 and compares the list of host data elements with the IPS list of data elements to determine if any data elements on first host computer 108 are missing or older than the data elements on IPS 102, as shown in block 712. If there are data elements on first host computer 108 that are missing or older than the data elements on IPS 102, then first host computer 108 requests and acquires a data element lock from IPS 102, as shown in block 714. In the event that there are multiple host computers, this data element lock allows only one host computer, such as first host computer 108, to access the data elements in IPS 102 without having to worry about other host computers simultaneously accessing and changing a particular data element. Once the data element lock has been acquired, first host computer 108 requests IPS 102 to send the data elements in question, as shown in block 716. When first host computer 108 receives the requested data element, first host computer 108 adds the data element to its data element buffer, as shown in block 718. The data element is then saved from the data element buffer to the host database of first host computer 108, as shown in block 720. First host computer 108 then determines if there are any more data elements on first host computer 108 that are missing or older than the data elements on IPS 102, as shown in block 722. If there are, then blocks 716 to 720 are repeated. Otherwise, first host computer 108 sends a request to IPS 102 to release the data element lock, as shown in block 724.

Upon release of the data element lock or if there are no data elements on first host computer 108 that are missing or older than the data elements on IPS 102, then first host computer 108 compares the list of host data elements with the IPS list of data elements to determine if any data elements on IPS 102 are missing or older than the data elements on first host computer 108, as shown in block 726. If there are data elements on IPS 102 that are missing or older than the data elements on first host computer 108, then first host computer 108 requests and acquires a data element lock from IPS 102, as shown in block 728. Once the data element lock has been acquired, first host computer 108 sends the data elements in question to IPS 102, as shown in block 730. First host computer 108 reads the data element from the host database into its data element buffer as shown in block 732 and the data element sent to IPS 102 is removed from the data element buffer, as shown in block 734. First host computer 108 then determines if there are any more data elements on IPS 102 that are missing or older than the data elements on first host computer 108, as shown in block 736. If there are, then blocks 730 to 734 are repeated. Otherwise, first host computer 108 sends a request to IPS 102 to release the data element lock as shown in block 738 and the host-side data element synchronization method 700 is completed, as shown in block 740.

Figure 8:
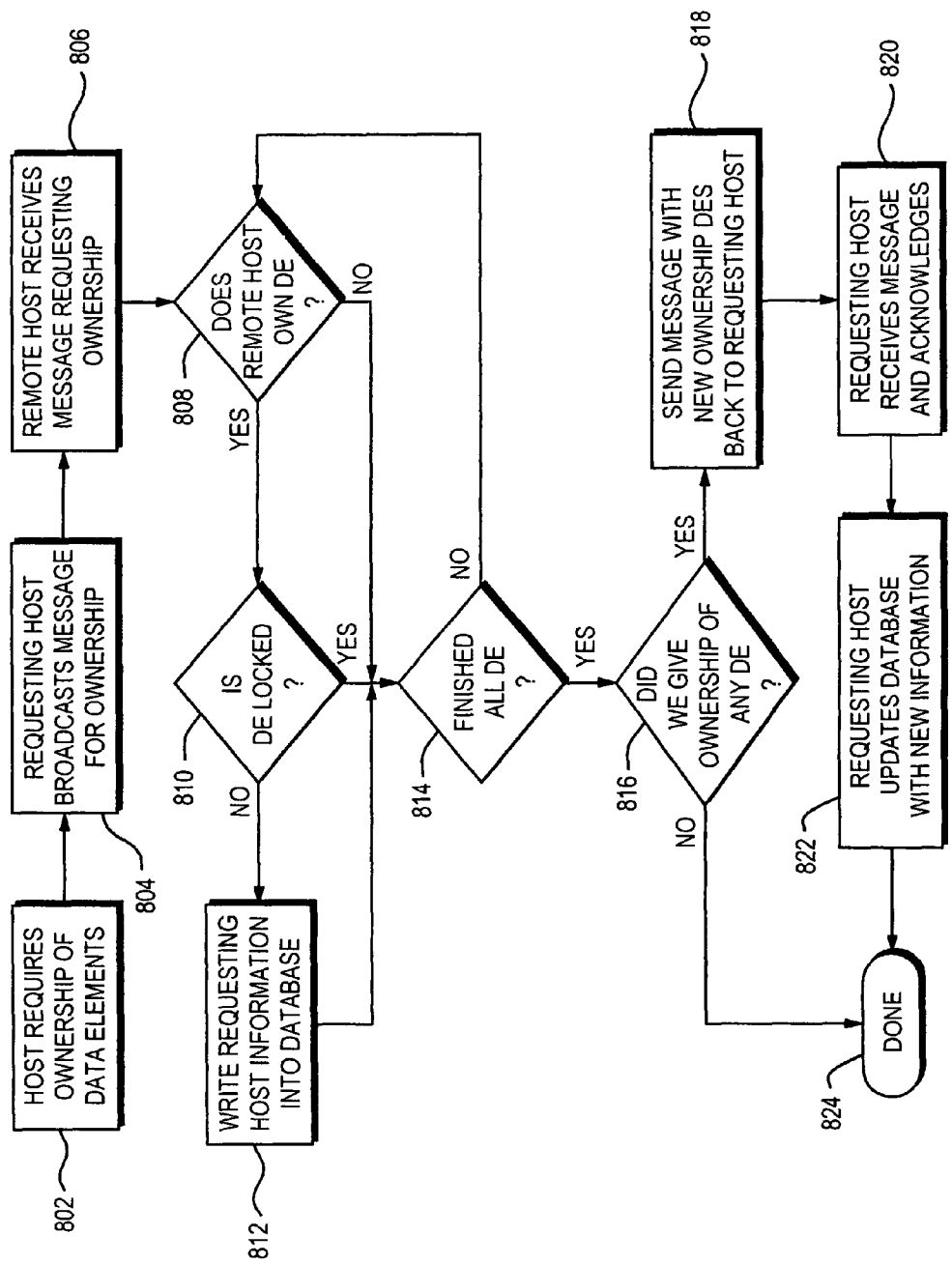
FIG. 8 is a block diagram illustrating a method for Host-Side Data Element Marshalling according to an illustrative embodiment.

In certain testing situations knowledge of data element location is imperative, such as when dealing with reagents. This situation may be addressed by host side data element marshalling. Referring to FIG. 8, a block diagram illustrating a host-side data element marshalling method 800 is shown and described as follows. When a host computer requires ownership of data elements (e.g. reagents), as shown in block 802, the host computer requests ownership of the data elements by broadcasting a UDP message to IPN 100 requesting ownership of the data elements, as shown in block 804. Each host computer on IPN 100 receives the UDP message, as shown in block 806, and determines if it currently owns the requested data elements, as shown in block 808. The host computer that owns the requested data elements then determines if the requested data element is locked, as shown in block 810. If the requested data element is not locked, then the host computer that owns the requested data element writes information about the requesting host computer into its data element database, including Host ID and Timestamp update, as shown in block 812, effectively transferring ownership of the requested data element to the requesting host.

Once this has been completed or if the host computer does not own the requested data element or if the data element is locked, the host computer determines if all requested data elements have been examined for ownership, as shown in block 814. If not, then blocks 808 to 814 are repeated until all requested data elements have been examined for ownership. If yes, then the host computer determines if ownership of any data elements were transferred to the requesting host computer, as shown in block 816. If not, then host-side data element marshalling method 800 is completed, as shown in block 824. If yes, then the host computer broadcasts the new ownership data elements to the requesting host computer using a TCP/IP message, for example, as shown in block 818. Upon receipt of the new ownership data elements, the requesting host computer sends an acknowledgement message back to the sending host computer, as shown in block 820. The requesting host computer then updates its database with new owner information including incrementing the owner version and resetting the Timestamp, as shown in block 822. Once this has been completed, host-side data element marshalling method 800 is completed, as shown in block 824.

It should be appreciated that this type of direct test ordering performed via HL7 allows for the data entry and labeling functions to be streamlined, thus increasing work flow productivity and quality control. It should further be appreciated that IPS 102 may communicate with LIS 104 and/or network of host computers 106 using standard TCP/IP protocols or any other method suitable to the desired end purpose, such as Internet, Ethernet, Wireless, Local Area Network (LAN), Wide Area Network (WAN), etc. Moreover, the data handled by IPS 102 may be comprised of many types, such as, but not limited to, staining protocols, bar code assignments, reagent dispenser information, user passwords, case management, stain requests from the LIS, staining status and result information sent back to the LIS.

As described above, at least a portion of the methods of FIGS. 6, 7 and 8 may be embodied in the form of computer-implemented processes and apparatuses for practicing those processes. Additionally, at least a portion of methods of FIGS. 6, 7 and 8 may also be embodied in the form of computer program code containing instructions embodied in tangible media, such as floppy diskettes, CD-ROMs, hard drives, or any other computer-readable storage medium, wherein, when the computer program code is loaded into and executed by a computer, the computer becomes an apparatus for practicing the techniques described herein. Existing systems having reprogrammable storage (e.g., flash memory) may be updated to implement the techniques described herein. It is contemplated that at least a portion of the methods of FIGS. 6, 7 and 8 may also be embodied in the form of computer program code, for example, whether stored in a storage medium, loaded into and/or executed by a computer, or transmitted over some transmission medium, such as over electrical wiring or cabling, through fiber optics, or via electromagnetic radiation, wherein, when the computer program code is loaded into and executed by a computer, the computer becomes an apparatus for practicing the techniques described herein. When implemented on a general-purpose microprocessor, the computer program code segments may configure the microprocessor to create specific logic circuits.

It should be appreciated that the network implemented for use with the system and techniques described herein may also allow IPS 102 the ability to provide a web interface to remote operators that may be used for reporting and status updates for network of host computer systems 106 and any laboratory instruments, such as first plurality of laboratory instruments 110 and second plurality of laboratory instruments 114.

An embodiment of a system described herein may use any one or more different encoding technologies to facilitate tracking and identification of slides, reagents and other elements. These technologies include any electromagnetic encodings such as may be used, for example, with optically readable characters such as bar codes, readable and/or writable RFID labels, infrared ID systems, and the like.

As an example, RFID technology may be used in connection with tracking slides, reagents, and the like, and in accessing and managing the information about these elements. An RFID-enabled label may be used in connection with a glass slide, specimen container, or other item or component that may be processed in an automated laboratory environment.

An embodiment may find advantages to using RFID labels over bar codes, as described elsewhere herein. One advantage of RFID labels over bar codes is that RFID does not require line-of-sight to read and write the tag data. Additionally, RF signals are capable of travelling through a wide array of non-metallic materials. Data may be simultaneously captured from many RFID labels within range of an antenna. RFID labels may be encased in different coatings making them extremely durable and able to be tracked through harsh production processes. Also, as described in more detail elsewhere herein, RFID labels are able to support read and/write operations. In an embodiment using writeable RFID labels, real-time information updates may be performed by writing to the RFID label as a tagged item moves through processing steps. In contrast to a bar code which, once printed cannot be re-used, the writeable RFID tags can be re-used with new data.

Figure 9:
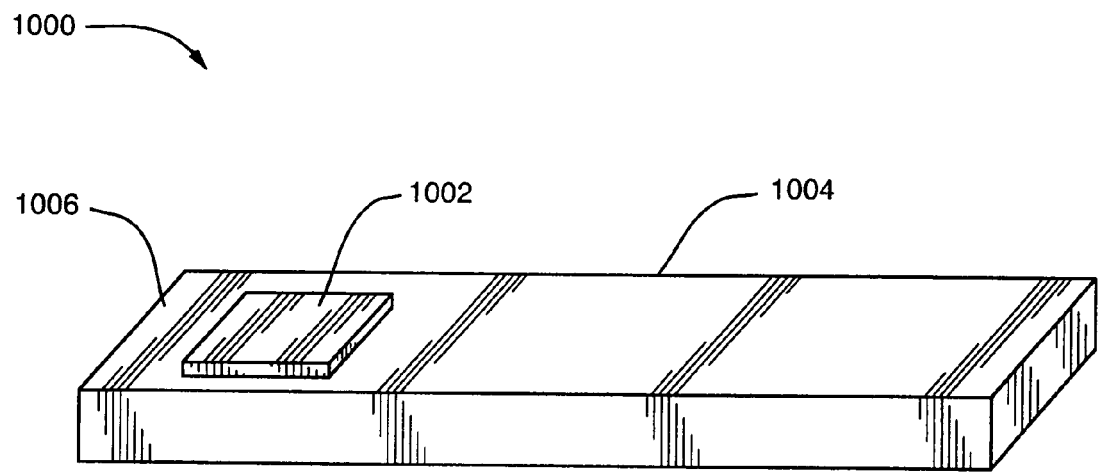
FIG. 9-12 are examples of embodiments of slide arrangements with RFID labels.

Referring now to FIG. 9, shown is an example of an embodiment 1000 of a slide arrangement. The slide 1004 includes an RFID label 1002. In the arrangement 1000, the RFID label 1002 is affixed to an upper face 1006 of the slide 1004. The slide in this arrangement and others described herein may be, for example, a glass slide. The RFID label 1002 may include information electronically encoded therein as described elsewhere herein. Additionally, a surface of the RFID label 1002 may include printed information such as, for example, human readable text, bar code identifiers, and the like. It should also be noted that an embodiment of an RFID label 1002 may omit the inclusion of text or other type of information on the surface thereof.

Figure 10:
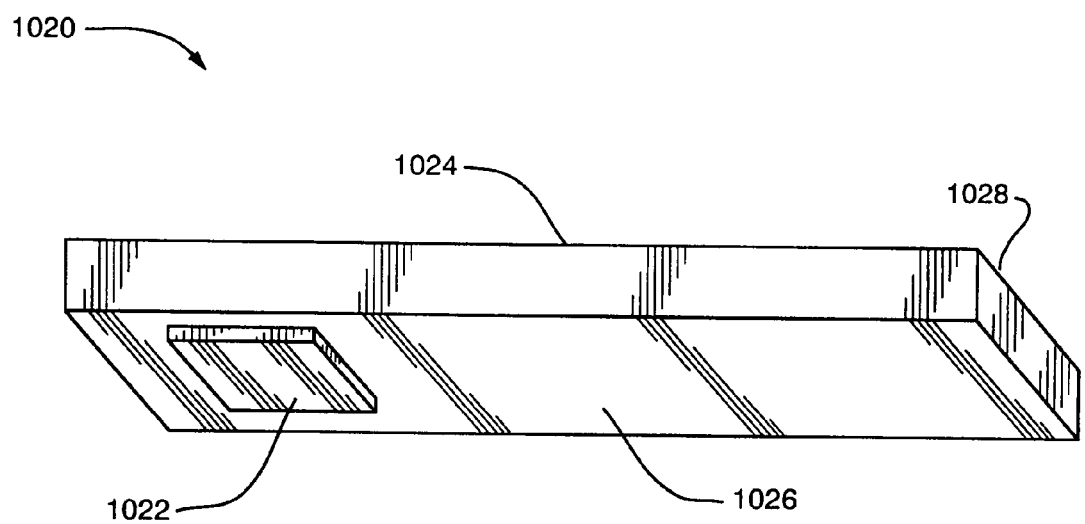

Referring now to FIG. 10, shown is a second arrangement 1020 of a slide and an RFID label. In the example 1020, the slide 1024 includes an RFID label 1022 affixed to a lower surface 1026 of the slide 1024. In this example arrangement 1020, the slide 1022 may include information encoded therein based on RFID technology as known to those of ordinary skill in the art. Additionally, on the surface of 1022 affixed to the bottom portion 1026 of the slide, the RFID label may also include information printed on a surface of the RFID label. The printed information may include human readable text, bar codes, and the like, which may be visible when viewing the slide 1024 from a top surface 1028. In this instance, the printed information such as the bar code may be on the surface of 1022 in contact with the bottom surface 1026 of the slide 1024. Additionally, an embodiment may incorporate text or other printed information on the bottom surface of the RFID label 1022. It should also be noted that an embodiment may include the bar code and other information in another label rather than including such optional text on a surface of the RFID label 1022.

Figure 11:
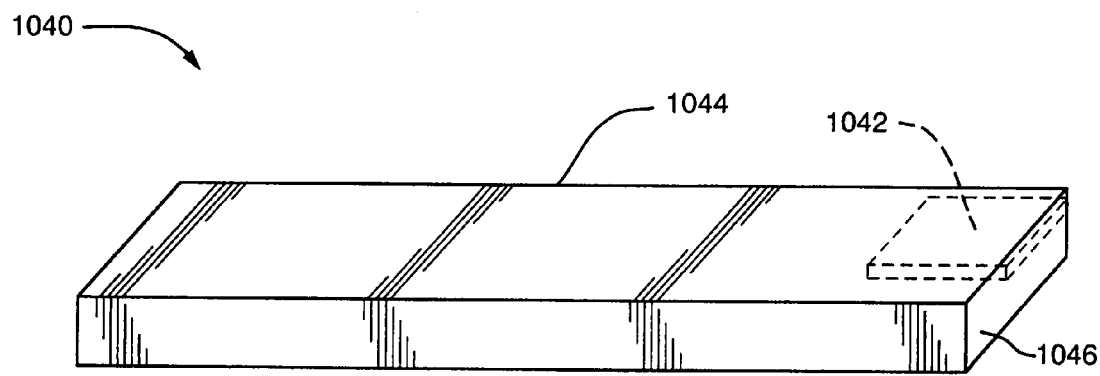

Referring now to FIG. 11, shown is a third arrangement 1040 of a slide in an RFID label. In the arrangement 1040, an RFID label 1042 may be embedded within a layer of the slide 1044. Such an arrangement 1040 may include a prefabricated slide and RFID label that may be provided, for example, by a vendor. In this arrangement, the RFID label 1042 is embedded near the top surface of the glass slide 1044.

Figure 12:
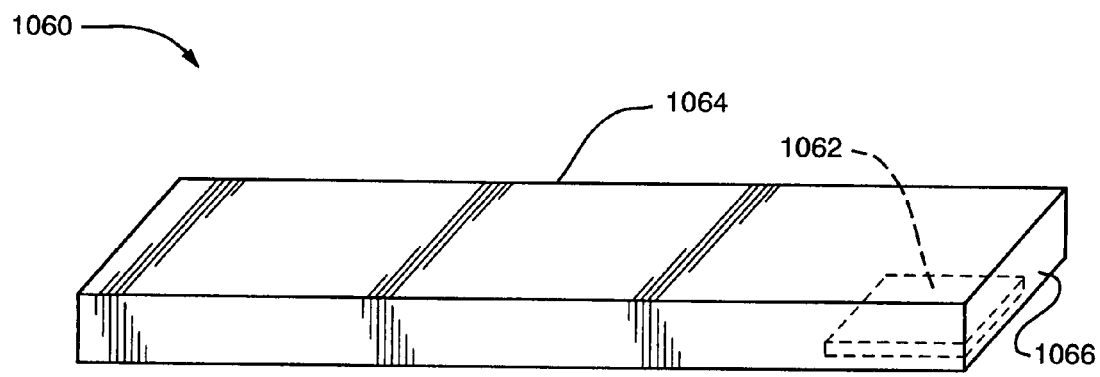

Referring now to FIG. 12, shown is a fourth arrangement 1060 of an RFID label and a slide. In the arrangement 1060, the RFID label 1062 is embedded near a bottom surface of the glass slide 1064. It should be noted that the arrangement shown in 1060 may be provided as a prefabricated slide and RFID label arrangement similar to that as described in connection with FIG. 11. The particular location within a slide at which the RFID label, such as 1042 and 1062, may be embedded may include other positions and locations than as described in connection with FIG. 11 and FIG. 12. The particular placement of the RFID label may vary in accordance with the particular slide composition and/or slide manufacturing process.

Figure 13:
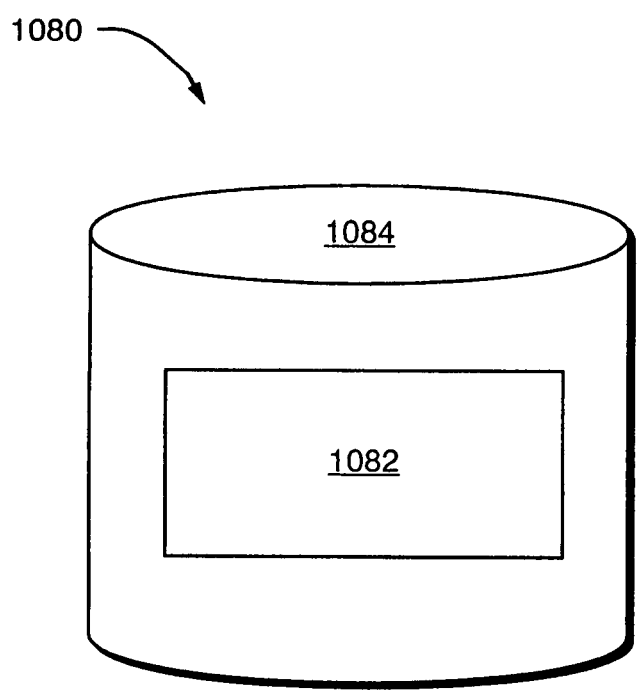
FIG. 13 is an example of an embodiment of a specimen container including an RFID label.

Referring now to FIG. 13, shown is an arrangement 1080 of a specimen container and RFID label. In the arrangement 1080, the specimen container 1084 may include an RFID label 1082 affixed to a surface of the specimen container 1084. The RFID label 1082 may also be in other locations than as illustrated in 1080 and may include additional information imprinted thereon similar to the other RFID labels as described elsewhere herein in connection with other figures. The RFID label may also be embedded beneath a surface of the container such as, for example, beneath a sidewall surface.

Figure 14:
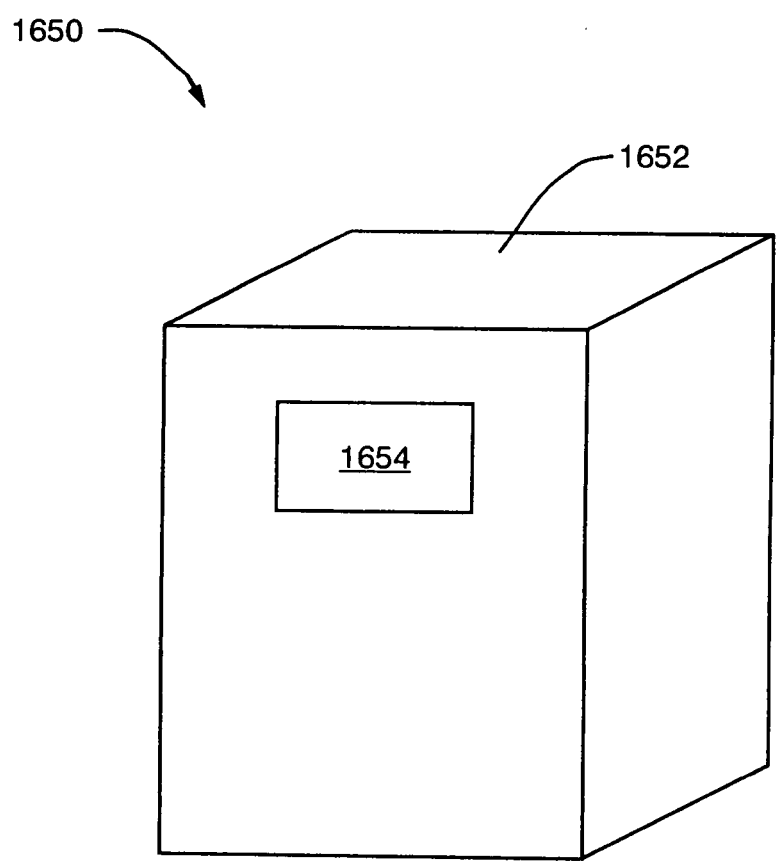
FIG. 14 is an example of an embodiment of a reagent container including an RFID label.

Referring now to FIG. 14, shown is an example 1650 of a reagent container including and RFID label affixed thereto. The example 1650 illustrates a reagent container 1652 that has an RFID label 1654 affixed to a side surface of the container. The RFID label 1654 may be placed on a different surface of the container than as shown in the example 1650. It should be noted that an RFID label may also be embedded in the reagent container beneath a surface of the container, such as, for example, may be performed when initially filling the reagent container. Such an embedded label may prevent misidentification of a reagent in the event that a subsequently affixed label to the surface of the container is removed or otherwise mixed up with another label placed on a surface of the container.

Figure 15:
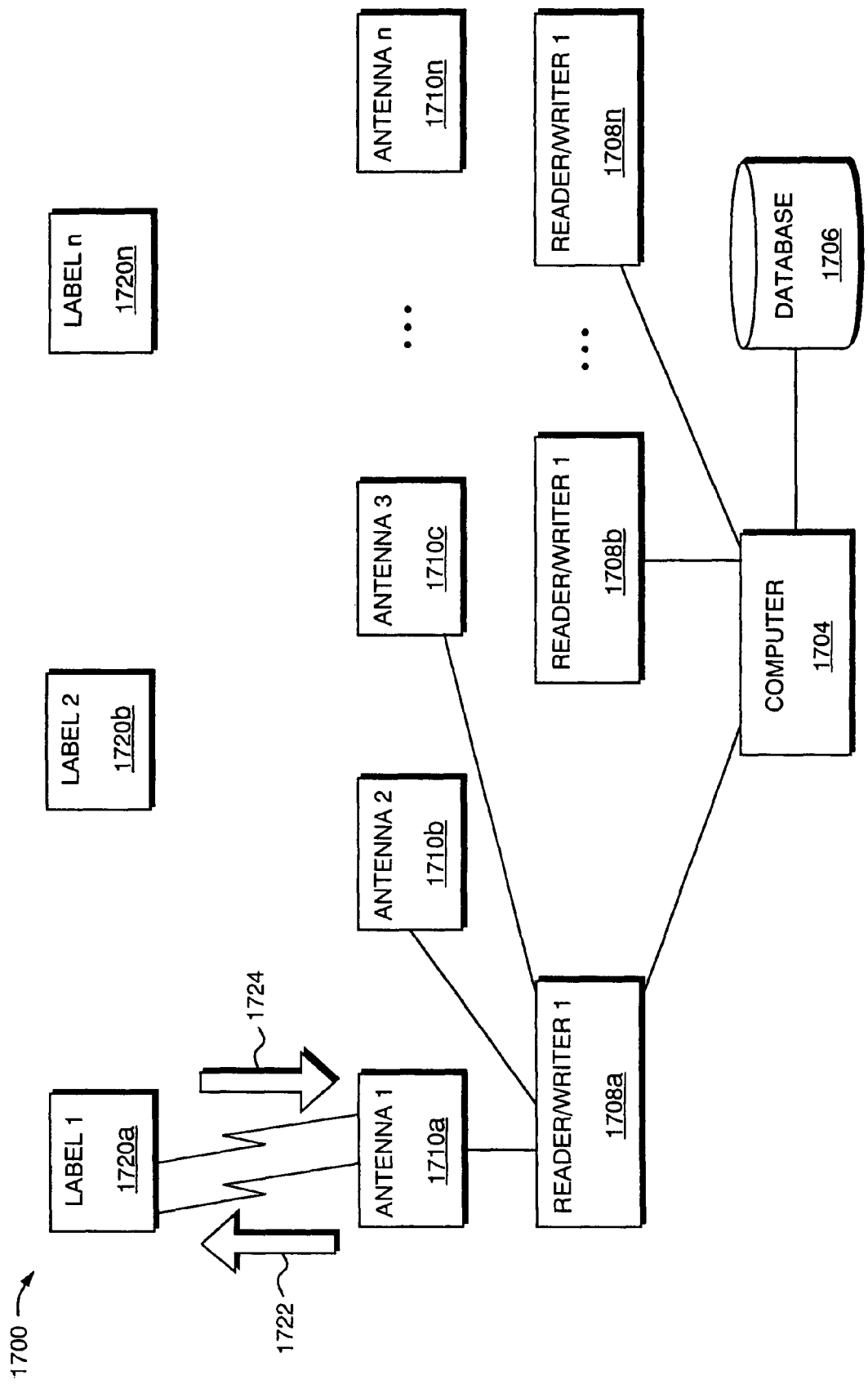
FIG. 15 is an example of components that may be included in a system using RFID labels.

Referring now to FIG. 15, shown is an example 1700 of components that may be included in a system using RFID labels. The components of FIG. 15 may be included in a laboratory and used in connection with other techniques described herein. The example 1700 includes a computer 1704, a database 1706, one or more RFID label reader/writer modules 1708a-1708n, one or more antenna 1710a-1710n, and one or more RFID labels 1720a-1720n. Each of the labels 1720a-n may be affixed to, embedded within, or other associated with, an element used in the laboratory as described herein. A label may be affixed to, for example, each slide and each reagent container. The RFID labels may be used in tracking and identifying the location of slides, reagent containers, and other elements to which the RFID labels are affixed thereto. In operation, an RFID label reader/writer module, such as 1708a, may interrogate one or more of the antenna elements regarding the location of a particular element identified by its RFID label. The module 1708a may do this by transmitting an interrogation signal to one or more of the antenna elements. An antenna element, such as 1710a, may transmit a signal to a label as illustrated by 1722. A label, such as label 1720a, receives this signal and may transmit back a return signal, as illustrated by 1724, which includes a unique identifier corresponding to that RFID label. The module 1708a may obtain (read) this RFID label's unique identifier and other information through this technique. The computer 1704 may communicated with the modules 1708a-1708n to send and/or receive data which may be stored in the database 1706.

It should be noted that computer 1704 may be, for example, a host or another computer system connected to the IPS. The IPS is included in examples described elsewhere herein such as, for example, in FIG. 3, FIG. 29, and FIG. 33. In one embodiment, for example, the element 1704 may be a host computer. The host may be connected to the RFID reader/writer components as illustrated in FIG. 15. The same host which communicates with the read/writer components may also communicate and control other instruments, such as laboratory instruments. Alternatively, an embodiment may have a dedicated host which does not control laboratory instruments in addition to the RFID components, such as the reader/writer components illustrated in FIG. 15. One or more of the read/writer components may be standalone components as illustrated in FIG. 15. An embodiment may also include one or more of the read/writer components within another instrument. The host may gather the information from the RFID labels or tags. For example, the host may execute code that processes inventory usage and performs RFID event handling. Subsequently, the host may also communicate with the VLM and other components in the laboratory to disseminate any such information gathered via the RFID labels and interrogation thereof. As described elsewhere in more detail information may also be written to the RFID labels using the host.

As also described elsewhere herein, the RFID labels or tags may be encoded, or have information written to the RFD labels. The information included in the RFID labels may be dynamically modified as the label moves through laboratory processing. In contrast to barcodes which contain static information that may identify a record or group of records in a database, RFID labels allow data to travel along with an associated element, such as a slide. Processing may be performed both inside and outside of the laboratory using the data stored on the RFID label, for example, to know how to process the slide associated with the RFID label, and then store other information into the RFID label. In this manner, an embodiment may use the RFID labels as a source of information and the database, for example, may be characterized as a redundant cache or copy of some or all the data that may otherwise be included in the RFID label.

As known in the art, RFID labels may be active or passive. Further, RFID labels may be read-only, write once/read many, and read/write. Any one or more of the foregoing may be included in an embodiment.

Different techniques may be used to determine the location of an RFID label. For example, an embodiment using triangulation to determine the location of an RFID label may use at least three antenna modules. If RFID labels are located on slides stored in a shelving arrangement, antennae may be installed so that each antenna may be responsible for determining the location of slides in one or more particular zones or portions of a shelf. It will be appreciated by those of ordinary skill in the art that the particular arrangement, number, type and orientation of antennae may vary with each embodiment. The antennae may be placed in order to facilitate tracking of, and communication with, the various elements including RFID labels. It should be noted that the antennae may be arranged to provide for locating an individual RFID tag by triangulation techniques within a required accuracy for a particular application and embodiment.

As illustrated above, an RFID label may be affixed or otherwise embedded on a slide, sample, or other element. By affixing or embedding an RFID label, information may be written to and/or read from the RFID label as a slide is processed in connection with the laboratory workflow associated with the processing. As an example, an RFID label may be affixed to a slide at the time a specimen is cut. The patient information and the test to be performed may be encoded by writing to a writeable RFID label. As an alternative to writing some or all of the information to the RFID label, the RFID label may also provide an index similar to the identifier of a bar code label, and the index may be used to indirectly obtain information from a database or other data container. The surface of the RFID label, or other portion of the slide, may include other printed information, such as text, bar code information, etc. The printed information may include a portion of the RFID encoded information and/or other information. As the slide moves through the laboratory, the slide may be checked using any one or more of a variety of techniques to ensure proper processing of the slide at each point. The information obtained at each point may include, for example, the particulars related to a test or processing step to be performed. Such techniques used to read the information may include a technician visually inspecting the slide by reading the text portions thereon, using a bar code reader, using an RFID reader, and the like. As the sample moves through the laboratory processing steps, the slide's RFID label may be encoded with additional information such as, for example, time, date, test parameters, and other information that may be used in connection with quality assurance and control. This information may be written to a writeable RFID label. It should be noted that information may also be added to the database of the host which duplicates some or all of the information in a writeable RFID label. As a QC check, at different points in processing, portions of the information obtained through reading an RFID label may be compared to information stored in a host's database as replicated elsewhere in the system.

The information written to a writeable RFID label may vary with an embodiment. For example, an embodiment may write information in accordance with specified regulations which may be used in the event that a QC failure is detected. Additionally, the information written to the RFID label may be used in determining such a QC failure as well. As an example, such information written to the RFID label may include one or more of the following: information of reagent used (e.g., a catalog number, lot number and expiration date used with a tissue sample)), control information such as information used to characterize staining benchmarks on control tissue samples, chain of custody tracking information (e.g., batch information, where this sample has been processed in the laboratory, by what instrument, when), technician information (e.g., name of technician examining sample, operating instrument, inspecting instrument, physically inspecting sample to ensure that RFID label and sample match and that the RFID label is not separating away from the slide or other associated element), observations of conditions that may be of interest to a pathologist or other person as may be used in connection with ensuring a proper diagnosis.

When the slide reaches the pathologist after slide testing is complete, the pathologist may access any of the encoded information in the RFID label and may further record a diagnosis for that sample. The diagnosis may be recorded by writing to the RFID label and/or writing the data to a database. The information encoded in the RFID label provides a pathologist or other location that may be offsite from the laboratory access to sample information that may otherwise only be accessible with a connection to a database or other data container including information about the sample.

Figure 16:
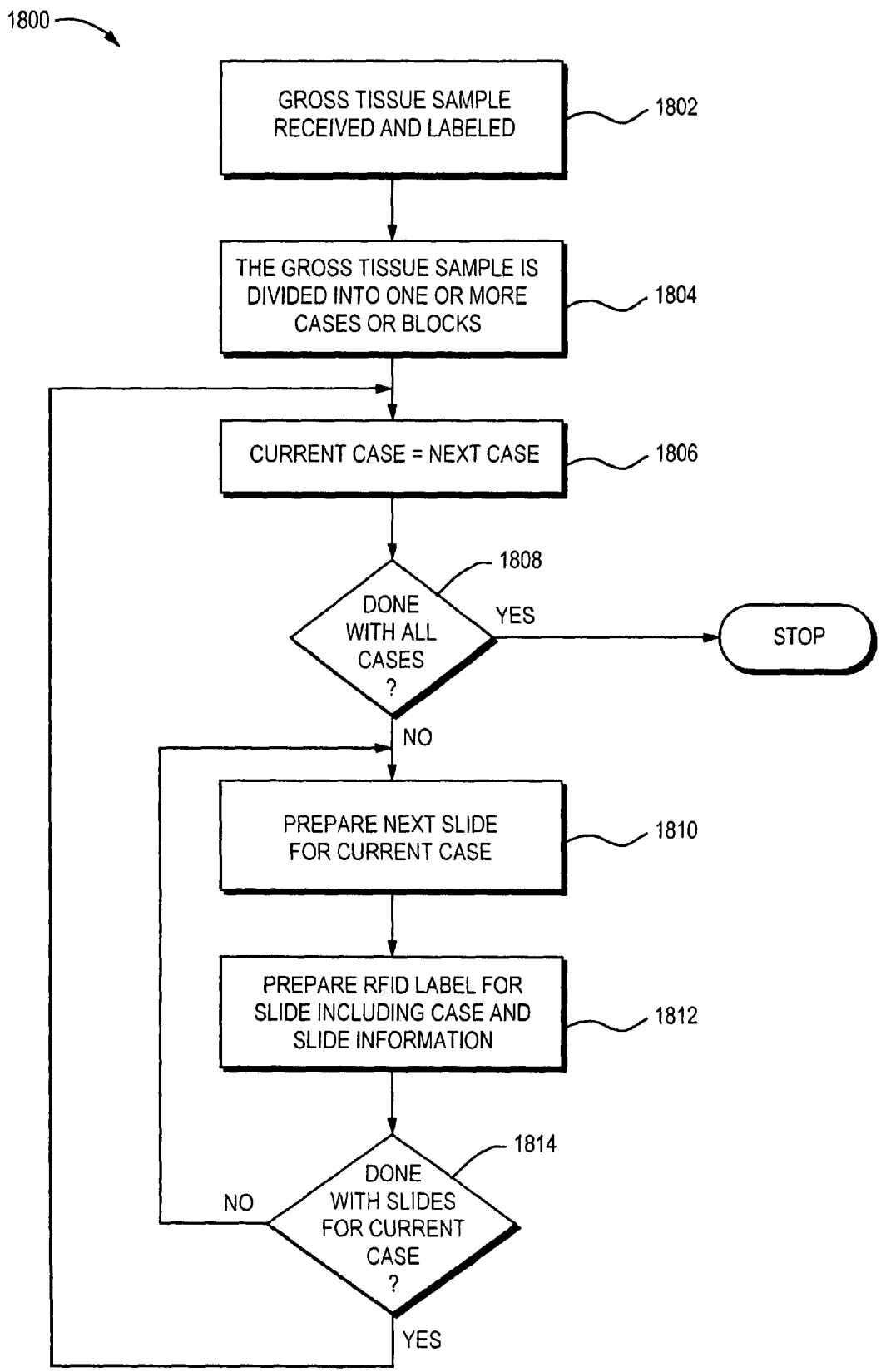
FIG. 16 is a flowchart of processing steps that may be performed in an embodiment in connection with preparing RFID labels for tissue samples.

Referring now to FIG. 16, shown is a flowchart 1800 of processing steps that may be performed in an embodiment in connection with RFID labels. The steps of 1800 summarize those described above. At step 1802, a gross tissue sample may be received at a laboratory and may be affixed with an RFID label. The gross tissue sample at step 1804 may be divided into one or more cases or blocks. At step 1806, current case is a variable that represents the current case being processed. At step 1808, a determination is made as to whether all cases are processed. If so, slide preparation stops. Otherwise, control proceeds to step 1810 to prepare the next slide for the current case. At step 1812, the RFID label for the current slide is prepared including the case identifier and slide specific information. The case identifier may be used, for example, to later retrieve all slides of a particular case. Similarly, a unique identifier associated with the gross tissue sample may be used in connection with determining all slides associated with a particular tissue sample. Step 1812 may be performed by writing the information to a writeable RFID label. Step 1812 may also be performed using a read-only RFID label that is produced on-site at step 1812 and then affixed to the slide. At step 1814, a determination is made as to whether processing of all slides for the current case is complete. If so, control proceeds to step 1806 to process the next case. Otherwise, control proceeds to step 1810 to prepare the next slide for the current case. It should be noted that the steps of 1800 may be performed manually and/or in an automated fashion, such as with an automated slide preparation apparatus. In the event that one or more of the steps of 1800 are automated, software and/or hardware may be used to issue instructions to control the particular component performing the steps. It should be noted that the processing steps of 1800 may be performed using writeable or non-writeable RFID labels.

Figure 17:
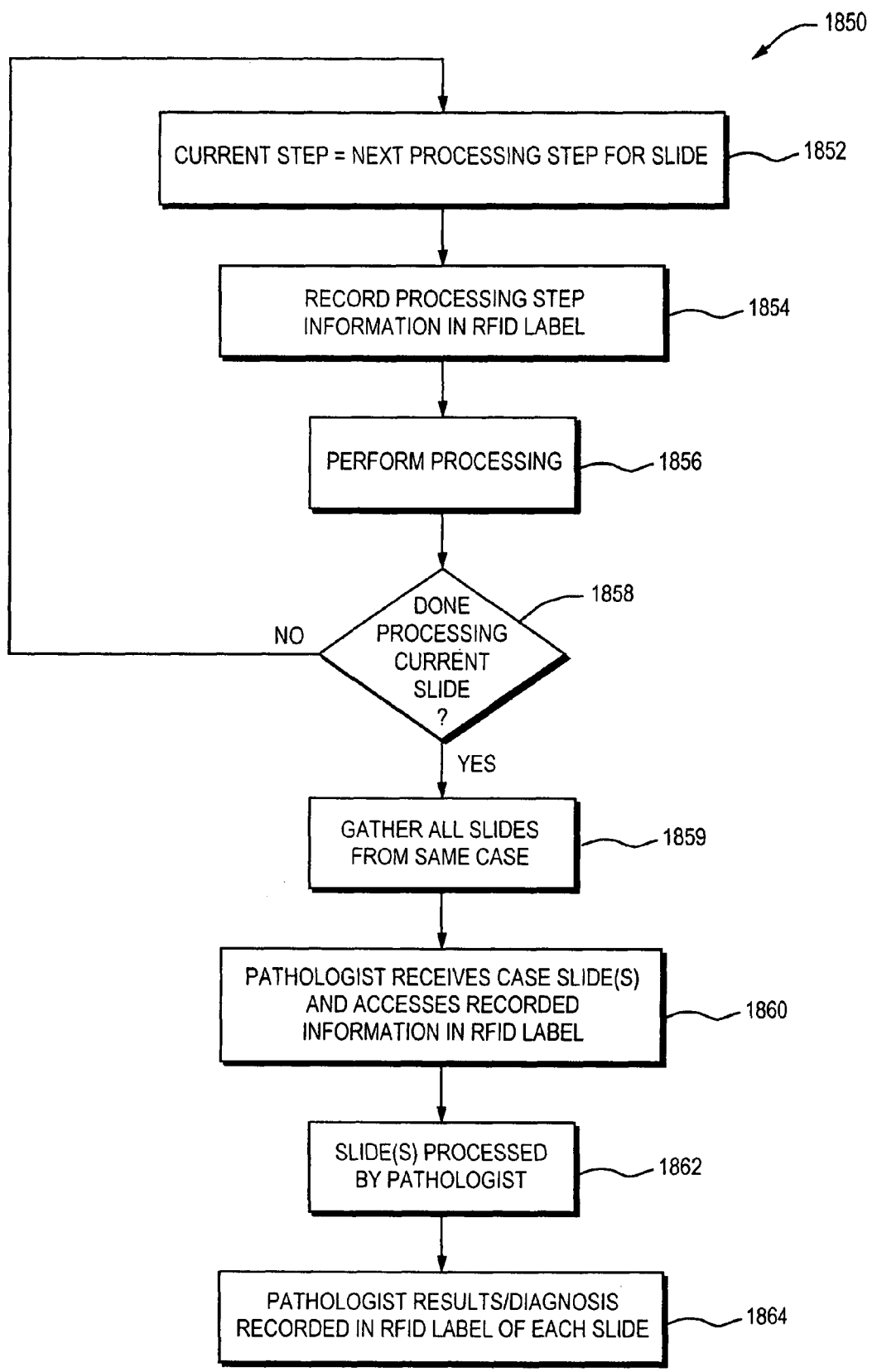
FIG. 17 is a flowchart of processing steps that may be performed in an embodiment in connection with processing prepared slides using RFID labels.

Referring now to FIG. 17, shown is a flowchart 1850 of processing steps that may be performed in connection with processing prepared slides including writeable RFID labels. The steps of 1850 may also be performed manually and/or in an automated fashion. For example, in the event that the slides are to be stained, the steps 1852, 1854, 1856, and 1858 may be performed using one or more automatic staining apparatus. At step 1852, a variable current step represents the next processing step for the current slide. At step 1854, processing step information is written to the RFID label. This information may include, for example, date/time information, the reagent used, information about the reagent such as batch number, lot number, etc. The information written may vary with each processing step. For example, one processing step may be to take an image of a resulting stain and store the resulting image in a file, such as a JPEG file. An identifier of the location of the resulting image file may be written to the RFID label. As described elsewhere herein, the slide identifier and other slide information associated with the data element may be stored in the OBX segment as described elsewhere herein. At step 1856, the current processing step for the slide is performed. At step 1858, a determination is made as to whether processing of the current slide is complete. If not, control proceeds to step 1852. Otherwise, control proceeds to step 1859 where the slides of a same case may be gathered. Step 859 may be performed after one or more runs of slides have been processed on one or more instruments. The RFID label of each slide included in a particular case may be used to perform step 1859 by sending out interrogation signals to determine all RFID labels with a particular case identifier. After all the slides of a same case have been gathered, the pathologist receives the one or more slides associated with the case at step 1860. It should be noted that step 1860 may happen at some time period after one or more slides of a case have been processed. At step 1860, the pathologist receives the one or more slides and accesses recorded (written) information in the RFID label. At step 1862, the pathologist processes the slide. Any subsequent results or diagnosis by the pathologist may be written to the RFID label at step 1864. As described elsewhere herein, the results or diagnosis being recorded in the RFID label and/or database may trigger a status update to be communicated. In an embodiment which uses non-writeable RFID labels or bar code labels, processing steps of 1850 may be varied so that processing information is recorded in a database rather than written to the RFID label, such as at steps 1854 and 1864.

RFID labels may be used to track and/or collate slides associated with a particular case or batch in connection with other processing steps than as illustrated for purposes of example above. As another use of the case identifier in collating, a first set of staining may be performed on a group of slides. At some later point, the slides may be subjected to additional staining or other processing. RFID labels may be used to locate all slides of a particular grouping which may be temporarily stored between processing steps, such as staining, imaging, and other steps.

In connection with recording information at steps of 1800 and 1850, it should be noted that information may be recorded in other locations besides the RFID label. For example, information may also be recorded in the database of the IPS 102 and one or more of the hosts. As additional data is written to the RFID label, the additional data may be stored in the database of the IPS 102 through subsequent interrogation of the RFID label. Further replication of these data updates may be made to other databases of other hosts using techniques described elsewhere herein.

By recording order, processing, and/or result information about each slide on the associated slide or other specimen using writeable RFID labels, each slide carries with it various pieces of identifying information. The information may be used to identify each sample or specimen in the laboratory. Such information may provide an added check, for example, in identifying one or more samples of a single batch of case cut from an initial specimen. Use of the writeable RFID labels may provide for quickly accessing and identifying up to date information about a sample locally with only access to the sample itself. As also described above, an RFID label may be used in physically identifying a location of one or more stored slides without requiring the slide to be within line of sight. Such identification may be performed, for example, to verify if a slide, reagent, and the like, is physically resident at a location as may be expected, such as, for example, as identified in a database record field, verifying if the slide is/is not within the physical site of the laboratory.

An embodiment may also utilize an RFID label in connection with only reading data therefrom. Such an embodiment may use an RFID label similar to a bar code in which data included in the RFID label remains static. However, such an embodiment still has advantages over bar codes and other forms of encodings, such as optical readers or electromagnetic scanners requiring that the RFID label be within line of sight of the reader or scanner. Information may be read from the RFID label without being subject to such restrictions. The RFID label may be conveniently read from other locations within the laboratory with restrictions in accordance with the antenna and other equipment of the RF system.

RFID labels may be used in connection with, or as an alternative to, other types of manual and/or automated techniques. For example, RFID) labels may be used in combination with bar code labels. It should be noted that an embodiment using writeable RFID labels to dynamically store information, for example, as a result of processing a slide or other sample, may omit some or all of the information stored in the database. This may be used to reduce storage requirements on one or more of the hosts and/or IPS databases or other data containers.

In one embodiment, glass slides may be provided with a label on the slide when a sample is placed thereon. The slide, for example, may be provided for sale by a vendor with an RFD incorporated into each slide at the time of sale. Alternatively, a vendor may also provide an automated slide labeling system which may be used in placing RFID labels on the slides at other points.

The RFID label may also serve a functional purpose in connection with the slides. For example, in one embodiment, the label may serve as a "dam" on the slides for a sample stored thereon.

In an embodiment using a writeable RFID label, what will now be described is an example of data that may be encoded in the RFID label. The data that is described may be used to generate a pathology report sent to the LIS in connection with a pathology test. Other data than as set out below may also be encoded in the RFID label in accordance with the one or more report formats may be used in an embodiment. As described herein with reference to FIGS. 3 and 3A, the VLM, which is executing on the IPS, may gather one or more data elements from one or more hosts and provide them in a report format to be sent to the LIS. The following information may be encoded in the RFID label for inclusion in the pathology report sent to the LIS:

Patient Demographics
Patient Name
Date of Birth
Hospital Accession Number
Specimen Site
Date Collected
Referring Physician
Results Summary
Test Name
Staining Intensity
% cells Positive
Case Summary Report The Case Summary Report may include, for example, photos or images and summary information for any assay run.

It should be noted that use of RFID technology for object tracking and identification is described, for example, in U.S. Pat. No. 6,150,921, Article Tracking System, Werb et al., Nov. 21, 2000, and U.S. Pat. No. 6,600,420, Application for a Radio Frequency Identification System, Goff et al., Jul. 29, 2003, both of which are incorporated by reference herein.

In connection with encoding information that may be read optically from labels of slides, reagents, and the like, different types of characters or glyphs and associated symbologies may be used. One way of encoding information which may be read optically is using bar codes. Bar codes may be characterized as parallel arrangements of varying bars and spaces. Additionally, bar codes may also include symbols expressed as width modulated symbols and height modulated symbols. Bar codes may be of varying dimensions and other varying physical attributes as described elsewhere herein and known to those of ordinary skill in the art. In connection with the width modulated symbols, a parallel arrangement of varying width bars and space may be used to represent a symbol. Similarly in connection with height modulated symbols, a parallel arrangement of varying height bars may be used to represent a particular symbol. A symbology describes how information may be encoded into physical attributes of bars, spaces, and other optically read characters. Symbology also refers to a set of rules for a particular type of code. For example, in connection with bar codes, bars may be thought of as darker elements of the symbols whereas spaces are characterized as the lighter portions there in between. Any one of a variety of different symbologies as may be included in standard, or in vendor specific, definitions may be used in an embodiment to represent a bar code.

It should be noted in connection with codes, such as bar codes, as known to those of ordinary skill in the art, reading and printing equipment use a compatible symbology so that a device reading a bar code of a first symbology is capable of understanding and interpreting the first symbology as may be produced, for example, by printing equipment producing labels in the first symbology. A bar code or other type of character may be used to encode information. Such information that may be encoded may include, for example, a part number, a serial number, a transaction code, an index into a database, or other type of data. A symbol as used herein in connection with bar codes or other codes may refer to the actual arrangement of characters such as parallel bars, spaces, and the like, used to encode information.

Techniques for encoding information, as may be used in connection with optical detection in an automated laboratory environment, are known in the art and described, for example, in U.S. Pat. No. 5,449,895, to Hecht et al., entitled Explicit Synchronization for Self-Clocking Glyph Codes, which is incorporated by reference herein, and *The Bar Code Book: Comprehensive Guide to Reading, Printing, Specifying, and Applying Bar Code and Other Machine-Readable Symbols*, by Roger C. Palmer, Revised and Expanded Fourth Edition.

Figure 18:
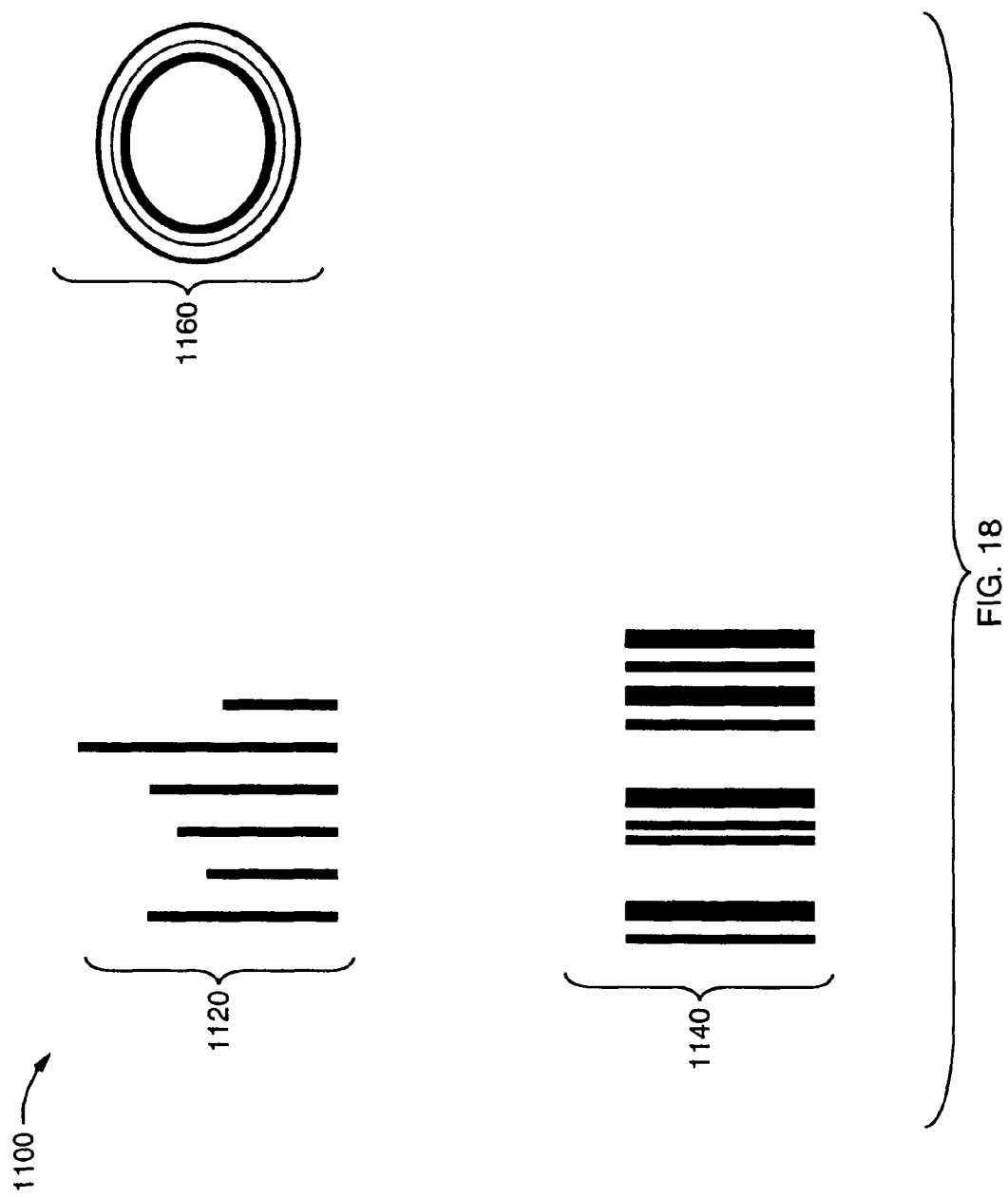
FIG. 18-22 are example representations of different types of codes that may be used in connection with encoding information in labels.

Referring now to FIG. 18, shown are some example representations of embodiments of different types of bar code symbologies that may be included and used in connection with the techniques described herein. FIG. 18 includes a first linear bar code symbology 1120. In the representation 1120, single rows of bars and spaces may be varied with height modulation to encode data. Referring to element 1140, shown is a bar code symbology where width modulation of the linear symbols is illustrated. In connection with the representations 1120 and 1140, different linear symbologies may use the combination of both the width modulation and height modulation techniques in order to encode data. The different patterns represented by the different bar codes of varying widths and/or heights may be used to represent different characters corresponding to encoded data. Referring to element 1160, shown is an example of a circular symbology representation. By varying the width of concentric circles, different characters may be represented.

Figure 19:
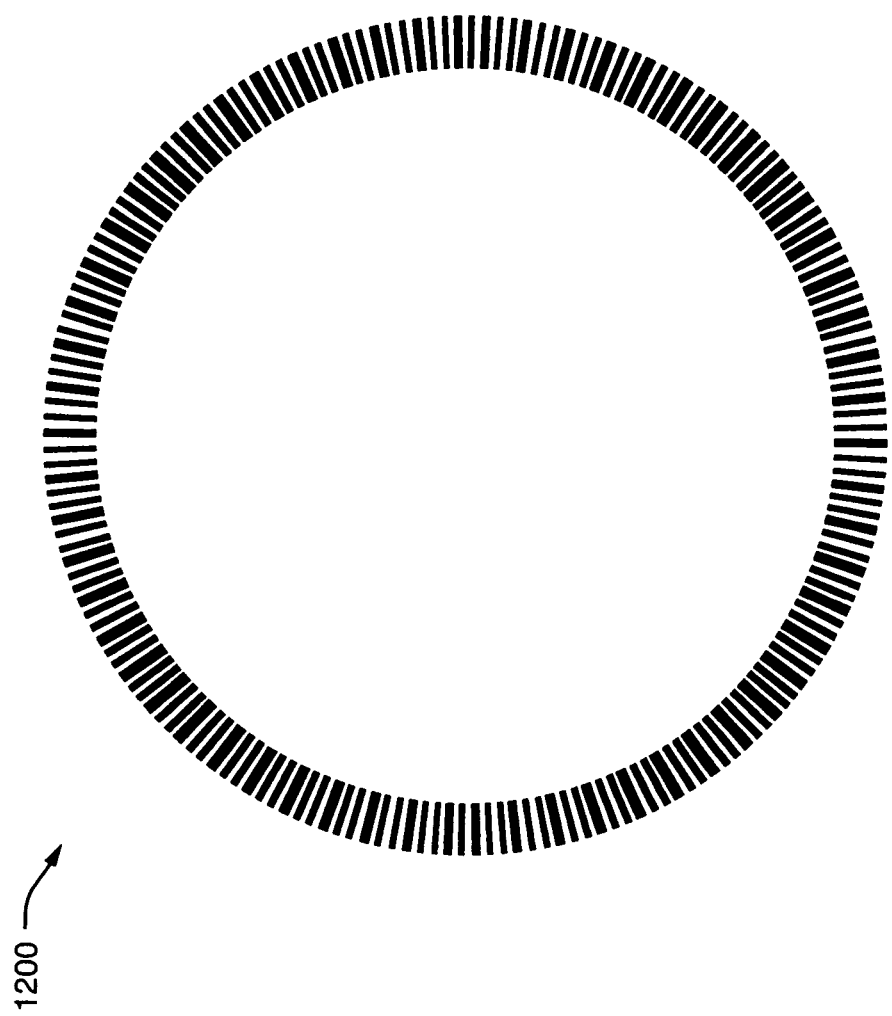

Referring now to FIG. 19, shown is an example 1200 illustrating another circular symbology. The circular symbology in 1200 represents a circular arrangement of linear symbologies or segments thereof used to represent one or more different characters and encodings.

In connection with both the linear symbologies illustrated in 1120 and 1140 and the circular symbologies illustrated in connection with 1160 and 1200, one or more characters may be represented by one or more of the corresponding detectable symbols which may be represented, for example, as a linear element or as a circular element. One or more of the linear or circular elements may correspond to a particular character representing an encoding. More generally, each of the different optically detectable symbols, such as a line or a circle described above, may be referred to as a glyph. The techniques of bar coding as known to those of ordinary skill in the art rely upon the order of the glyphs as may be detected, for example, by an optical reader in which a specified ordering of the glyphs represents encoded data.

Figure 20:
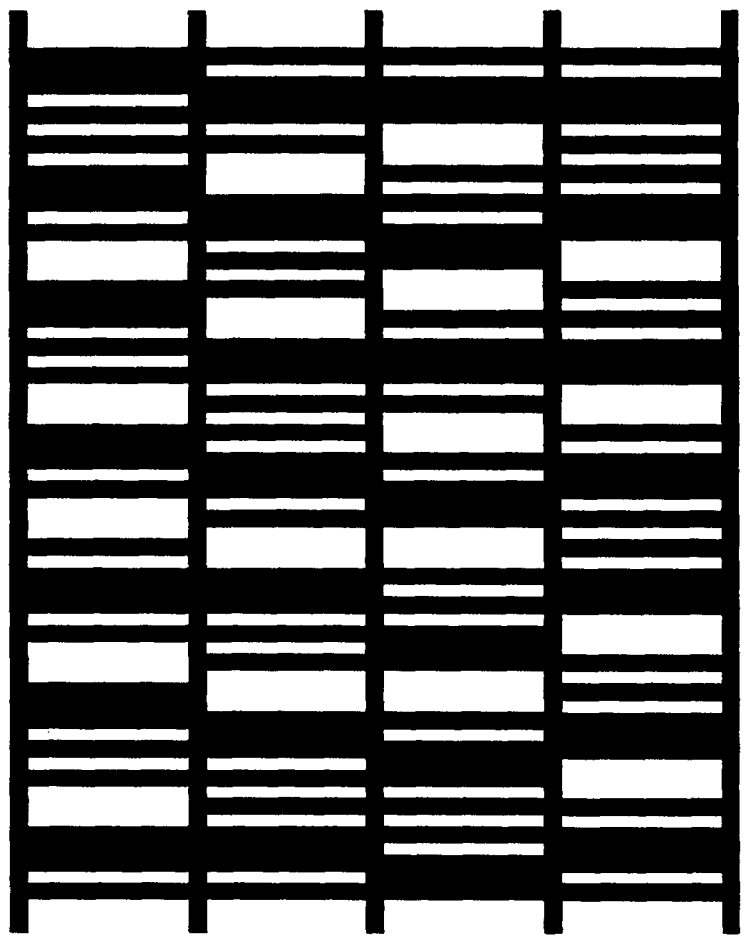

In connection with the use of bar codes, other types of symbologies may also be used. Referring now to FIG. 20, shown is a representation 1220 of a two dimensional (2D) stacked bar code symbology. In a 2D stacked bar code symbology, multiple rows of width modulated bars and spaces are used to represent one or more characters. Each row is the same physical length and looks like conventional linear symbology. Adjacent rows touch each other and may include separator bars for delineation. In connection with the representation 1220, multiple rows of linear bar codes are stacked together to form a single symbol. The representation 1220 may correspond to a single symbol.

Figure 21:
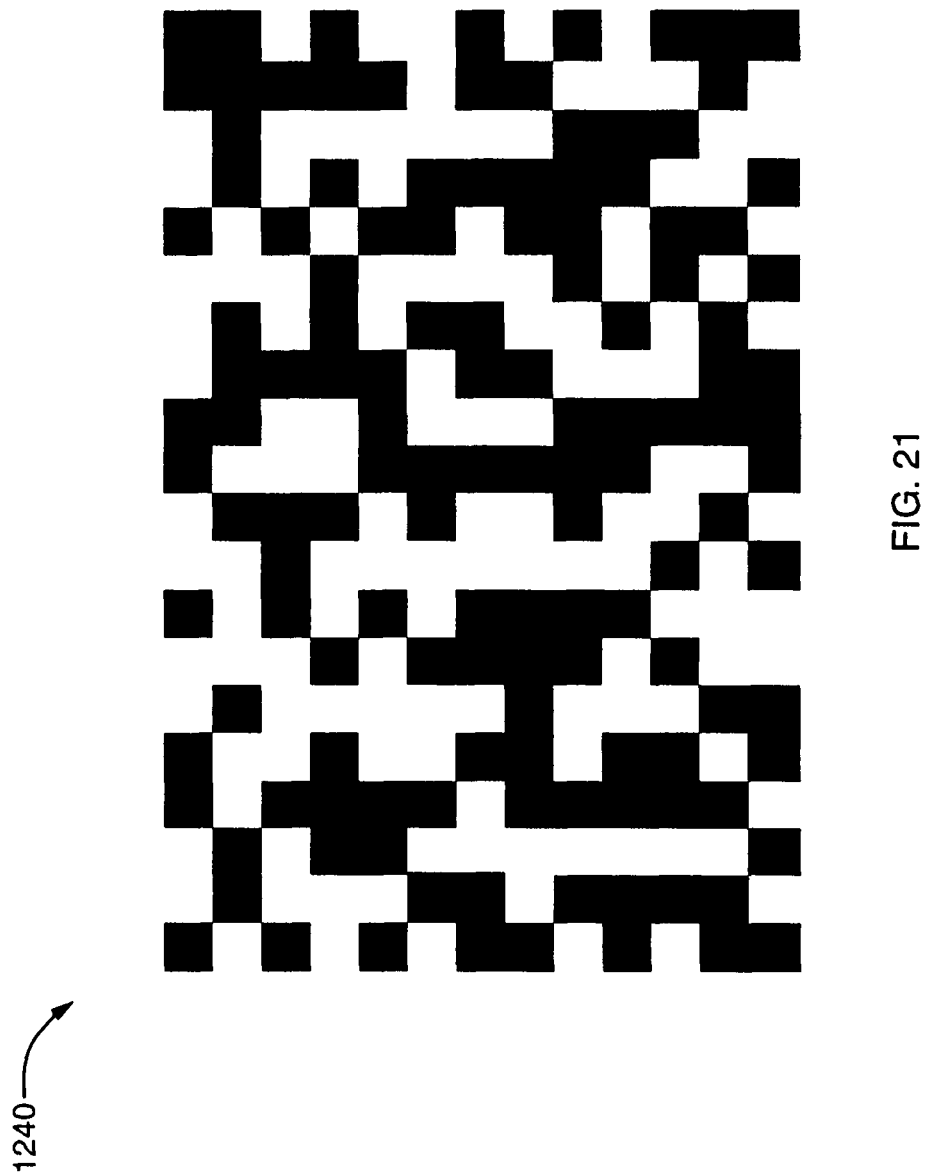

Referring now to FIG. 21, shown is an example 1240 representing a two dimensional matrix symbology used to encode information into a two dimensional pattern of data cells. The data cells may have different colors, such as black or white, and different shapes, such as squares dots or polygons, which may be separated by spaces containing no information.

It should be noted that although 1-D and 2-D bar code arrangements are described herein, bar codes may be of other higher dimensions (e.g., 3D, etc.) in accordance with the particular bar code readers and printers in each particular embodiment.

Different types of characters may be encoded in accordance with different symbologies. For example, a symbology may encode only numbers. Other symbologies may encode alphanumeric information and others may provide encoding for the entire ASCII character set as well as a range of user defined characters, printable characters, and the like. Different symbologies may be used in representing different character sets encoded, such as, for example the character sets used for different foreign languages. An optical reader may also recognize other types of characters or glyphs besides the foregoing bar-like codes.

Figure 22:
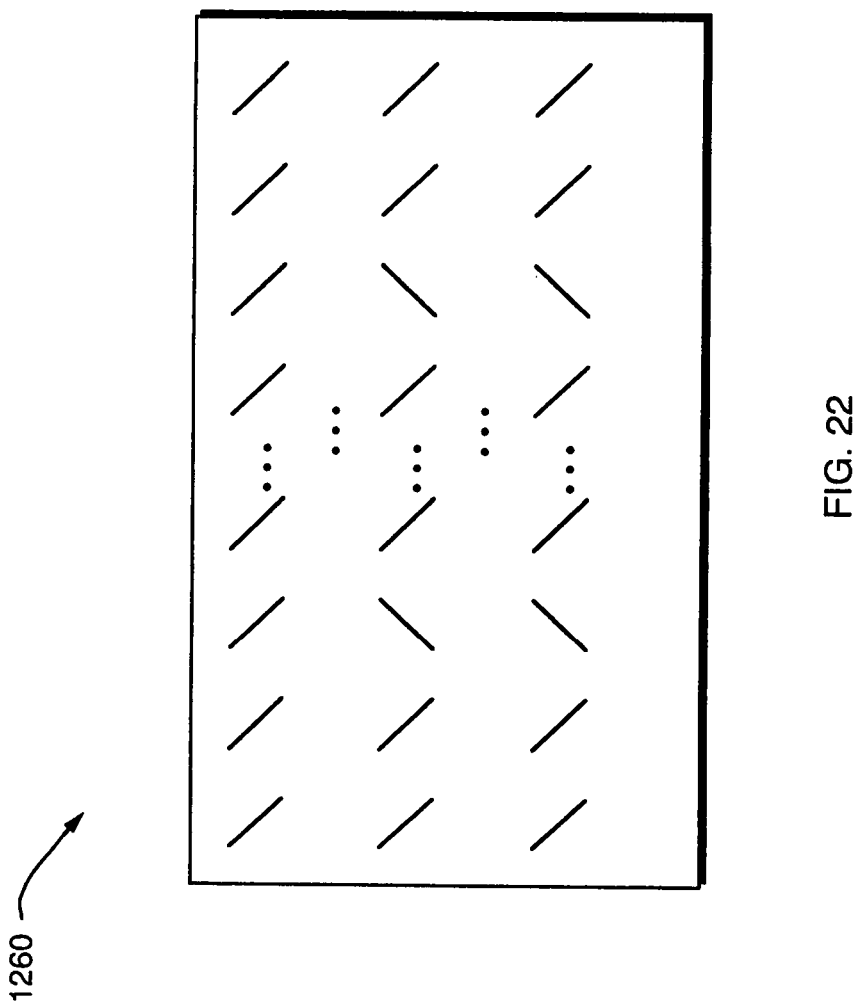

Referring now to FIG. 22, shown is a representation 1260 of glyph codings that may be used to represent encoded information. It should be noted that the representation in FIG. 22 includes as glyphs slash-like symbols rather than bars where the slash-like symbols are oriented at different 45° angles with respect to a vertical axis. Each of the different slash-like symbols may correspond, for example, to the values of one and zero. The different varying patterns of ones and zeroes may correspond to an encoded character or data. A symbol may be represented by a predefined number of these slash-like symbols defining an array that may be characterized as a symbol cell. For example, an array may be defined to the size of the number of bits representing a character in a particular character set, such as the ASCII character set. A different array size may be appropriate for representing other character sets. The foregoing is another representation of how optically detectable characters may be used to encode information.

An embodiment may use any one of a variety of different symbologies and characters which may be optically read and/or recorded (e.g., such as by printing) in connection with encoding information. The recorded data may be included on a graphic recording media, such printed on paper, which may then be used as a label for a slide or other specimen.

What will now be described are examples of different arrangements in which labels including optically readable characters may be used in a laboratory as described herein. Although bar codes are used, it should be noted that other types of characters and different symbologies may also be used. The particulars of the following examples should not be construed as a limitation.

In an anatomical pathology laboratory, as an example, a bar code on a slide may be used in connection with accessing a common set of data that may be stored in one location or duplicated at various sites. In one embodiment, the bar code identifier associated with a slide may be a globally unique identifier used in accessing the data elements associated with that slide. The slide's unique identifier may be formed so that the identifier is unique with respect to slides that may be processed by the laboratory for a time period of years. As such, the slide's unique identifier may be formed, for example, based on at least partial date information. As described herein with reference to FIG. 3, use of the VIP provides for connections to an LIS from instruments, other hosts, and other systems that may be connected to the VIP. The VIP may serve as a common connection integrating different components in a system. Each of the components may be at the same or different sites. They may be connected through any one or more different types of connections including wireless connections, network connections, hardwired direct connections, and others known to those of ordinary skill in the art. Using the VIP, information may be communicated between the LIS and the instruments. The data that is transferred may include, for example, order and result information. The order information sent from the LIS may include a request for a particular operation or test to be executed by an instrument (e.g., request for staining, request for imaging protocol to be executed on a resultant slide). The result returned to the LIS may include a description of fulfillment of an order. Information in connection with one or more orders and results associated with a particular slide may be accessed in connection with the bar code identifying that particular slide. It should be noted that this unique identifier used as the encoded bar code value uniquely identifying the slide may also be used as the unique identifier associated with a slide's RFID label as described elsewhere herein.

Figure 23:
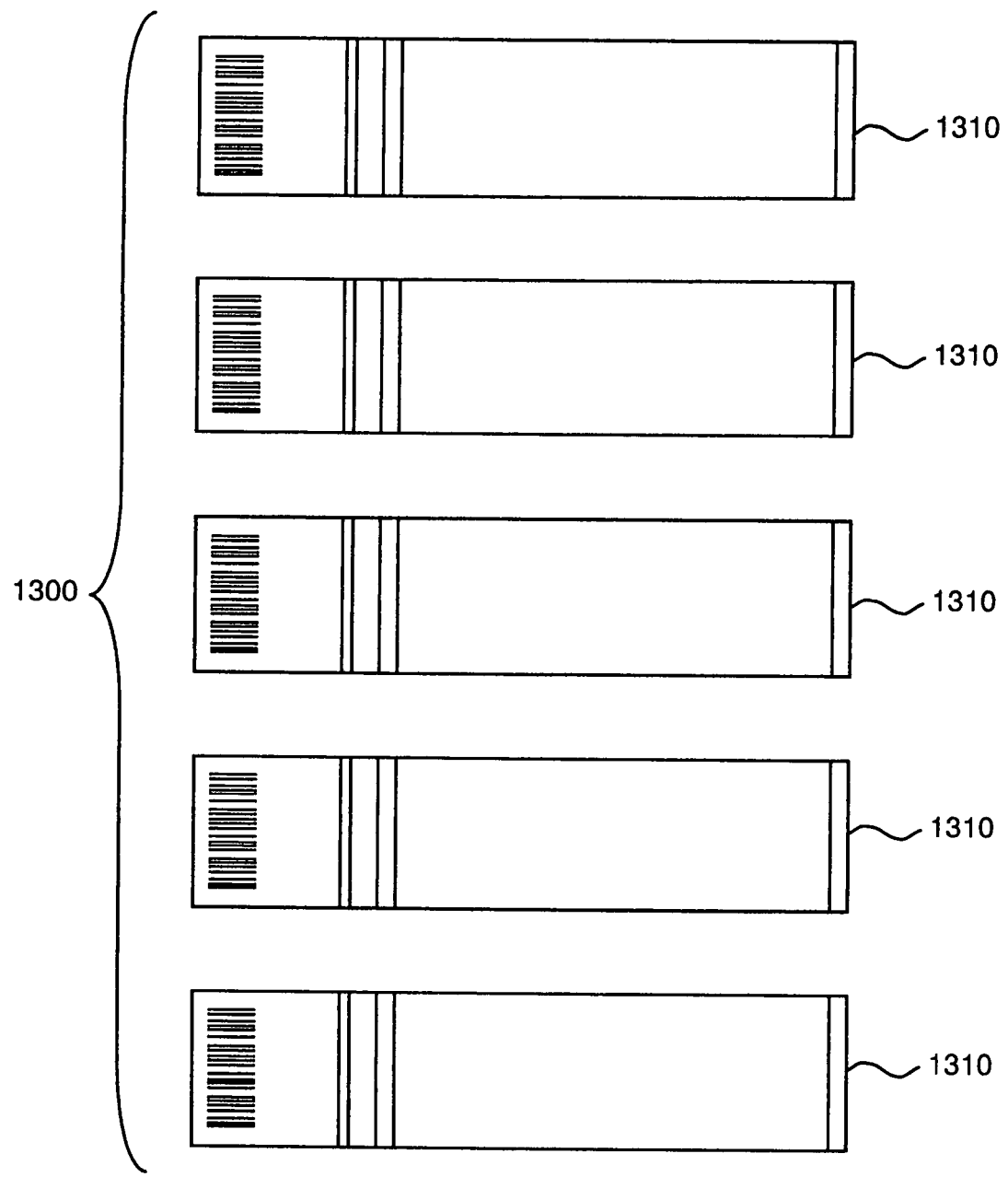
FIG. 23 is an example illustrating placement of bar codes on slides.

Referring now to FIG. 23, showing is an example 1300 illustrating the placement of bar codes on individual slides. The arrangement of the slides 1310 included in the illustration 1300 may represent an arrangement of slides, for example, included in a slide tray for processing by a laboratory instrument such as a stainer. It should be noted in connection with the illustration 1300, bar code information may be included on the surface of the slide at one end of the slide, such as, for example, the left band side of the slides as illustrated in 1300. However, techniques described herein for bar coding and other forms of encoding of information are not limited to placement of the bar code at this particular location of the slide or in a particular surface area of the slide. A label may be placed on more than one surface of a slide. The information encoded by the bar code may be an identifier serving as an index, for example, into a database for other information about the associated slide.

Figure 24:
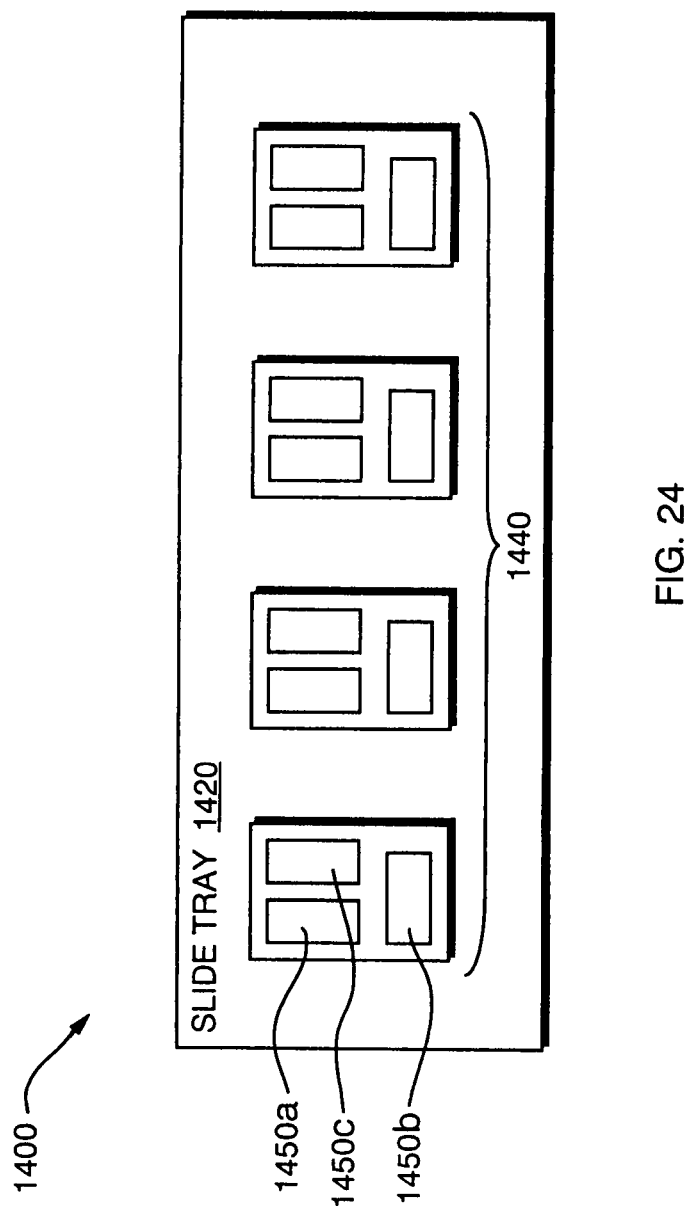
FIG. 24 is an example arrangement of slides using bar code labels.

Referring now to FIG. 24, shown is another arrangement 1400 of slides as may be included in a slide tray. Each slide in 1400 includes a plurality of bar code portions on each slide. Each of the slides 1440 may include a first portion 1450*a*, a second portion 1450*b*, and a third portion 1450*c*. Each of the portions 1450*a* and 1450*b* may include bar code information oriented, respectively, in the vertical and horizontal directions. A bar code label may be placed in each of the portions 1450*a* and 1450*b* respectively. In one embodiment, the label included in 1450*b* of a slide may be an index to information common to more than one slide, such as information in connection with a particular patient, batch, and the like. The area 1450*a* may include another index to other information that varies with each particular slide and may indicate, for example, more test specific information such as, for example, a particular reagent used, time at which a particular test or staining has been performed, and the like. Portion 1450*c* may include another label with human readable or other forms of machine readable information.

The illustration 1400 includes one particular arrangement of how each slide may include more than one bar code or other type of encoding. Other arrangements are possible than as shown in FIG. 24. It should be noted that one or more of the portions 1450*a-c* may also be an RFID label used in conjunction with a bar code label in another of the portions.

Figure 25:
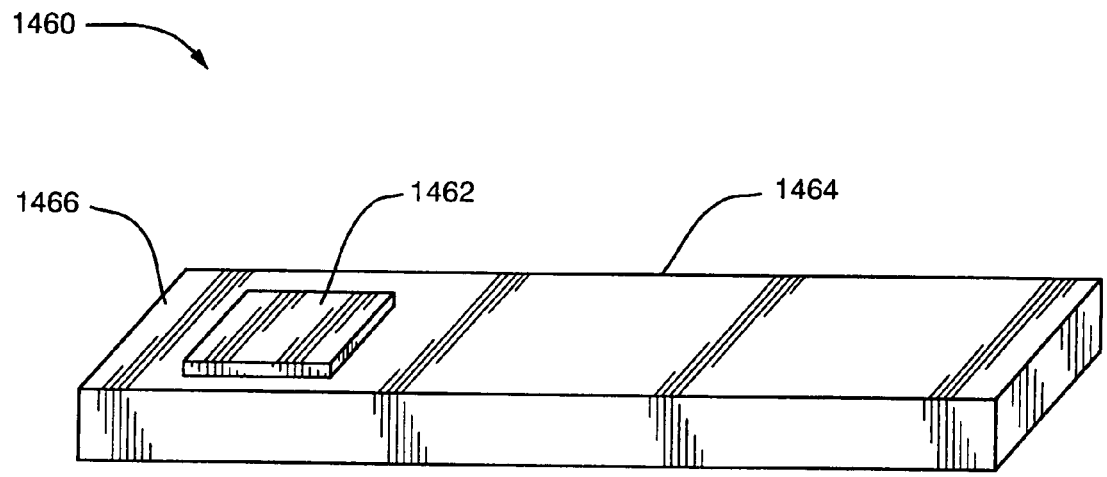
FIGS. 25 and 26 are examples of embodiments of slide arrangements with bar code labels.

Referring now to FIG. 25, shown is an arrangement 1460 of a slide with a bar code label affixed thereto. In 1460, bar code information may be included on a label affixed to a top surface 1466 of a slide 1464. A single slide such as 1464 may include one or more bar code labels 1462 affixed to a top surface thereof.

Figure 26:
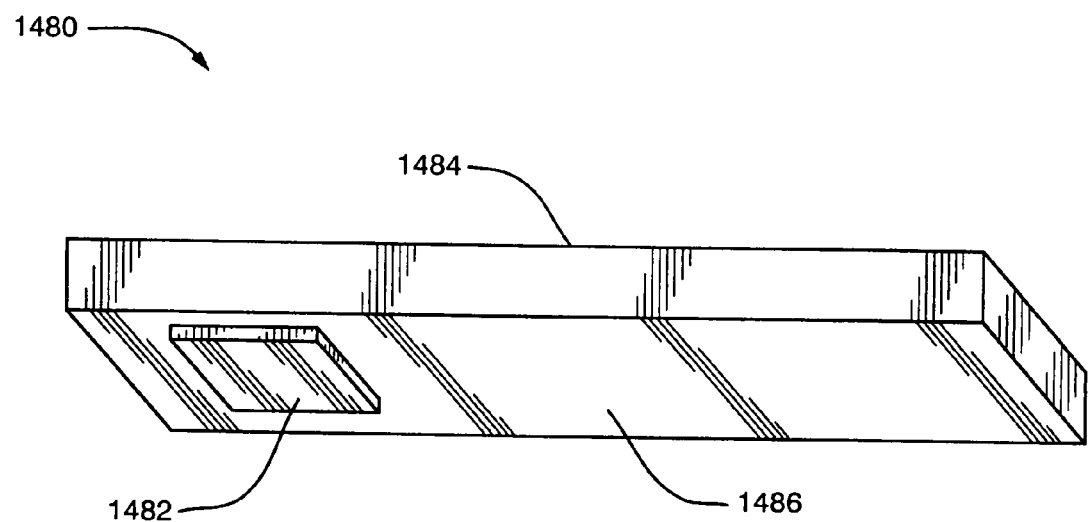

Referring now to FIG. 26, shown is another arrangement 1480 of how bar code labels may be affixed to a slide. In this arrangement 1480, a bar code label 1482 may be fixed to a bottom surface 1486 of a slide 1484. In this example, the bar code information may appear on the surface of 1482 in contact with the lower surface 1486 of the slide. If a slide 1484 is made of glass, for example, the bar code information included on the surface of 1482 in contact with the lower surface 1486 of the slide may be optically read through the glass 1484. It should be noted that a slide 1484 may include more than one bar code label affixed to the bottom portion of a slide 1484. Bar codes or other optically-recognized characters may be placed on a bottom surface of the label 1482. Through the use of mirrors, for example, the characters on the outer surface of 1482 may be reflected and interpreted by an optical reader. It should be noted that an embodiment may include one or more labels such as bar code labels including optically-recognizable characters on one or more surfaces of a slide. For example, the slide may include bar code labels affixed to the top surface and bottom surface thereof.

Figure 27:
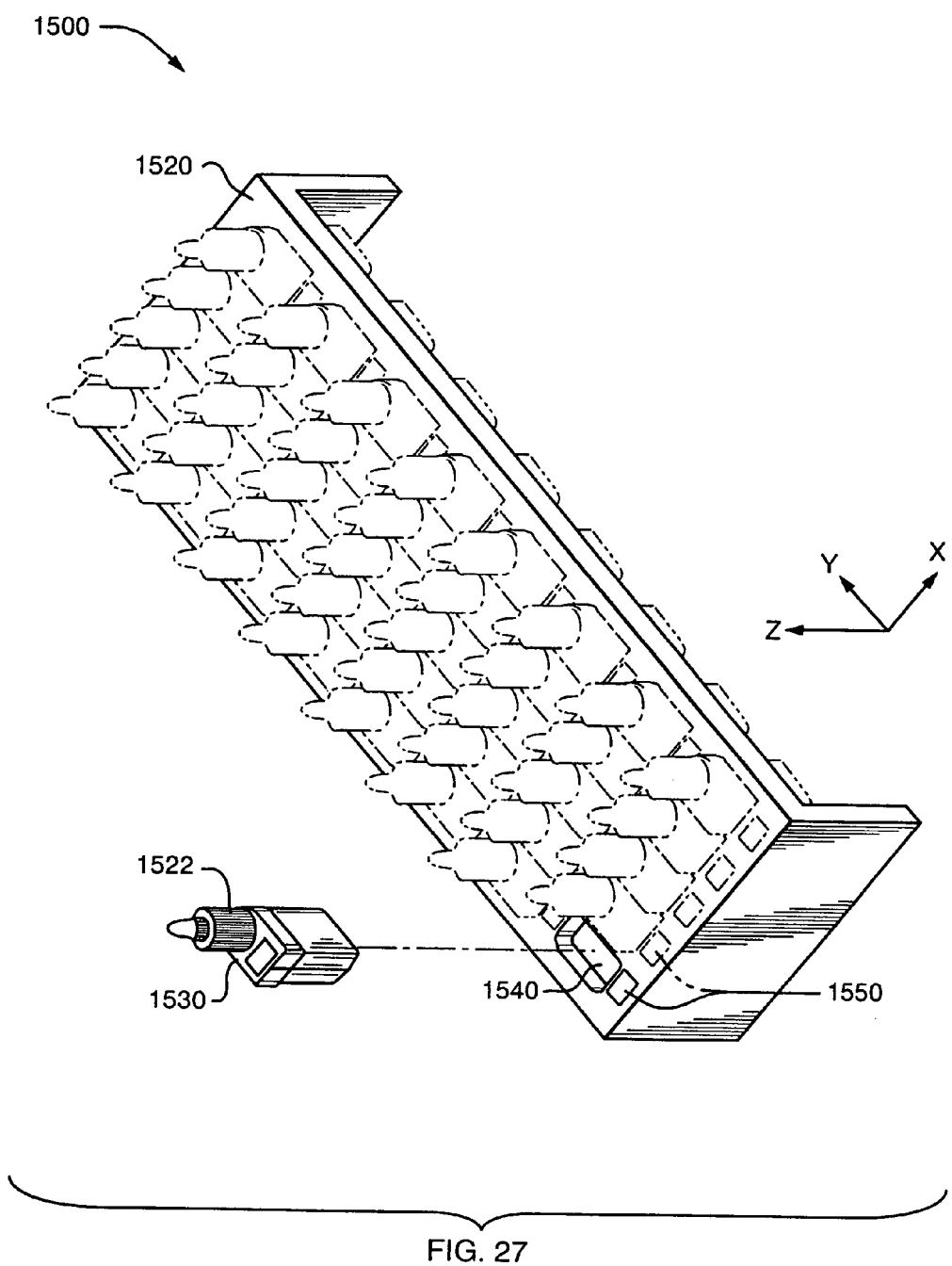
FIG. 27 is an arrangement of a reagent holder illustrating use of labeling techniques described herein.

Referring now to FIG. 27, shown is an arrangement 1500 of a reagent holder that may be used in connection with labeling techniques described herein. The illustration 1500 includes a reagent dispenser tray 1520 for holding a plurality of dispensers such as those that may include reagents. Included in the illustration 1500 is a reagent dispenser holder opening 1540 into which fits a reagent container 1522. Included on each of the reagent containers 1522 is a label 1530. The label included in 1530 may be, for example, an RFID label affixed to a surface of the container 1522. It should also be noted that the reagent containers included in the illustration 1500 may also include a bar code label on the container in addition to the RFID label 1530. It should be noted that the RFID code label 1530 may also be embedded within a container surface such as may be performed when the container is initially filled by a supplier, or other location. Included at locations 1550 may be a bar code label or other type of label which should correspond to the reagent container placed therein.

Bar codes, and the use in connection with slides and reagents is described, for example, in U.S. Pat. No. 6,352,861, Mar. 5, 2002, Copeland et al., entitled Automated Biological Reaction Apparatus, which is incorporated by reference herein.

Figure 28:
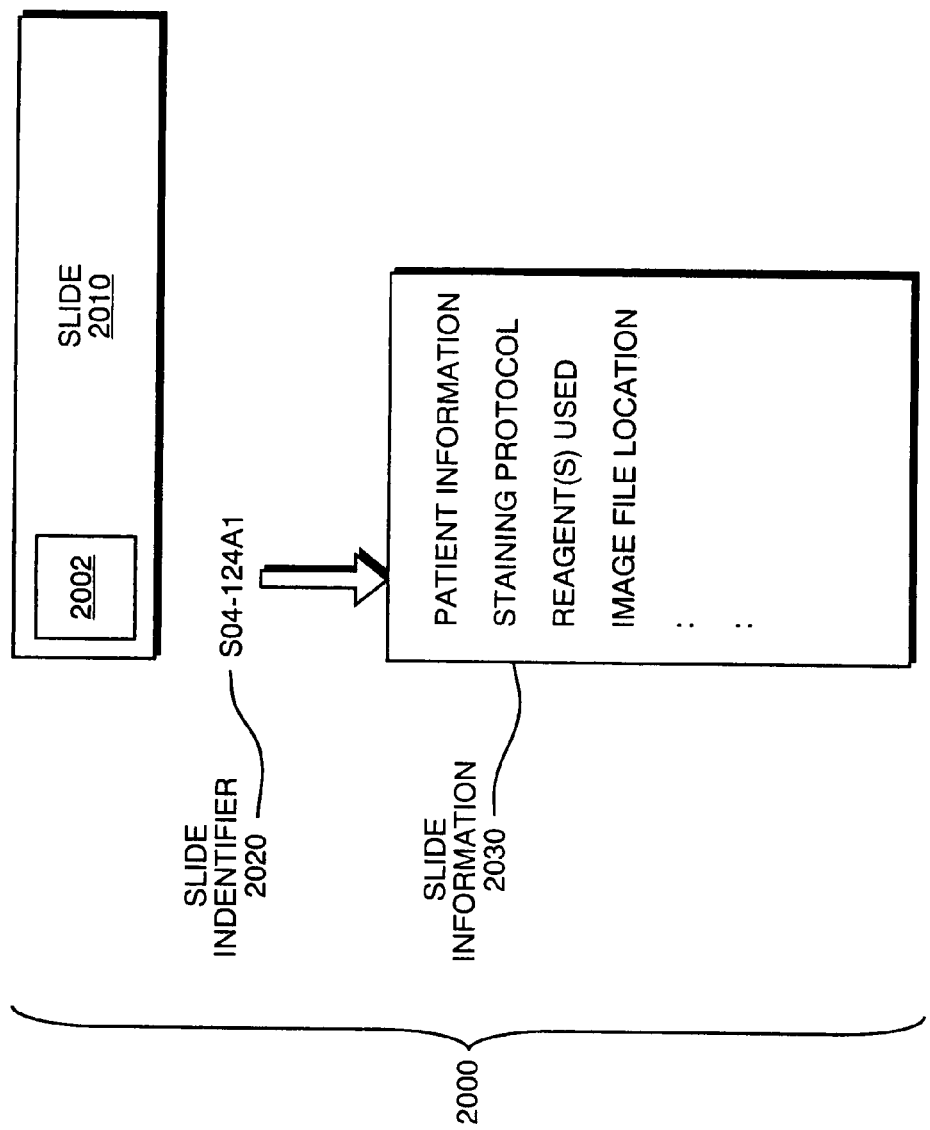
FIG. 28 is an illustration of how bar codes may be used to obtain case information.

Referring now to FIG. 28, shown is an illustration 2000 of how a bar code or an RFID label with an identifier may be used to obtain case information in an embodiment. The representation in 2000 illustrates an embodiment in which a unique slide identifier may be encoded in the bar code label or an RFID label in area 2002 of slide 2010. If 2002 includes a bar code label, the bar code in 2002 may be read by an optical reader to obtain the slide identifier 2020. In the event that element 2002 includes an RFID label, the unique identifier of the slide 2020 may be read using an RFID reader. The identifier of 2020 may be used as an index into a database to obtain information associated with a slide data element 2030. The information included in a slide data element 2030 may include, for example, patient information, staining protocol, reagents used, test results/post run information (e.g., information about which instrument performed a staining, information about when the staining was performed, a location of an image file), and the like. An embodiment may include other information in a slide data element that may vary with each embodiment, sample, and processing performed on each sample. The slide's information in the database may be updated at various points in processing as new information about a slide or other sample is acquired.

It should be noted that the information encoded in bar codes, RFID labels, and the like, may also be encrypted using any one of a variety of different encryption techniques.

Referring back to FIG. 3, the hosts may each operate autonomously with respect to the other hosts. This autonomous host operation may be characterized in connection with several aspects. A host of the IPN 100 may go offline from the IPN 100 and may later come back online as a member of IPN 100 rejoining the other hosts. When a host comes online as a member of the IPN 100, a synchronization process may be performed to synchronize data elements between the host and other components of the IPN 100. One embodiment of this process is described, for example, in FIGS. 6 and 7. By having the resynchronization functionality described herein, a host may operate offline with respect to the IPN 100 to perform other tasks, and then operate to perform tasks associated with the IPN 100. For example, a first host may perform processing associated with the IPN 100. Additionally, the first host may include other software to perform other tasks not associated with IPN 100. When performing the other tasks, the first host may be offline with respect to the IPN 100. Later, the first host may rejoin the IPN 100 and the first host may have its IPN data elements resynchronized.

While offline with respect to the IPN 100, a host may perform any one or more different operations that may vary with embodiment. For example, a host may create and edit protocols that may be later shared with other hosts. The protocols may also be only used by the host locally rather than be shared with other hosts and the VLM. The host while offline may also register new reagent packages, perform runs, create and edit user privileges, perform QC procedures, print reports and the like. The processing performed by the host while offline may result in new or updated data elements that may be subsequently used by other hosts and/or the VLM when the offline host rejoins the IPN. Alternatively, the processing performed by the host while offline, and resulting data elements, may be used only locally by the host for particular operations that may be performed by that host. The host may also perform processing offline, for example, when complex processing or processing requiring a lot of network resources is being performed. Such processing may include, for example, performing a system wide backup and/or archive of the VLM data in which it may not be desirable to also consume system resources to engage in VLM-host synchronization. The host may also perform processing offline, for example, when the host is using a data element and is relying on a constant data value or state of a data element that may be updated by another host. A host may define local data elements known only to the host. Such local data elements may subsequently be published or made global (e.g., made known to other components besides the local host) by communicating the local data elements to the VLM and other hosts. Such local data elements may also remain local with respect to a host if, for example, the local data elements are only used by that particular host. The local data element definitions and values may be known only to a particular host in contrast to other data elements which may take on a global characteristic in the IPN 100, for example, by having a host publish a data element through communication and synchronization with the VLM making the data element definition and value available to other hosts. The particular configuration of the host and its data elements may be performed on a host-by-host basis and may vary with embodiment. It should be noted that an embodiment may include hosts which perform a same set of operations and/or different operations that may vary with each embodiment.

In accordance with another aspect of host autonomy, a host of the IPN 100 may also elect to share/not share one or more data elements defined and used within the IPN 100. A host may modify its share/not share status with respect to one or more elements during operation. When a host elects to share data elements with others components of the IPN 100, the host may obtain the latest version of the data element of interest from the VLM. Also, a host may be using a data element locally and may choose to publish this data element for use by other hosts. Thus, a host may also send an updated version of a data element to the VLM which is, in turn, propagated to the other hosts. As described herein, code may be executed by each host to ensure that, for each data element of interest, each host has the most recent copy of the data element. A synchronization may be performed by each host to ensure that each host interested in a particular data element operates on the most recent version of the data element. As described elsewhere herein, a timestamp value may be used to determine a most recent copy of a data element.

In one embodiment, a host may elect to share data on a data element-by-data element basis. This allows the host to control its own use of each data element. Each host controls whether a particular data element is used at all by that host. If a data element is used, the host controls whether this data element is locally (e.g., on only this host) or globally defined (e.g., available to other hosts). The particular data elements shared among one or more hosts may reflect the functionality of the hosts and/or its associated instruments. An embodiment may have the same or different functionality associated with each of the hosts. For example, in a first embodiment, the functionality may be the same on each host. A first host and a second host may elect to share the same data elements when the first and second hosts support the same set of instruments and operations. In another embodiment, the functionality of each host may vary, for example, if the first and second hosts support different instruments and/or perform different operations. In this instance, the first host may use a first set of data elements, such as staining protocols, and the second host may use a second different set of data elements. A host may also elect to share some data elements and not others. For example, all hosts may elect to share common data elements such as case and patient information but elect to share different data elements, for example, regarding protocols used by instruments associated with each host.

When each of the first and second hosts perform synchronization processing, the synchronization processing may be performed only for those data elements of interest to each host. In the foregoing example where the first and second hosts use different staining protocols but the same case and patient information, both the first and second hosts may perform data synchronization with respect to case and patient information, but not with respect to all staining protocols.

Figure 29:
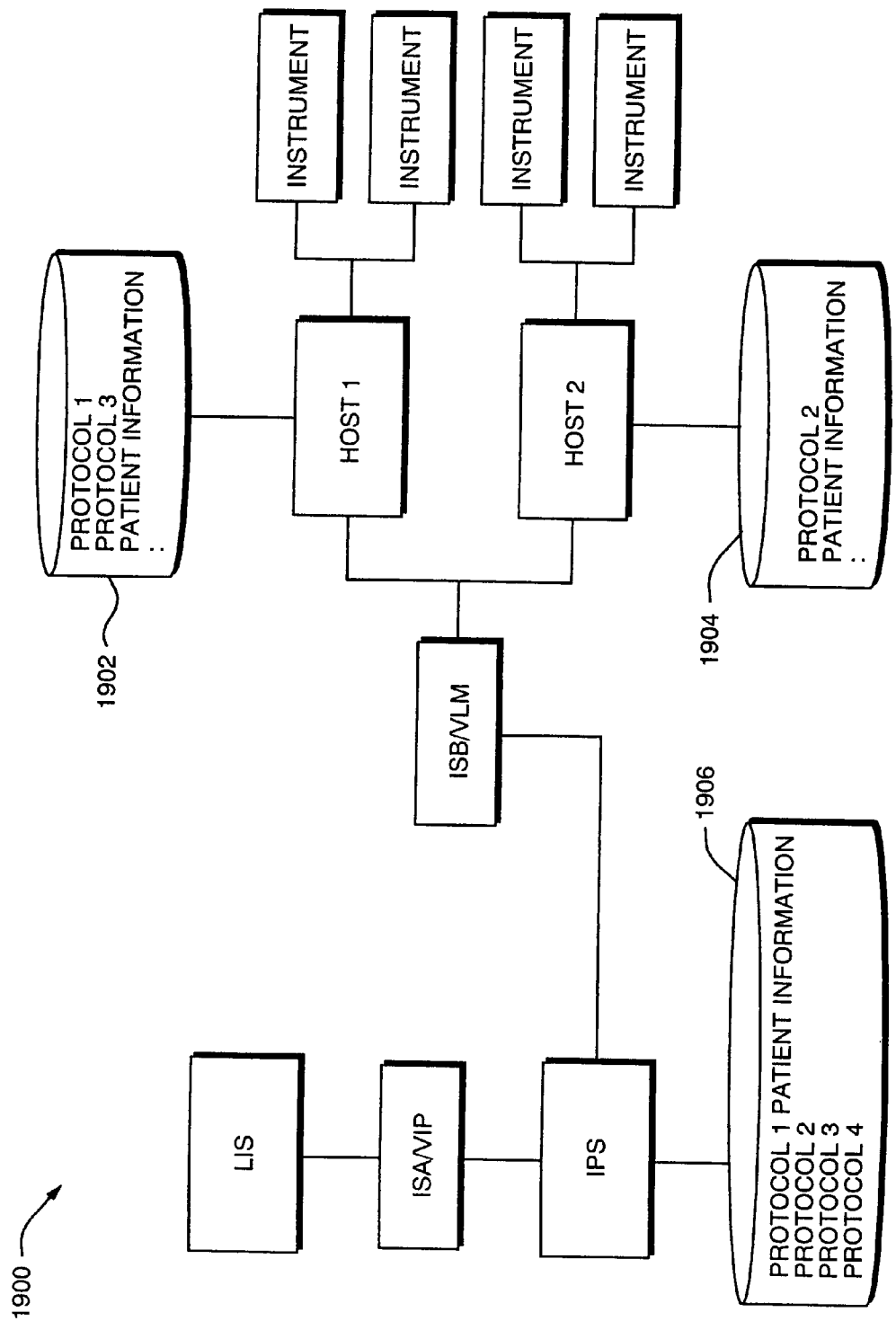
FIG. 29 is an example of an embodiment of a system illustrating the use of selective data synchronization and data sharing by hosts.

Referring now to FIG. 29, shown is an example of an embodiment of a system that may be used in connection with performing techniques described herein. The example 1900 includes components similar to those as described and illustrated, for example, in FIG. 3. Also included in 1900 are elements 1902, 1904, and 1906 illustrating the data containers or stores that may be included in an embodiment. It should be noted that these additional components are included in the example 1900 to illustrate selective data synchronization. Included in 1902 are staining protocols 1 and 3. In this example, only staining protocols 1 and 3 are of interest to host 1. Host 1 is executing a version of software supporting its lab instruments which only perform these two protocols. Host 2 includes a different version of software supporting its lab instruments which perform only staining protocol 2. The master database 1906 includes information on all staining protocols. Although the host databases may include only particular staining protocols, both host databases include the same patient information.

When performing the resynchronization processing, for example, as in FIGS. 6 and 7, the processing may be performed only with respect to those data elements of interest to a host which may vary with each host. In one embodiment, the particular data elements of interest that may vary with each host are defined in accordance with a subscription list of data elements of interest on each host. This list may be stored on each host and/or in the master database, for example, element 906.

In connection with monitoring reagent use, a concept of reagent ownership may be included in an embodiment as described elsewhere herein. A reagent may be characterized as a resource that may be shared by more than one instrument connected to more than one host. In processing of slides or other samples, the reagent use and supply may be monitored. In one embodiment, a data element may be defined and associated with each set of one or more reagents that may be used together. When using reagents, it is desirable not to start a run to process a batch of slides or other samples if there will not be a sufficient amount of the one or more reagents to complete the run. In order to make this determination, an embodiment may track the amount of the reagents. A host having ownership of the data element associated with one or more reagents may update the recorded amounts of each of the reagents as may be included in an attribute or other field of the reagent data element. In other words, in order to write or update a data element of a reagent, the host has ownership of this data element. One method for acquiring ownership that may be performed in an embodiment is described, for example, in FIG. 8.

Ownership of a reagent may also be used to represent and control which instrument and host has a set of one or more reagents. For example, it may be desirable to physically move a set of one or more reagents from one lab instrument associated with a first host to another lab instrument associated with a second host. Where the set of reagents may physically reside may be represented by which host owns the data element associated with the set. Generally, a host which owns a reagent data element will be using the associated reagent and thus need to update the quantity as recorded in the associated data element.

As an example, a new set of reagents may be used on a first instrument associated with a first host. Processing may be performed to register the data element for the new set of reagents on the first host. Using the techniques described elsewhere herein, the data element definitions as known to the first host may be automatically replicated in the database of the IPN 100 and also locally on each host through data synchronization processing. The first host may be the recorded owner of the reagent data element. A problem with a first instrument may occur and the new set of reagents may be moved from the first instrument to a second working instrument connected to another host. In this example, the reagents may physically be moved to the second host and the second host may request and obtain ownership of the new set of reagents. While in use by the first instrument, the first host accordingly updates any associated amounts of the associated data element for the new set of reagents. While in use by the second instrument, the second host similarly updates any amounts for the new set of reagents in the associated data element. In another example, the first instrument may be processing a set of slides using the new set of reagents. While the first instrument is working, a request for ownership of the new reagents is made by a second host so that the new set of reagents can be moved for use in a second instrument associated with the second host. The ownership request by the second host will be denied while the first instrument is still using the new set of reagents. While the first instrument is using the reagent, the first host updates amounts of the new set of reagents in the associated data element. When the second host acquired ownership of the reagents, the second host updates the amounts to reflect consumption by the second instrument.

The movement of reagents to different physical locations may be performed manually and/or in an automated fashion.

The foregoing illustrates how reagent ownership may be used to monitor the supply and location of the reagent and also facilitates sharing of reagents among different hosts and instruments. The ownership of a reagent data element may be characterized as a software locking technique for control of the associated reagent. It should be noted that in the foregoing, ownership cannot transfer unless the owner host is online and elects data sharing. For example, a host may be offline and use a set of one or more reagents which it owns. Another host cannot successfully obtain ownership, for example, by executing the steps of FIG. 8 while the host is offline or while the host refuses to transfer ownership (e.g., because the reagent is in use by one of the host's instruments).

In one embodiment, before a run of slides is started, a determination can be made as to how much reagent or other supplies are required for the run to complete. In the event that there are insufficient supplies, the run may not be allowed to commence. The foregoing determination regarding the sufficiency of a reagent may be performed by code executing on the IPS 100, such as by the VLM component residing on the IPS in an example embodiment.

In the event that reagent reaches a predetermined threshold level or is otherwise empty, an order may be automatically generated for reordering the reagent. Additionally, as described elsewhere herein, orders may be placed on a regular basis in accordance with previous use history of reagents and other supplies. This is described elsewhere herein in more detail.

In connection with the system described herein, for example, in FIG. 3 and FIG. 29, functionality may be included for user or customer configurable options. In one embodiment, one or more of the hosts may include code to display menu screens to obtain one or more user configurable options. Configuration options may be communicated using the messages described elsewhere herein as may be sent from the host to other hosts and for storage in the master database, for example, as element 1906 of FIG. 29.

Figure 30:
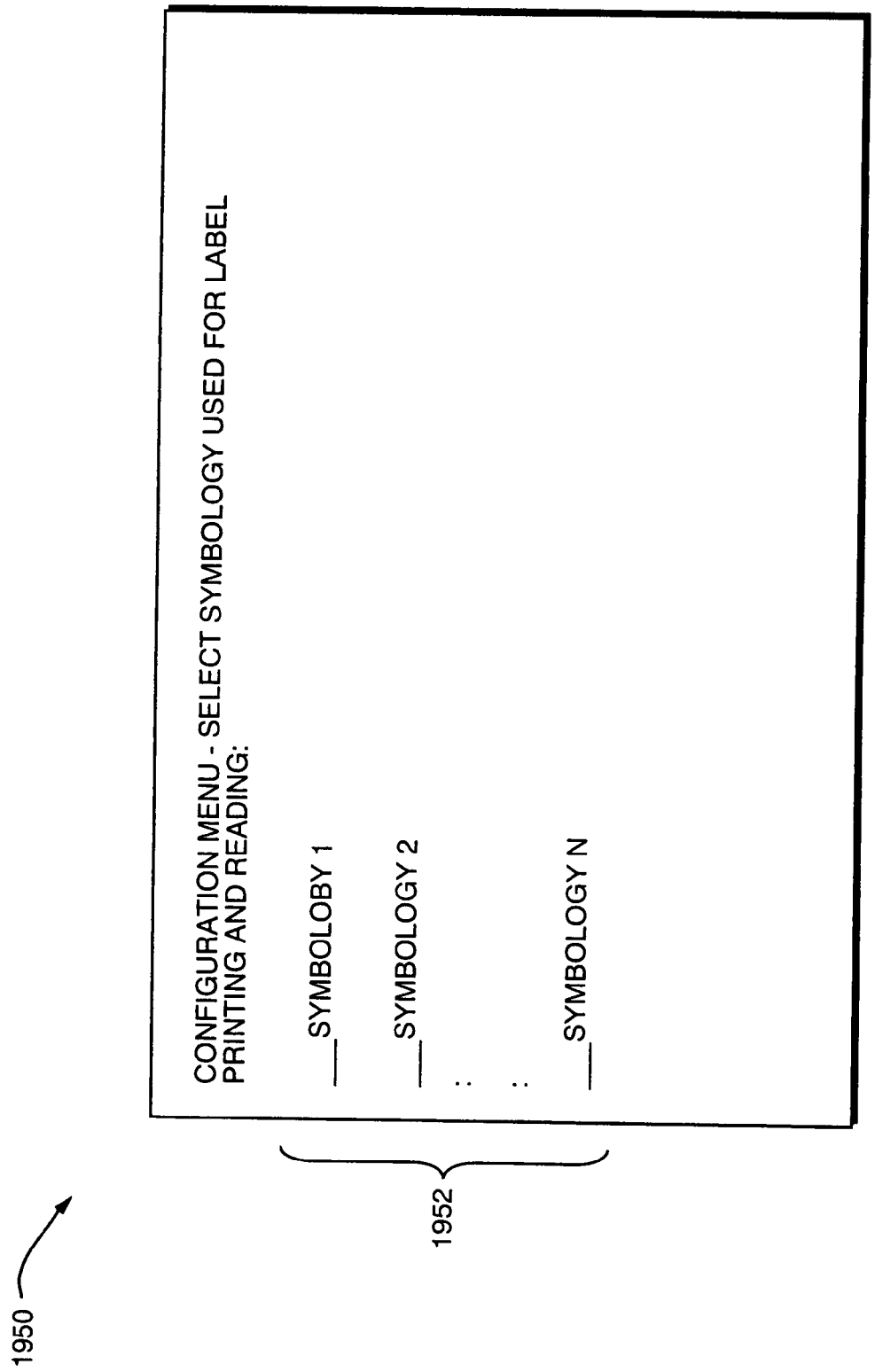
FIG. 30 is an example representation of a configuration screen shot that may be displayed in connection with selection of configuration options.

Referring now to FIG. 30, shown is an example representation of a configuration screen shot that may be displayed on a host in connection with selection of configuration options. In the example 1950, one or more symbologies may be displayed as included in 1952. Element 1952 may include all available symbologies from which a user may perform a selection. The symbology selection made may be used in connection with reading and/or printing any bar code labels that may be included on slides, or other samples. In other words, the configuration option causes each bar code reader on each instrument of every host, and each label printing device in a system such as 1900 to operate in accordance with the symbology configuration selection. It should be noted that the configuration options may also be subsequently modified and the update may be replicated to the one or more hosts and other databases in a system using the messaging techniques as described elsewhere herein. Configuration options may also be specified using other techniques in addition to, or as an alternative to, those described herein. It should be noted that an embodiment may also include functionality for configuration option selection on other components of a system besides the host. For example, the IPS may also execute code to perform configuration option selection.

An embodiment may also include functionality that limits the ability to perform configuration updates. For example, configuration options may only be configurable from a particular host, or in accordance with an authorization level of a particular user id, and the like.

It should be noted that in connection with configuration data and other data that may be replicated in a system, a timestamp or other time indicator may be associated with a set of data. When performing synchronization, the most recent copy of a data set in accordance with the most recent timestamp may be used.

In one embodiment, label printing may be performed by one or more hosts at the time slides are formed. A label printer may be an instrument connected to a host, for example, as illustrated in FIG. 3 and FIG. 29. It may be desirable to place the label onto each slide as early as possible with the slide identifier. The label may include, for example, a bar code identifier and other human readable and/or machine readable information.

The unique identifier associated with a slide may be formed using any one of a variety of techniques. In a system in which the identifier is associated with the slide being archived for a long time period, such as for several years, the identifier should be unique for this duration. In one embodiment, the following is an example format that may be used in connection with forming identifiers. A gross tissue sample may be obtained and associated with an identifier with the following root format:

LYY-nnn . . . nnn where

L may be a letter representing a source of the tissue (e.g., S for surgery, B for bone marrow);

YY may be the last two digits in the year in which the sample arrived (e.g., 04 for the calendar year 2004); and Nnn . . . nnn may represent a series of integers in which the next integer in a current sequence is associated with the current tissue.

Subsequently, this tissue sample may be divided into case blocks. For each case block, one or more slides may be cut from the tissue sample. Each case block may be assigned an identifier. For example, in one embodiment, each case block may be associated with a next single character as occurring in the alphabet so that the first case block is associated with A, the second with B and so on. Each slide within a case block may be associated further with a next integer in a sequence beginning with 1. The case block identifier (e.g., A, B, . . . ) and the slide sequence number (e.g., 1, 2, 3, . . . ) may be placed as a suffix on the above gross tissue sample identifier so form the slide identifier. For example, the following may be a slide identifier: S04-1234A1. This slide identifier may be encoded, for example, using one of a selected bar code symbologies on a label. The slide identifier may also be used in forming the RFID label identifier as well. One or more slides associated with the same case may be identified by the root portion concatenated with the case block identifier (e.g, case identifier S04-1234A, slides in the case may be S04-1234A1 and S04-1234A2). An embodiment may use other techniques in connection with forming the identifiers for slides, cases, and the like.

In connection with forming a unique identifier for each slide or a batch of slides, an inherent property of the slide, container, and/or tissue sample may be used to generate a unique identifier.

As described elsewhere herein, an embodiment may store the unique slide identifier in fields ORC-2, 3, and/or 4 of messages used in communications described elsewhere herein. The unique slide identifier may be used with the bar code and/or RFD identifiers as described elsewhere herein. In one embodiment, each of the ORC-2 and ORC-3 fields may uniquely identify the slide. Slide information may be included, for example, in the OBX segment. In addition to the slide identifier, the slide information may also include, for example, the JPEG or other image file location that may result from imaging, staining protocols, reagents to be used, and the like.

It will be appreciated by those of ordinary skill in the art that the particular steps performed in connection with forming an identifier used in connection with bar codes, RFID labels and the like, may vary in accordance with an embodiment and also the particular tissue sample and slides to be formed.

The complexity in configuring and scheduling runs of samples may increase as the number of reagents, instruments, and overall size of a laboratory increases. Different factors may be considered when scheduling runs of samples for processing by laboratory instruments. For example, the configuration may need to take into account certain quality control (QC) requirements. Some QC requirements may be specified in rules and regulations such as a number of positive and/or negative controls as may be required in accordance with the College of American Pathologists (CAP), Clinical Laboratory Improvement Amendments (CLIA), and the like. Some QC aspects may also be those desired or preferred by pathologists or as may be otherwise expected in an industry. Another factor is the supply of reagents and other supplies in scheduling a run. An embodiment may determine the amount of reagents and other supplies to be consumed by a run and then allow or not allow a run to occur in accordance with this determination. An embodiment may also consider configuring one or more runs which process slides in different groupings in an effort to maximize throughput. A different instrumentation and reagent configuration may be considered, for example, to maximize throughput and laboratory performance. As another consideration in scheduling, if a new reagent or other element used in processing is being used, different controls (e.g., positive and negative controls) may need to be scheduled in order to certify that particular element in accordance with different certification requirements.

An embodiment may use software executed on one or more of the hosts included in the system illustrated, for example, in FIG. 29 and FIG. 3, in scheduling batches or runs of samples, such as slides, for processing.

Figure 31:
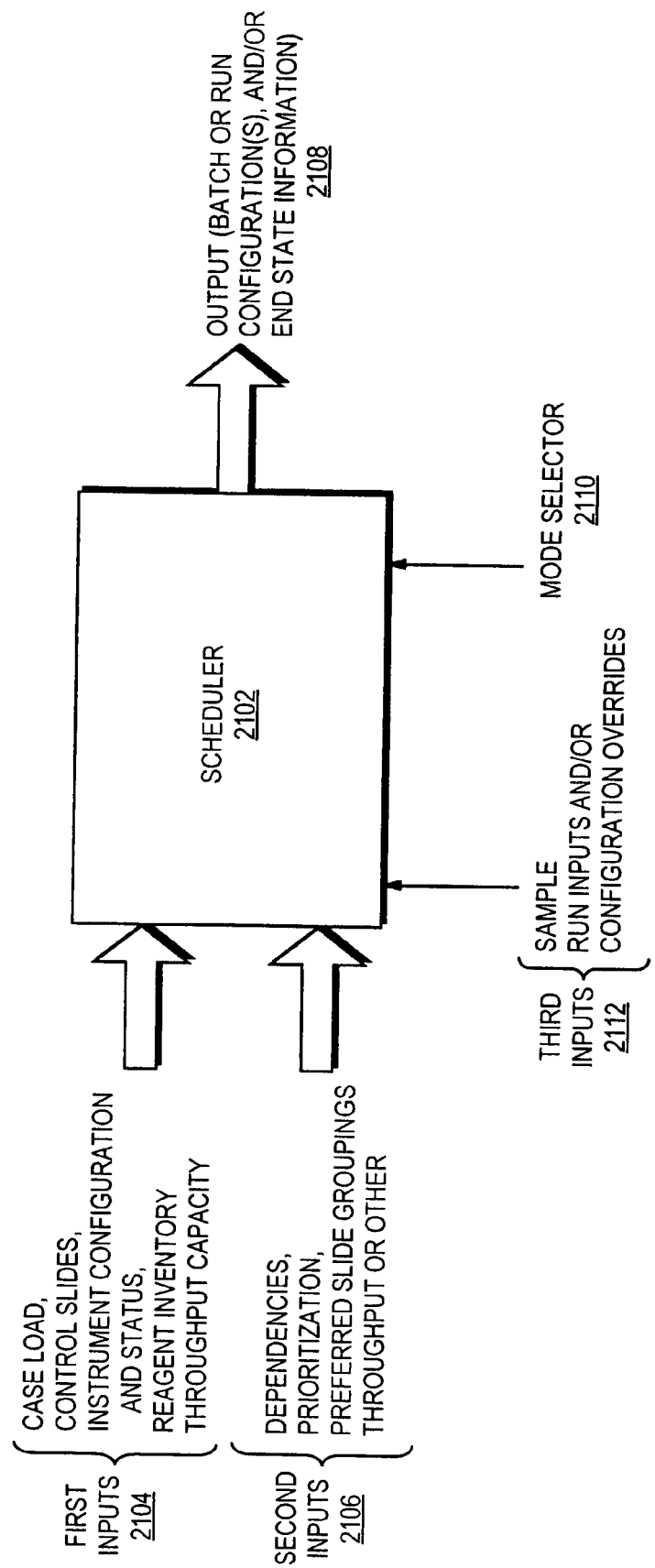
FIG. 31 is an example illustrating an embodiment of a batch scheduler.

Referring now to FIG. 31, shown is an example 2100 illustrating a batch scheduler. In 2100, the batch scheduler 2102 may have one or more first inputs 2104. Additionally, an embodiment may also include one or more second inputs 2106. Generally, the first inputs 2104 may include information about the current state of the laboratory to enable the batch scheduler 2102 to evaluate and/or generate one or more particular runs. An embodiment may also use other information than as described herein. The first inputs 2104 may include information input from the database, such as may be stored in the IPS. The information may include, for example, the current case load or case samples to be processed, control slides to be processed in accordance with system requirements and the number of case slides, instrument configuration and status information, reagent inventory, and throughput capacity. The instrument configuration and status information may include which machines are up and running or otherwise unavailable for processing a run, which reagents are on which instruments, and the like. The reagent inventory information may include information about the types and current quantities of each reagent. Throughput capacity information may include the rate at which different instruments perform certain processing steps in connection with the slides. The second inputs 2106 may include one or more optional inputs used in connection with the scheduling and evaluation thereof. Second inputs may include, for example, dependencies, prioritizations, preferred slide groupings, and other scheduling criteria such as throughput. Dependencies may specify an ordering dependency of certain slides or other samples. For example, a slide may require a first staining prior to performing other processing by another instrument. Prioritizations may be specified and may include, for example, designating which one or more slides should be given priority than others. Preferred slide groupings may include, for example, an indication of how slides should be grouped in the runs. For example, it may be preferable to group slides by antibody for processing rather than by case. One or more performance criteria may be specified such as, for example, throughput. The scheduler may use this in determining which run configuration may be preferred. For example, it may be desirable to maximize throughput. Accordingly, a different scheduling algorithm or different rules may operate in determining one or more runs for processing the current case load. Additionally, third inputs 2112 may be input to the scheduler 2102. The third inputs 2112 may include sample run input and/or configuration override information. The override information may be input alone or in combination with other elements of 2112. The override information may include different configuration options, such as if a particular instrument was online rather than offline, if a particular reagent was on a different instrument with a different capacity, and the like. Generally, the override information may be used to generate run configurations and/or evaluate a run configuration in accordance with a variation to the laboratory configuration. When the scheduler 2102 operates in accordance with a first mode, as may be selected with the mode selector 2110, the scheduler 2102 may output one or more runs of slide configurations in accordance with the specified input(s).

The scheduler 2102 may also run in a second mode where a particular set of sample run configurations included in third inputs 2112 may be scheduled. The run configurations in this second mode may be given as an input to the scheduler. In other words, rather than operate in a first mode which produces run configurations, the scheduler 2102 may operate in a second mode to simulate the state of the laboratory at the end of a proposed set of sample runs included in 2112. In this second mode, the scheduler may produce as an output the end state of the system for a given set of one or more input runs. Generally, the end state information may include one or more pieces of information describing the end state of the system if the input runs are performed given a current state of the laboratory. The end state information may be used to evaluate which one of a particular set of input runs may be preferred. The end state may include, for example, the end time of processing the samples, the reagent inventory, whether there was an insufficient reagent supply, and the like. In one embodiment, if the scheduler runs in the second mode, the sample run configurations of 2112 may be required. The configuration overrides may be optionally specified when the scheduler operates in accordance with the first or second mode.

An embodiment may also not include a mode selector and may only operate in accordance with the first mode or the second mode described herein. Other variations of the scheduler are possible as will be appreciated by those of ordinary skill in the art.

The foregoing may be used to dynamically configure and/or evaluate a given set of runs prior to actually executing the one or more runs. As the complexity of a laboratory increases, the usefulness of such a scheduler may also increase since manually scheduling and determining runs using empirical knowledge becomes more difficult.

In one embodiment having multiple hosts, software and/or hardware may be included on each host to communicate necessary information for scheduling operations to a master scheduler module. The master scheduler module may also include hardware and/or software to perform scheduling across multiple hosts and associated instruments. The master scheduler functionality may be performed by a designated host, the IPS, or other component in communication with other hosts to obtain lab-wide instrument information, case load, reagent information, and the like. Scheduling uses information about all laboratory instruments to be scheduled and their associated capabilities. One component, characterized above as the master scheduler, may obtain all necessary scheduling inputs and may be in communication with the hosts similar to the way the VLM is in communication with the hosts. Each of the hosts may include software for supplying such necessary information. An embodiment may also include a component on each host to perform some scheduling processing for instruments connected to that particular host. Such scheduling components included on each host may also be in communication with a master process coordinating scheduling tasks among the different hosts. In this latter configuration, the scheduling division of labor may be partitioned among the hosts and a master scheduler. Alternatively, an embodiment may have a single master scheduler gather scheduling information (e.g., instrument and reagent information, other laboratory configuration information, and the like), as may be reported by each host. The master scheduler may then use this information to perform all scheduling tasks. In yet another embodiment, each host perform its own scheduling of instruments controlled by each host.

An embodiment may also include a scheduling option to produce a number of scenarios to best process the case load in accordance with specified criteria such as, for example, instrument utilization optimization, throughput maximization of an instrument and/or laboratory, consumption of a particular reagent by a certain date, and the like. The scenarios produced in accordance with the criteria, case load and other information as may be included in an embodiment may result in a work list designating a processing order to be executed in a manual and/or automated fashion. An embodiment may also include a feature for scheduling to handle new incoming orders, and/or existing orders, designated as priority orders requiring processing priority over other orders. The scheduler may include a feature to process such priority orders, for example, by specifying priority orders as another input to the scheduler. The scheduler may produce a processing order in accordance with the designated priority orders and in accordance with other criteria. The scheduler may include functionality, or communicate with other components in the laboratory, to provide reagent locating support, such as may be implemented using the RFID or other technology, to assist technicians in manually assembling a staining run. The scheduler may including functionality, or may communicate with other components in the laboratory, to also analyze historical trends of reagent use and manage reagent inventories to aid in scheduling preventative maintenance on instruments, placing restocking orders, and the like. The scheduler may also assist in determining runs in accordance with regulatory compliance such as, for example, by scheduling control tissue samples/slides in staining runs. Such regulatory compliance information and requirements may be communicated as an input to the scheduler and the scheduler may produce scheduled output runs in accordance with this, and other criteria as may be specified.

It should be noted that the functionality associated with the scheduling operations may be performed by any one or more components in a system. Some example configurations, such as those which are a partnership of host computers and/or other components, are described herein but should not be construed as a limitation of the techniques described herein.

In processing slides or other samples, slides of a particular case may be broken up so that each of the slides are processed by different instruments. For example, in order to maximize throughput, slides may be processed in accordance with a particular antibody. Slides associated with a first antibody from a first set of cases may be processed in a first run. Other slides associated with a second antibody from the first set of cases may be processed in a second run. After all slides of the first set of cases have been processed, an embodiment may include a post run slide sorting step to re-collate slides of each case back into their respective case folders. In other words, for efficiency in processing, cases of slides may be separated. After processing (e.g., staining) of the slides is complete, the slides may be regrouped by case. In an embodiment, this collating step may be performed in a manual and/or automated fashion. For example, the slide information as may be included in a bar code label, RFID label, or other form on each slide may be used in this collating step. The bar code label of each slide, for example, may include the encoded case information used to group together slides of the same case. The slides of each case may then be placed into a single case folder.

Figure 32:
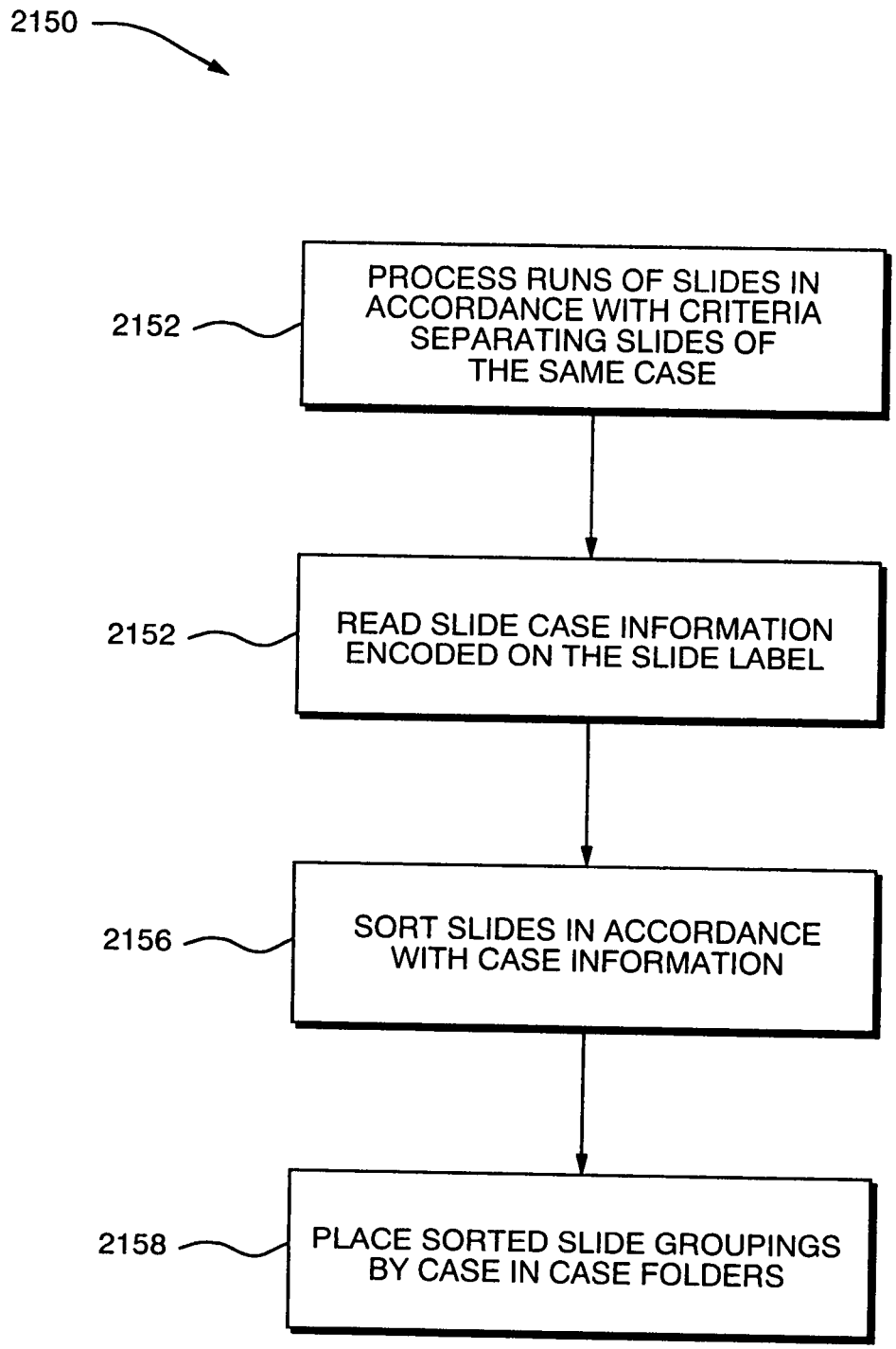
FIG. 32 is a flowchart of processing steps that may be performed in an embodiment in connection with collating slides.

Referring now to FIG. 32, shown is a flowchart 2150 of processing steps that may be performed in an embodiment in connection with processing slides or other samples for collating. The steps 2150 generalize those just described in using encoded slide or sample information to sort the slides. At step 2152, the slides are processed in runs determined accordance with one or more criteria. As described above, slides may separated in accordance with antibody in order to have more efficient processing maximizing throughput. The runs processed at step 2152 may be determined manually or in connection with using the scheduler described herein. At step 2154, case information about each slide is read from the encoded information, such as for example may be encoded in a slide's bar code label. The case information may be read using a machine, such as an optical reader, an RFID reader, or manually, by a person reading a printed label. Slides having the same case information may be grouped together at step 2156. At step 2158, slides of the same case are placed in the appropriate case folders. Processing of steps 2156 and 2158 may also be performed manually and/or using automated techniques. It should be noted that slides of a same case may be, for example, all slides produced from a gross tissue sample as may be identified using the case identifier described elsewhere herein. In one embodiment, as slides are processed, they may be placed into one or more collection locations. The slides from these collection locations may be sorted automatically in accordance with case identifier using a reader for the particular type of label. Those slides having a common case identifier may be placed in a same output grouping which are subsequently placed in a case folder.

In another embodiment, location information about where a slide is being processed in a lab may be tracked as the slide's location varies. The information may be entered manually and/or automatically. The information may be collected automatically, for example, by having the laboratory instruments report information about slides as they are processed or loaded into the instruments using a bar code or other reader. The information may be manually entered, for example, with a user interface on a host. The information may then be replicated in other locations, such as the database of the IPS and other hosts. At some later point in time, processing may be performed, for example, by a host or remote operator of the LIS system, to query the VLM database (as may reside, for example, on or connected to the IPS), to determine the location of all slides included in a same case. The information may be used to locate and combine slides of a same case.

Figure 33:
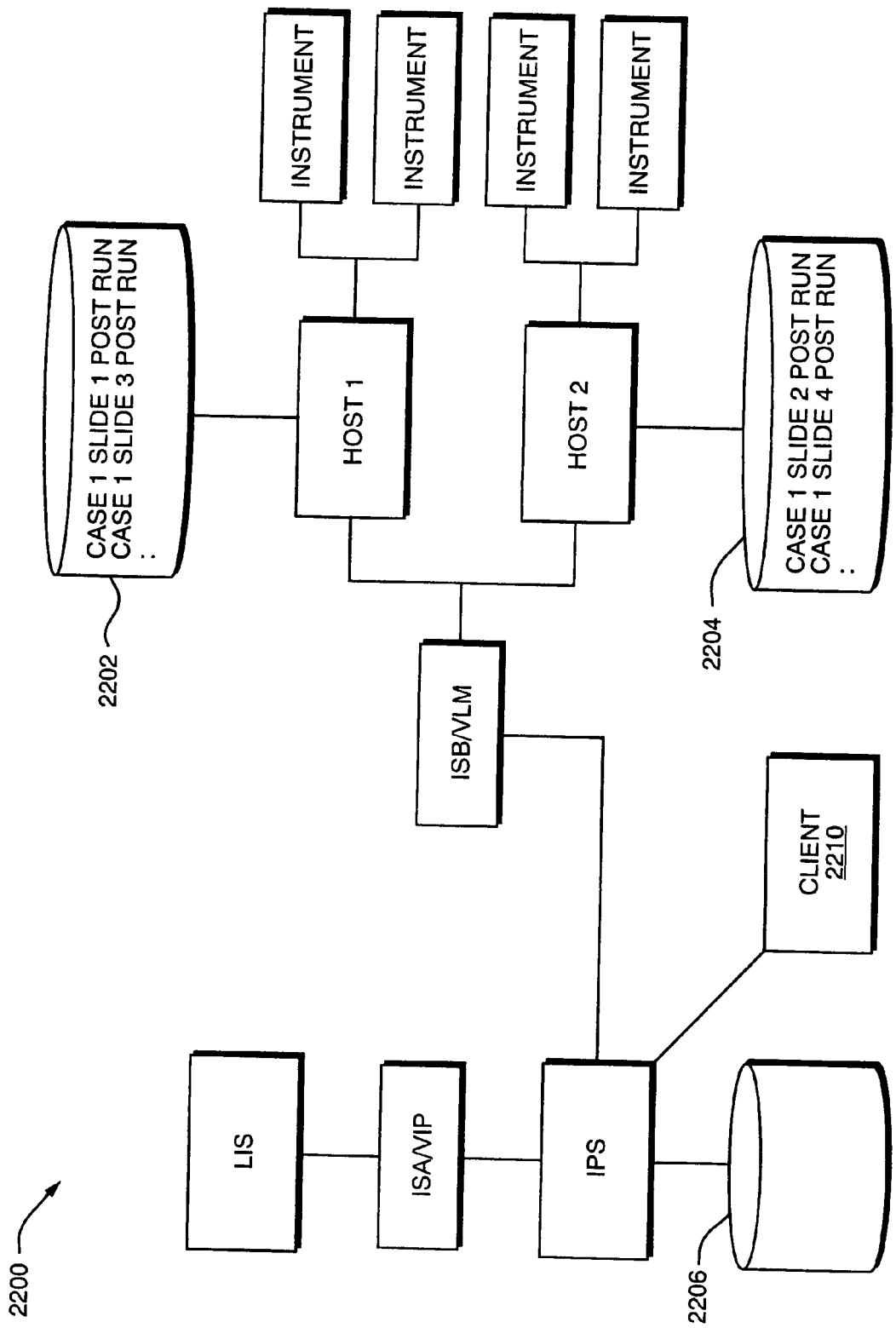
FIG. 33 is an example of an embodiment of a system illustrating remote access and cross host case reporting.

Referring now to FIG. 33, shown is another example of an embodiment of a system illustrating remote access and cross host case reporting from a client. In the example 2200, included are components similar to those described in connection with other figures. Also included in 2200 are an IPS data store 2206, host 1 data store 2202, host 2 data storage 2204, and a client 2210. The client 2210 may be client software that may execute on a system connected to the IPS. The client 2210 may be remotely or otherwise connected to the IPS using any one of a variety of connections described herein and as known to those of ordinary skill in the art. The client 2210 requests of the IPS, acting as a server, certain information. The software and/or hardware providing this service may be, for example, included as functionality in the VLM, an additional component, or functionality embodied in multiple hardware and/or software components. For example, the IPS may include a Webserver which serves web pages including requested information. The Webserver may communicate with the VLM to obtain the necessary web page and information requested by the client. The VLM may control access to, and produce information used in connection with, web pages served by the Webserver. Alternatively, the VLM may control access to a web page and may obtain data values from a data base. However, the VLM may communicate with another component to query the hosts and/or perform any further processing on raw data values obtained from the database in order to produce the necessary data to populate a served web page. The VLM or other component may issue a request, such as a UDP request, to all hosts to report back any information (e.g., case, service, etc.) in accordance with a client request.

The hardware and/or software components used in the foregoing client reporting processing as illustrated in FIG. 33 may be on one or more different computer system configurations that may vary with each embodiment. For example, the Webserver may be on the same or different computer system than the VLM. In an embodiment, the Webserver, VLM and any additional components may also be located on the same computer system. In one embodiment, the request made by the client 2210 may be made in accordance with a query entered using an interface, such as a graphical user interface, through the client. For example, a request may be made to view all data associated with a particular case. This data may include case information associated with the order as may be communicated from the LIS to the IPS, post run information such as staining protocols, reagents, and the like, used in connection with processing the order. The example 2200 represents a snapshot of the system at a point in time after the order for case has completed processing to satisfy the order. In one embodiment, an order that has not yet been completely processed is stored in the data store 2206.

At any point in time, 2206 includes information representing the current caseload of orders in progress that have not yet completed. As the order is processed, post run information about the different processing steps can be returned from host to the IPS. This post run information may also be stored locally in each host and in 2206 while an order is in progress. When order processing is complete, information may be removed from 2206 with the postrun information remaining in each host's respective data store. It should be noted that as described herein, the postrun information may be a superset of some or all of the original order information, case information, and the like. The information maintained at each host after order processing has completed also includes case information in order to identify and collate all information associated with each case. With reference to FIG. 33, a client may request all information about Case 1. Since the order for Case 1 in this example has completed processing, no information is found in 2206 by the IPS. The IPS then communicates with each of the host, such as host 1 and host 2, to obtain all information on Case 1 as maintained on each host. The IPS may then gather this information received from the one or more hosts on Case 1 and return it to the client, for example, in the form of a web page that may be displayed by Internet Explorer. In the event that processing for Case 1 was still in progress at the time of the query, the database 2206 also includes information about Case 1 and such information may also be returned in response to a query.

The client 2210 may be used to obtain report information in accordance with a query. The information may be in connection with an order that is in progress, or has completed processing. An embodiment may similarly provide report information for any one or more purposes to a client. The IPS may act as a server serving up report information in the form of HTML, XML, and the like, to a client for operations in connection with reporting. It should be noted that the report generating functionality may be provided by the VLM or other component. In one embodiment, the VLM may manage the web pages which are in XML. As known to those of ordinary skill in the art, XML may be transformed into a variety of different formats and styles using, for example, XSLT Transforms. The transformed and populated web page may be returned to the client.

The IPS, such as the VLM and/or other component(s) executing on the IPS in one embodiment as described herein, may also perform product inventory and tracking. Code may be executed on the IPS to obtain historical data, for example, about historical use of reagents over time, detect re-order threshold limits, and maintain just-in-time product inventory. The IPS may include a background thread that runs in a continuous manner monitoring reagent inventory and determining, based on historical usage and/or expiration dates, when one or more reagents fall below a threshold level triggering a reorder. For example, based on historical usage, expiration information of reagents, and the amount of time it may take to obtain a reagent, reorders may be automatically generated by the IPS. The IPS, such as the VLM and/or other component(s) executing on the IPS in one embodiment described herein, may be connected to another system providing pricing models. Based on expiration date of a particular reagent, it may be determined automatically to reorder in a particular quantity to obtain a discount currently being offered by a reagent supplier. Such pricing information, discounts and the like may vary over time. In one embodiment, the foregoing functionality of product inventory and/or tracking may be performed through a cooperative and communicative effort of one or more components such as, for example, inventory management functionality for each host (e.g., historical data), RFID tracking (e.g., more current reagent information than may be available otherwise), and a component such as the VLM and/or Webserver serving reports.

Reagents may include modifiable or writeable RFID labels that may be updated to reflect a current quantity. Such information may be read from the RFID labels of the reagents and other supplies to provide real time inventory information. The inventory information may be sent to a host or other system in communication with the RFID components. The host or other system may then relay such information to the IPS, such as the VLM within the IPS, and/or other component(s) that may be used in an embodiment in performing inventory management.

The VLM or other component, when performing inventory and tracking, may communicate with one or more other systems (not shown) to provide further integration of operations in connection with ordering and tracking. For example, in one embodiment the VLM and other components performing the inventory and tracking may execute on the IPS. In connection with performing inventory and tracking operations, these components may communicate with an accounting system to streamline order approval process. The IPS may also communicate with an electronic system of the reagent supplier, for example, to electronically place an order for supplies. The IPS may further communicate electronically with a system of a selected delivery service, such as UPS, Federal Express, and the like, to provide information about the progress of delivery. Information about an order, inventory, and the like, may be provided through reporting functionality to a client from the IPS acting as a server as described above.

The foregoing are some examples of different functionalities that may be provided through integration of one or more systems. The particular functionalities may vary with each embodiment.

QC processing may be performed in an embodiment in a variety of different aspects as described herein. As another form of QC, the IPS may include a component such as the VLM or other component which communicates with the hosts to perform QC processing in accordance with aggregated test results from one or more slides or other sample in a case and with a template. In one embodiment, the hosts may perform QC testing in accordance with the template. Each host's QC testing information may be replicated to other hosts using the VLM and other techniques described herein. The template may define, for example, certain expected combinations of test results. In the event that the aggregated test results do not fit one of the expected combinations, the IPS or one or more of the hosts may automatically reorder one or more tests. In addition to, or as an alternative to defining acceptable test results, the template may define an action to be taken if the aggregated test results are one of the defined erroneous QC patterns.

Figure 34:
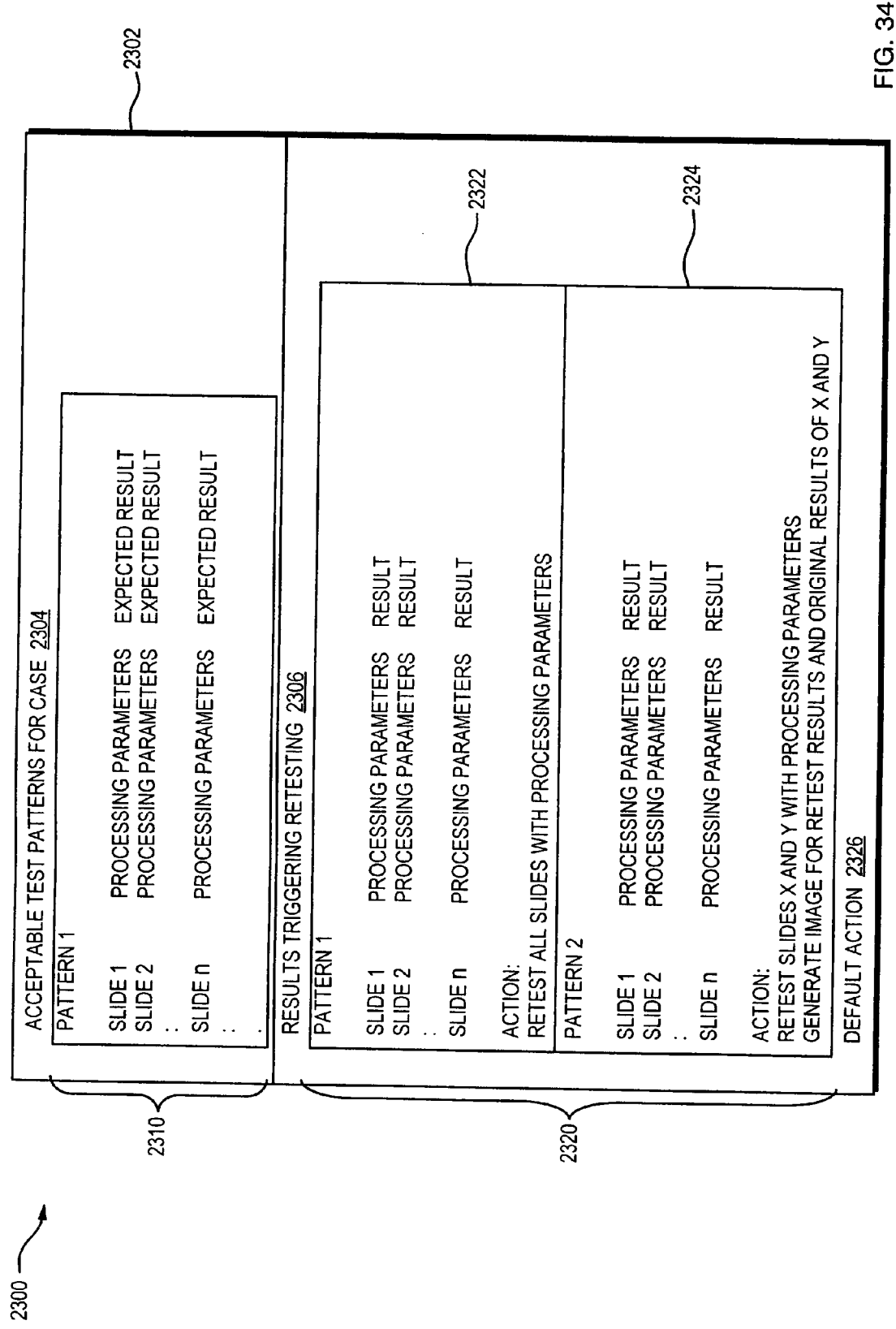
FIG. 34 is an example representation of an embodiment of a template that may be used in connection with automating processing for retesting.

Referring now to FIG. 34, shown is an example representation of a template that may be used in automating QC processing for retesting. The template may be stored, for example, in the database of the IPS. The example 2300 includes a template 2302 with a set of acceptable test result patterns in area 2304 and a set of results triggering retesting in area 2306. The area 2302 includes one or more test result patterns. The area 2306 includes a set of test results and one or more actions to be taken if the defined test result is determined. For example, if pattern 1 in area 2306 is determined, all slides are retested. The particular information for retesting may also be included in the template. An embodiment may also include a template which includes only area 2306. If a case meets one of the specified patterns in section 2306, then retesting is performed. Otherwise, it may be determined that the results are acceptable. In an embodiment including both sections 2302 and 2306, a test pattern may be specified in section 2326 which covers all remaining conditions. In the event that one of the conditions in sections 2304 and 2306 are not met, the default action in 2326 may be performed. An embodiment may use any one of a variety of different formats and techniques for the template specification and evaluation. This automated retesting may be performed, for example, by each host, by the IPS, on another system on which the VLM is executing in one embodiment, or on other components in the system described herein. In one embodiment, a QC failure as detected by one host using a particular reagent, for example, on a rejected stained slide may cause other hosts to place on hold any further processing of all reagents used on the rejected stained slide. In other words, any further use of all reagents used on the rejected slide may be put on hold. The QC failure may be determined by a host. Upon detection of this failure, the host, VLM, or other component in communication with the detecting host, may determine which other reagents were used on the rejected stained slide. The data within the database as maintained by the VLM may be updated to reflect that further processing for the one or more suspect reagents is on hold. This information may then be replicated to the other hosts via the VLM.

In connection with a QA failure, the failure may involve one or more instruments and/or one or more elements used in connection with processing such as, for example, a reagent. In response to the detected QA failure, an embodiment may perform any one or more different actions. In one embodiment, a lockout process may be performed such that, for example, further processing involving the instrument, reagent and/or other component associated with the failure is disallowed. An embodiment may also take other actions, besides a lockout, in connection with the QA failure. The actions may be of varying degrees of severity, for example, that may vary in accordance with the particular QA failure. For example, an embodiment may allow subsequent use of an instrument, reagent, and/or other component associated with a QA failure coupled with notification of the detected failure. An embodiment may, for example, output a notification to any one or more output devices regarding the QA failures detected. To continue to use the instrument, reagent, or other element associated with the QA failure, a technician may have to acknowledge the QA failure and positively indicate approval (e.g., input through a graphical user interface) to continue to use the elements associated with the QA failure. It should be noted that a QA failure may be associated with any one of a variety of different criteria and qualifications. For example, certain QA requirements may be specified by a first set of regulations for certifying or qualifying a reagent, instrument, and the like. A QA failure may be associated with one or more of these regulation sets and/or elements (e.g, reagent, instrument, and the like).

In response to the detection of a QA failure, a report or other notification message may be automatically generated and sent to a lab manager, technician, and the like. The notification may take the form of an electronic notification such as, for example, an e-mail message, pager notification, and the like. Such notification and/or report generation may occur with all QA failures, or a portion of detected failures meeting predetermined criteria such as, for example, a particular severity level, if a certain number and/or type of failures are detected in a defined time period, and the like.

An embodiment may also include a report generation functionality which allows a user, for example, to selectively request certain information regarding QA failures and generate a report in response to the particular user criteria.

The reports and/or notifications may include varying levels of detailed information the varying level of detail may be in accordance with specified criteria including, for example, user specified criteria, a severity level, regulations or other compliance criteria, and the like.

It should be noted that the foregoing system, may include any one or more different types of instruments. In one embodiment with reference to FIG. 3 elements, an instrument 114 may be an imager. The imager may produce an image file as described elsewhere herein. As a result of processing performed by the imager, image information may be produced. The image information may include image data stored in a particular file type and/or format. The image information, or portions thereof, may be stored locally in a memory on the imager, uploaded to the host controlling the imager, and/or replicated on the other hosts using techniques described herein in accordance with the particular configurations of each host and the system. In one embodiment, the image file may be stored on a storage device, for example, attached to the instrument and/or host. The image file name and/or all or a portion of the image file data may be uploaded from the instrument. In an embodiment as described elsewhere herein using writeable RFID labels, the image file name and/or a portion of the image file data may be written to the RFID label. It should be noted that the image file data, or portion thereof, as may be written to the RFID label may be stored in a format, such as a compressed or other format. The imager, or other instrument as may be included in an embodiment, may also report the identity of slides, or selected samples being processed at certain times, to the host. Such information may be replicated to the other hosts and/or database and used, for example, to locate one or more particular slides, samples, and the like.

The foregoing describes a system in which hosts can be networked to communicate with each other to form an integrated laboratory environment. The components of the systems described herein, such as in FIG. 3, may all be physically located in a same location, or may be located in one or more different locations. Components that are in different locations may communicate with other components using any one of a variety of different connections as known to those of ordinary skill in the art. For example, the LIS may be remotely located from the IPS and hosts. It should also be noted that although example embodiments described herein may be fully integrated and connected, those of ordinary skill in the art will appreciate that techniques described herein may also be used in embodiments in which not all the components are connected or as described herein. For example, the techniques described herein using RFID labels to track slides in a laboratory may also be used in an embodiment having only IPS-host connectivity without LIS-IPS connectivity.

A system as described herein may provide configurable data sharing between one or more hosts using the VLM that may be included in an embodiment. Data may be automatically replicated on each host. Reagents, protocol assignments, user privileges, and the like, that may be registered on different hosts may be replicated automatically to all hosts. For example, the VLM may act as a data repository for the latest version of data by having hosts constantly send updated data to the VLM and additionally having the hosts request and receive any data updated from the VLM. As a benefit of data sharing and replication, slide label printing can be performed on any host. Slide labels can be configured to print automatically when an order is received from the LIS when using optional VIP software. In one embodiment, this may be performed in connection with order placement. For example, when an order is placed in the VIP via HL7 messaging, an embodiment may include one or more fields in a message to facilitate label printing options. A configuration data element may be used to indicate a particular host and associated printer is to be used for label printing. Additionally, the same or different data element may include a printing mode indicator. In one embodiment, the printing mode indicator may be queued or pass through. The queued mode indicates that any labels for the associated order remain in the label printing queue until a subsequent request, such as by a user, is made to print the labels. In queued mode, the label printing is not automatic. If pass through mode is specified, once the designated host and printer is aware of the new order, the label(s) associated with that order print automatically. The printing option may be specified on a per order basis in an embodiment. Alternatively, an embodiment may also include a configuration option, such as the site bar code symbology configuration option described elsewhere herein, that may be used for new orders. The configuration option may include the particular host and/or printer designation as well as the particular printing mode. The foregoing also provides for communication via messaging between the LIS and components of the laboratory through the a single interface point, the VIP. A bidirectional interface is described that provides for orders to be sent to the laboratory and status and report information to be sent back to the LIS. As part of the order information, case data including patient information and other data is communicated from the LIS to the laboratory eliminating the need for manual patient data entry and possible re-entry. The benefits of the features described herein, such as the LIS connectivity for slide ordering and label printing, may be more apparent in larger laboratory environments.

It should be noted that the functionality described herein for performing processing may be implemented in hardware and/or software in an embodiment. It should also be noted that although examples and illustrative embodiments described herein set forth particular configurations of functionality as may be performed by particular software and/or hardware components, other variations and configurations are possible as known to those of ordinary skill in the art.

While the invention has been described with reference to an illustrative embodiment, it will be understood by those skilled in the art that various changes, omissions and/or additions may be made and equivalents may be substituted for elements thereof without departing from the spirit and scope of the invention. In addition, many modifications may be made to adapt a particular situation or material to the teachings of the invention without departing from the scope thereof. Therefore, it is intended that the invention not be limited to the particular embodiment disclosed as the best mode contemplated for carrying out this invention, but that the invention will include all embodiments falling within the scope of the appended claims. Moreover, unless specifically stated any use of the terms first, second, etc. do not denote any order or importance, but rather the terms first, second, etc. are used to distinguish one element from another.

What is claimed is:

1. A method for processing a sample in an anatomical pathology laboratory comprising:
   providing a host controlling at least one instrument in the anatomical pathology laboratory, said host being configured to have at least one local data element and at least one global data element and said host being configured to identify samples in the laboratory using radio frequency identification labels associated with the samples, said at least one global data element having a common data definition and data value used by said host and at least one other host connected to said host, said at least one local data element having a data definition and data value used only by said host, wherein said at least one instrument controlled by the host includes a first stainer that uses a first reagent, wherein said at least one global data element includes a first global data element that is associated with the first reagent and indicates the first reagent is currently owned by the host thereby indicating that the first reagent physically resides at an instrument controlled by the host;
   receiving a first of said samples, said first sample being a tissue sample associated with a radio frequency identification label encoded with a tissue sample identifier including a first part representing a tissue source, a second part representing a year associated with the tissue sample, and a tissue sequence number;
   partitioning the first sample into one or more blocks, each of said blocks associated with a different block identifier;
   preparing a set of one or more slides from said first sample, each of said one or more slides having a portion of said first sample on a surface of said each slide and being cut from one of said blocks;
   preparing a radio frequency identification label for each of said one or more slides in the set, said radio frequency identification label being affixed to said each slide and having a slide identifier encoded thereon that uniquely identifies said each slide, wherein said slide identifier for said each slide having the portion of the first sample thereon includes the tissue sample identifier, a block identifier associated with one of the blocks from which the portion was cut, and a slide sequence number;

performing one or more processing steps in said laboratory to at least a first slide of said set of one or more slides, wherein said performing includes:
- reading the slide identifier from the radio frequency identification label for said first slide;
- accessing information for said first slide in a database using said slide identifier of the first slide, wherein said accessing is performed by a computer using said slide identifier and obtains information including a first staining protocol which indicates to perform staining of the first slide using one or more reagents including said first reagent;
- staining said first slide in accordance with the first staining protocol using said first stainer controlled by the first host; and
- writing to said radio frequency identification label of said first slide by encoding said radio frequency identification label with information related to at least one of said one or more processing steps as said first slide is processed.

2. The method of claim 1, wherein said information written to said radio frequency identification label of said first slide includes at least one of patient information, hospital accession information, test information, and batch information used to identify at least one other slide and said each slide as being from a same processing batch.

3. The method of claim 1, wherein said information includes test information about at least one test performed on said first slide in one of the processing steps in the anatomical pathology laboratory.

4. The method of claim 3, further comprising:
reading said test information from said radio frequency identification label of said first slide in connection with a test to be performed to said first slide as a step in laboratory processing, said reading being performed prior to performing said test in order to verify processing for said test.

5. The method of claim 4, further comprising:
writing to said radio frequency identification label of said first slide by encoding said radio frequency identification label of the first slide with additional information about said test, said additional information including at least one of: time, date, test parameters, filename, test results, information about a reagent used in testing, information about a technician performing a processing step, and information about an instrument used to process said first slide.

6. The method of claim 5, wherein said filename identifies an image file.

7. The method of claim 5, further comprising:
reading at least a portion of said additional information;
determining a diagnosis in accordance with said portion; and
encoding said radio frequency identification label of said first slide with data about said diagnosis.

8. The method of claim 2, wherein said information written to said radio frequency identification label of the first slide includes batch information, and the method further comprising:
determining a plurality of slides belonging to a same group in accordance with said batch information encoded on radio frequency identification labels of said plurality of slides.

9. The method of claim 1, further comprising:
writing information to said radio frequency identification label of said first slide in the anatomical pathology laboratory at a processing point when said staining is performed to said first slide.

10. The method of claim 1, further comprising:
receiving, by said radio frequency identification label associated with the first slide, an interrogator signal;
transmitting, by said radio frequency identification label associated with the first slide in response to said interrogator signal, an electromagnetic response signal including at least a first slide identifier used by said host for uniquely identifying said first slide.

11. The method of claim 10, wherein said electromagnetic response signal is produced using information encoded in said first radio frequency identification label associated with said first slide.

12. The method of claim 11, further comprising:
determining a location of said first slide in said anatomical pathology laboratory in accordance with said electromagnetic response signal.

13. The method of claim 1, further comprising:
receiving, by said radio frequency identification label associated with said first sample, an interrogator signal;
transmitting, by said radio frequency identification label associated with said first sample in response to said interrogator signal, an electromagnetic response signal including at least a first portion used by said host for uniquely identifying said first sample.

14. The method of claim 1, further comprising:
comparing, as part of a quality control check at a processing point in the anatomical pathology laboratory, a portion of information read from the radio frequency identification label associated with the first sample to other information stored in a database used by said host.

15. The method of claim 1, wherein said slide identifier associated with said each slide is used to access from the database one or more data elements associated with said each slide, said one or more data elements including a global data element.

16. The method of claim 15, wherein said global data element is any of a case identifier, a staining protocol used to process said each slide, a reagent used to process said each slide, and a location of an image file containing image results for said each slide.

17. The method of claim 1, wherein said first part of the tissue sample identifier includes a first letter of an alphabet if said tissue source is surgery, a second letter of an alphabet if said tissue source is bone marrow, and another letter of an alphabet if otherwise.

18. The method of claim 1, wherein said host and said at least one other host are in communication with an interface point server that facilitates synchronization and replication of said at least one global data element between said host and said at least one other host.

* * * * *